United States Patent [19]

Barenkamp et al.

[11] Patent Number: 5,869,065

[45] Date of Patent: *Feb. 9, 1999

[54] HIGH MOLECULAR WEIGHT SURFACE PROTEINS OF NON-TYPEABLE HAEMOPHILUS

[75] Inventors: Stephen J. Barenkamp, Webster Grove; Joseph William St. Geme, III, St. Louis, both of Mo.

[73] Assignee: Board of Trustees of the Leland Stanford Junior University, Stanford, Calif.

[ * ] Notice: The term of this patent shall not extend beyond the expiration date of Pat. No. 5,548,897.

[21] Appl. No.: 530,198

[22] PCT Filed: Mar. 15, 1994

[86] PCT No.: PCT/US94/02550

§ 371 Date: Dec. 13, 1995

§ 102(e) Date: Dec. 13, 1995

[87] PCT Pub. No.: WO94/21290

PCT Pub. Date: Sep. 29, 1994

[51] Int. Cl.⁶ .................................................. A61K 39/102
[52] U.S. Cl. ..................................... 424/256.1; 424/185.1; 424/190.1; 530/350; 536/23.1; 536/23.7

[58] Field of Search ............................... 424/185.1, 256.1, 424/190.1; 530/350; 536/23.1, 23.7

[56] References Cited

PUBLICATIONS

Barenkamp et al. Infection & Immunity Apr. 1992 60(4): pp. 1302–1313.

Barenkamp (Ped. Res. 1991 29(4) pt. 2., 167A, Abstract No. 985).

Barenkamp et al. (Ped. Inf. Dis. J. 1990 9(5):333–339.

*Primary Examiner*—James C. Housel
*Assistant Examiner*—Jennifer Shaver
*Attorney, Agent, or Firm*—Shoemaker and Mattare, Ltd.

[57] ABSTRACT

High molecular weight surface proteins of non-typeable *Haemophilus influenzae* which exhibit immunogenic properties and genes encoding the same are described. Specifically, genes coding for two immunodominant high molecular weight proteins, HMW1 and HMW2, have been cloned, expressed and sequenced, while genes coding for high molecular proteins HMW3 and HMW4 have been cloned, expressed and partially sequenced.

1 Claim, 68 Drawing Sheets

FIG. 1A. DNA SEQUENCE OF HIGH MOLECULAR WEIGHT PROTEIN I (HMW1)

```
  1  ACAGCGTCT CTTAATACTA GTACAAACCC ACAATAAAAT ATGACAAACA
 51  ACAATTACAA CACCTTTTTT GCAGTCTATA TGCAAATATT TTAAAAAATA
101  GTATAAATCC GCCATATAAA ATGGTATAAT CTTTCATCTT TCATCTTTCA
151  TCTTTCATCT TTCATCTTTC ATCTTTCATC TTTCATCTTT CATCTTTCAT
201  CTTTCATCTT TCATCTTTCA TCTTTCATCT TTCATCTTTC ACATGCCCTG
251  ATGAACCGAG GGAAGGGAGG GAGGGGCAAG AATGAAGAGG GAGCTGAACG
301  AACGCAAATG ATAAAGTAAT TTAATTGTTC AACTAACCTT AGGAGAAAAT
351  ATGAACAAGC TATATCGTCT CAAATTCAGC AAACGCCTGA ATGCTTTGGT
401  TGCTGTGTCT GAATTGGCAC GGGGTTGTGA CCATTCCACA GAAAAAGGCA
451  GCGAAAAACC TGCTCGCATG AAAGTGCGTC ACTTAGCGTT AAAGCCACTT
501  TCCGCTATGT TACTATCTTT AGGTGTAACA TCTATTCCAC AATCTGTTTT
551  AGCAAGCGGC TTACAAGGAA TGGATGTAGT ACACGGCACA GCCACTATGC
601  AAGTAGATGG TAATAAAACC ATTATCCGCA ACAGTGTTGA CGATATCATT
651  AATTGGAAAC AATTTAACAT CGACCAAAAT GAAATGGTGC AGTTTTACA
701  AGAAAACAAC AACTCCGCCG TATTCAACCG TGTTACATCT AACCAAATCT
```

FIG. 1B.

```
751   CCCAATTAAA AGGGATTTTA GATTCTAACG GACAAGTCTT TTTAATCAAC
801   CCAAATGGTA TCACAATAGG TAAAGACGCA ATTATTAACA CTAATGGCTT
851   TACGGCTTCT ACGCTAGACA TTTCTAACGA AAACATCAAG GCGCGTAATT
901   TCACCTTCGA GCAAACCAAA GATAAAGCGC TCGCTGAAAT TGTGAATCAC
951   GGTTTAATTA CTGTCGGTAA AGACGGCAGT GTAAATCTTA TTGGTGGCAA
1001  AGTGAAAAAC GAGGGTGTGA TTAGCGTAAA TGGTGGCAGC ATTTCTTTAC
1051  TCGCAGGGCA AAAAATCACC ATCAGCGATA TAATAAACCC AACCATTACT
1101  TACAGCATTG CCGCGCCTGA AAATGAAGCG GTCAATCTGG GCGATATTTT
1151  TGCCAAAGGC GGTAACATTA ATGTCCGTGC TGCCACTATT CGAAACCAAG
1201  GTAAACTTTC TGCTGATTCT GTAAGCAAAG ATAAAAGCGG CAATATTGTT
1251  CTTTCCGCCA AAGAGGGTGA AGCGGAAATT GGCGGTGTAA TTTCCGCTCA
1301  AAATCAGCAA GCTAAAGGCG GCAAGCTGAT GATTACAGGC GATAAAGTCA
1351  CATTAAAAAC AGGTGCAGTT ATCGACCTTT CAGGTAAAGA AGGGGAGAA
1401  ACTTACCTTG GCGGTGACGA GCGCGGGCGAA GGTAAAAAGG GCATTCAATT
1451  AGCAAAGAAA ACCTCTTTAG AAAAAGGCTC AACCATCAAT GTATCAGGCA
1501  AAGAAAAAGG CGGACGCGCT ATTGTGTGGG GCGATATTGC GTTAATTGAC
```

FIG. 1C.

```
1551  GGCAATATTA  ACGCTCAAGG  TAGTGGTGAT  ATCGCTAAAA  CCGGTGGTTT
1601  TGTGGAGACG  TCGGGGCATG  ATTTATTCAT  CAAAGACAAT  GCAATTGTTG
1651  ACGCCAAAGA  GTGGTTGTTA  GACCCGGATA  ATGTATCTAT  TAATGCAGAA
1701  ACAGCAGGAC  GCAGCAATAC  GATGAATACA  GATGAATACA  CGGGATCCGG
1751  GAATAGTGCC  AGCACCCCAA  AACGAAACAA  AGAAAAGACA  ACATTAACAA
1801  ACACAACTCT  TGAGAGTATA  CTAAAAAAAG  GTACCTTTGT  TAACATCACT
1851  GCTAATCAAC  GCATCTATGT  CAATAGCTCC  ATTAATTTAT  CCAATGGCAG
1901  CTTAACTCTT  TGGAGTGAGG  GTCGGAGCGG  TGGCGGCGTT  GAGATTAACA
1951  ACGATATTAC  CACCGGTGAT  GATACCAGAG  GTGCAAACTT  AACAATTTAC
2001  TCAGGCGGCT  GGGTTGATGT  TCATAAAAAT  ATCTCACTCG  GGGCGCAAGG
2051  TAACATAAAC  ATTACAGCTA  AACAAGATAT  CGCCTTTGAG  AAAGGAAGCA
2101  ACCAAGTCAT  TACAGGTCAA  GGGACTATTA  CCTCAGGCAA  TCAAAAGGT
2151  TTTAGATTTA  ATAATGTCTC  TCTAAACGGC  ACTGGCAGCG  GACTGCAATT
2201  CACCACTAAA  AGAACCAATA  AATACGCTAT  CACAAATAAA  TTTGAAGGGA
2251  CTTTAAATAT  TTCAGGGAAA  GTGAACATCT  CAATGGTTTT  ACCTAAAAAT
2301  GAAAGTGGAT  ATGATAAATT  ACTTACTGGA  CAAAGGACGC  ATTTAACCTC
```

FIG. 1D.

```
2351  CTTAAATGTT  TCCGAGAGTG  GCGAGTTTAA  CCTCACTATT  GACTCCAGAG
2401  GAAGCGATAG  TGCAGGCACA  CTTACCCAGC  CTTATAATTT  AAACGGTATA
2451  TCATTCAACA  AAGACACTAC  CTTTAATGTT  GAACGAAATG  CAAGAGTCAA
2501  CTTTGACATC  AAGGCACCAA  TAGGGATAAA  TAAGTATTCT  AGTTTGAATT
2551  ACGCATCATT  TAATGGAAAC  ATTTCAGTTT  CGGGAGGGGG  GAGTGTTGAT
2601  TTCACACTTC  TCGCCCTCATC  CTCTAACGTC  CAAACCCCCG  GTGTAGTTAT
2651  AAATTCTAAA  TACTTTAATG  TTTCAACAGG  GTCAAGTTTA  AGATTAAAA
2701  CTTCAGGCTC  AACAAAAACT  GGCTTCTCAA  TAGAGAAAGA  TTTAACTTTA
2751  AATGCCACCG  GAGGCAACAT  AACACTTTTG  CAAGTTGAAG  GCACCGATGG
2801  AATGATTGGT  AAAGGCATTG  TAGCCAAAAA  AAACATAACC  TTTGAAGGAG
2851  GTAACATCAC  CTTTGGCTCC  AGGAAAGCCG  TAACAGAAAT  CGAAGGCAAT
2901  GTTACTATCA  ATAACAACGC  TAACGTCACT  CTTATCGGTT  CGGATTTTGA
2951  CAACCATCAA  AAACCTTTAA  CTATTAAAAA  AGATGTCATC  ATTAATAGCG
3001  GCAACCTTAC  CGCTGGAGGC  AATATTGTCA  ATATAGCCGG  AAATCTTACC
3051  GTTGAAAGTA  ACGCTAATTT  CAAAGCTATC  ACAAATTTCA  CTTTAATGT
3101  AGGCGGCTTG  TTTGACAACA  AAGGCAATTC  AAATATTTCC  ATTGCCAAAG
3151  GAGGGGCTCG  CTTTAAAGAC  ATTGATAATT  CCAAGAATTT  AAGCATCACC
```

FIG. 1E.

```
3201 ACCAACTCCA GCTCCACTTA CCGCACTATT ATAAGCGGCA ATATAACCAA
3251 TAAAAACGGT GATTTAAATA TTACGAACGA AGGTAGTGAT ACTGAAATGC
3301 AAATTGGCGG CGATGTCTCG CAAAAAGAAG GTAATCTCAC GATTTCTTCT
3351 GACAAAATCA ATATTACCAA ACAGATAACA ATCAAGGCAG GTGTTGATGG
3401 GGAGAATTCC GATTCAGACG CGACAAACAA TGCCAATCTA ACCATTAAAA
3451 CCAAAGAATT GAAATTAACG CAAGACCTAA ATATTTCAGG TTTCAATAAA
3501 GCAGAGATTA CAGCTAAAGA TGGTAGTGAT TTAACTATTG GTAACACCAA
3551 TAGTGCTGAT GGTACTAATG CCAAAAAAGT AACCTTTAAC CAGGTTAAAG
3601 ATTCAAAAAT CTCTGCTGAC GGTCACAAGG TGACACTACA CAGCAAAGTG
3651 GAAACATCCG GTAGTAATAA CAACACTGAA GATAGCAGTG ACAATAATGC
3701 CGGCTTAACT ATCGATGCAA AAAATGTAAC AGTAAACAAC AATATTACTT
3751 CTCACAAAGC AGTGAGCATC TCTGCGACAA GTGGAGAAAT TACCACTAAA
3801 ACAGGTACAA CCATTAACGC AACCACTGGT AACGTGGAGA TAACCGCTCA
3851 AACAGGTAGT ATCCTAGGTG GAATTGAGTC CAGCTCTGGC TCTGTAACAC
3901 TTACTGCAAC CGAGGGCGCT CTTGCTGTAA GCAATATTTC GGGCAACACC
3951 GTTACTGTTA CTGCAAATAG CGGTGCATTA ACCACTTTGG CAGGCTCTAC
```

FIG. 1F.

```
4001 AATTAAAGGA ACCGAGAGTG TAACCACTTC AAGTCAATCA GGCGATATCG
4051 GCGGTACGAT TTCTGGTGGC ACAGTAGAGG TTAAAGCAAC CGAAAGTTTA
4101 ACCACTCAAT CCAATTCAAA AATTAAAGCA ACAACAGGCG AGGCTAACGT
4151 AACAAGTGCA ACAGGTACAA TTGGTGGTAC GATTTCCGGT AATACGGTAA
4201 ATGTTACGGC AAACGCTGGC GATTTAACAG TTGGGAATGG CGCAGAAATT
4251 AATGCGACAG AAGGAGCTGC AACCTTAACT ACATCATCGG GCAAATTAAC
4301 TACCGAAGCT AGTTCACACA TTACTTCAGC CAAGGGTCAG GTAAATCTTT
4351 CAGCTCAGGA TGGTAGCGTT GCAGGAAGTA TTAATGCCGC CAATGTGACA
4401 CTAAATACTA CAGGCACTTT AACTACCGTG AAGGGTTCAA ACATTAATGC
4451 AACCAGCGGT ACCTTGGTTA TTAACGCAAA AGACGCTGAG CTAAATGGCG
4501 CAGCATTGGG TAACCACACA GTGGTAAATG CAACCAACGC AAATGGCTCC
4551 GGCAGCGTAA TCGCGACAAC CTCAAGCAGA GTGAACATCA CTGGGGATTT
4601 AATCACAATA AATGGATTAA ATATCATTTC AAAAAACGGT ATAAACACCG
4651 TACTGTTAAA AGGCGTTAAA ATTGATGTGA AATACATTCA ACCGGGTATA
4701 GCAAGCGTAG ATGAAGTAAT TGAAGCGAAA CGCATCCTTG AGAAGGTAAA
4751 AGATTTATCT GATGAAGAAA GAGAAGCGTT AGCTAAACTT GGAGTAAGTG
4801 CTGTACGTTT TATTGAGCCA AATAATACAA TTACAGTCGA TACACAAAT
```

FIG. 1G.

```
4851  GAATTTGCAA  CCAGACCATT  AAGTCGAATA  GTGATTTCTG  AAGGCAGGGC
4901  GTGTTTCTCA  AACAGTGATG  GCGCGACGGT  GTGCCGTTAAT ATCGCTGATA
4951  ACGGGCGGTA  GCGGTCAGTA  ATTGACAAGG  TAGATTTCAT  CCTGCAATGA
5001  AGTCATTTTA  TTTTCGTATT  ATTTACTGTG  TGGGTTAAAG  TTCAGTACGG
5051  GCTTTACCCA  TCTTGTAAAA  AATTACGGAG  AATACAATAA  AGTATTTTA
5101  ACAGGTTATT  ATTATG
```

FIG. 2A. AMINO ACID SEQUENCE OF HIGH MOLECULAR WEIGHT PROTEIN I

```
  1  MNKIYRLKFS KRLNALVAVS ELARGCDHST EKGSEKPARM KVRHLALKPL
 51  SAMLLSLGVT SIPQSVLASG LQGMDVVHGT ATMQVDGNKT IIRNSVDAII
101  NWKQFNIDQN EMVQFLQENN NSAVFNRVTS NQISQLKGIL DSNGQVFLIN
151  PNGITIGKDA IINTNGFTAS TLDISNENIK ARNFTFEQTK DKALAEIVNH
201  GLITVGKDGS VNLIGGKVKN EGVISVNGGS ISLLAGQKIT ISDIINPTIT
251  YSIAAPENEA VNLGDIFAKG GNINVRAATI RNQGKLSADS VSKDKSGNIV
301  LSAKEGEAEI GGVISAQNQQ AKGGKLMITG DKVTLKTGAV IDLSGKEGGE
351  TYLGGDERGE GKNGIQLAKK TSLEKGSTIN VSGKEKGGRA IVWGDIALID
401  GNINAQGSGD IAKTGGFVET SGHDLFIKDN AIVDAKEWLL DFDNVSINAE
451  TAGRSNTSED DEYTGSGNSA STPKRNKEKT TLTNTTLESI LKKGTFVNIT
501  ANQRIYVNSS INLSNGSLTL WSEGRSGGGV EINNDITTGD DTRGANLTIY
551  SGGWVDVHKN ISLGAQGNIN ITAKQDIAFE KGSNQVITGQ GTITSGNQKG
601  FRFNNVSLNG TGSGLQFTTK RTNKYAITNK FEGTLNISGK VNISMVLPKN
651  ESGYDKFKGR TYWNLTSLNV SESGEFNLTI DSRGSDSAGT LTQPYNLNGI
701  SFNKDTTFNV ERNARVNFDI KAPIGINKYS SLNYASFNGN ISVSGGGSVD
```

FIG. 2B.

```
 751  FTLLASSSNV  QTPGVVINSK  YFNVSTGSSL  RFKTSGSTKT  GFSIEKDLTL
 801  NATGGNITLL  QVEGTDGMIG  KGIVAKKNIT  FEGGNITFGS  RKAVTEIEGN
 851  VTINNNANVT  LIGSDFDNHQ  KPLTIKKDVI  INSGNLTAGG  NIVNIAGNLT
 901  VESNANFKAI  TNFTFNVGGL  FDNKGNSNIS  IAKGGARFKD  IDNSKNLSIT
 951  TNSSSTYRTI  ISGNITNKNG  DLNITNEGSD  TEMQIGGDVS  QKEGNLTISS
1001  DKINITKQIT  IKAGVDGENS  DSDATNNANL  TIKTKELKLT  QDLNISGFNK
1051  AEITAKDGSD  LTIGNTNSAD  GTNAKKVTFN  QVKDSKISAD  GHKVTLHSKV
1101  ETSGSNNNTE  DSSDNNAGLT  IDAKNVTVNN  NITSHKAVSI  SATSGEITTK
1151  TGTTINATTG  NVEITAQTGS  ILGGIESSSG  SVTLTATEGA  LAVSNISGNT
1201  VTVTANSGAL  TTLAGSTIKG  TESVTTSSQS  GDIGGTISGG  TVEVKATESL
1251  TTQSNSKIKA  TGTIGGTISG  NTVNVTANAG  DLTVGNGAEI
1301  NATEGAATLT  TSSGKLTTEA  SSHITSAKGQ  VNLSAQDGSV  AGSINAANVT
1351  LNTTGTLTTV  KGSNINATSG  TLVINAKDAE  LNGAALGNHT  VVNATNANGS
1401  GSVIATTSSR  VNITGDLITI  NGLNIISKNG  INTVLLKGVK  IDVKYIQPGI
1451  ASVDEVIEAK  RILEKVKDLS  DEEREALAKL  GVSAVRFIEP  NNTITVDTQN
1501  EFATRPLSRI  VISEGRACFS  NSDGATVCVN  IADNGR
```

FIG. 3A. AMINO ACID SEQUENCE OF HIGH MOLECULAR WEIGHT PROTEIN II (HMW2)

```
  1  TAAATATACA AGATAATAAA AATAAATCAA GATTTTTGTG ATGACAAACA
 51  ACAATTACAA CACCTTTTTT GCAGTCTATA TGCAAATATT TTAAAAAAAT
101  AGTATAAATC CGCCATATAA AATGGTATAA TCTTTCATCT TTCATCTTTA
151  ATCTTTCATC TTTCATCTTT CATCTTTCAT ATCTTTCATC TCATCTTTCA
201  TCTTTCATCT TTCATCTTTC ATCTTTCATC TTTCATCTTT CACATGAAAT
251  GATGAACCGA GGGAAGGGAG GGAGGGGCAA TTTAATTGTT GGAGCTGAAC
301  GAACGCAAAT GATAAAGTAA TTTAATTGTT CAACTAACCT TAGGAGAAAA
351  TATGAACAAG ATATATCGTC TCAAATTCAG CAAACGCCTG AATGCTTTGG
401  TTGCTGTGTC TGAATTGGCA CGGGGTTGTG ACCATTCCAC AGAAAAAGGC
451  TTCCGCTATG TTACTATCTT TAGGTGTAAC CACTTAGCGT TAAAGCCACT
501  TTCCGCTATG TTACTATCTT TAGGTGTAAC ATCTATTCCA CAATCTGTTT
551  TAGCAAGCGG CTTACAAGGA ATGGATGTAG TACACGGCAC AGCCACTATG
601  CAAGTAGATG GTAATAAAAC CATTATCCGC AACAGTGTTG ACGTATCAT
651  TAATTGGAAA CAATTTAACA TCGACCAAAA TGAAATGGTG CAGTTTTTAC
701  AAGAAAACAA CAACTCCGCC GTATTCAACC GTGTTACATC TAACCAAATC
```

FIG. 3B.

```
 751 TCCCAATTAA AAGGGATTTT AGATTCTAAC GGACAAGTCT TTTTAATCAA
 801 CCCAAATGGT ATCACAATAG GTAAAGACGC AATTATTAAC ACTAATGGCT
 851 TTACGGCTTC TACGCTAGAC ATTTCTAACG AAAACATCAA GGCGCGTAAT
 901 TTCACCTTCG AGCAAACCAA AGATAAAGCG CTCGCTGAAA TTGTGAATCA
 951 CGGTTTAATT ACTGTCGGTA AAGACGGCAG TGTAAATCTT ATTGGTGGCA
1001 AAGTGAAAAA CGAGGGTGTG ATTAGCGTAA ATGGTGGCAG CATTTCTTTA
1051 CTCGCAGGGC AAAAAATCAC CATCAGCGAT ATAATAAACC CAACCATTAC
1101 TTACAGCATT GCCGCGCCTG AAAATGAAGC GGTCAATCTG GGCGATATTT
1151 TTGCCAAAGG CGGTAACATT AATGTCCGTG CTGCCACTAT TCGAAACCAA
1201 GGTAAACTTT CTGCTGATTC TGTAAGCAAA GATAAAAGCG GCAATATTGT
1251 TCTTTCCGCC AAAGAGGGTG AAGCGGAAAT TGGCGGTGTA ATTTCCGCTC
1301 AAAATCAGCA AGCTAAAGGC GGCAAGCTGA TGATTACAGG CGATAAAGTC
1351 ACATTAAAAA CAGGTGCAGT TATCGACCTT TCAGGTAAAG AAGGGGAGA
1401 AACTTACCTT GGCGGTGACG AGCGCGGCGA AGGTAAAAAC GGCATTCAAT
1451 TAGCAAAGAA AACCTCTTTA GAAAAAGGCT CAACCATCAA TGTATCAGGC
1501 AAAGAAAAAG GCGGACGCGC TATTGTGTGG GGCGATATTG CGTTAATTGA
```

FIG. 3C.

```
1551 CGGCAATATT AACGCTCAAG GTAGTGGTGA TATCGCTAAA ACCGGTGGTT
1601 TTGTGGAGAC ATCGGGGCAT TATTATCCA TTGACAGCAA TGCAATTGTT
1651 AAAACAAAAG AGTGGTTGCT AGACCCTGAT GATGTAACAA TTGAAGCCGA
1701 AGACCCCTT CGCAATAATA CCGGTATAAA TGATGAATTC CCAACAGGCA
1751 CCGGTGAAGC AAGCGACCCT AAAAAAAATA GCGAACTCAA AACAACGCTA
1801 ACCAATACAA CTATTTCAAATTATCTGAAA AACGCCTGGA CAATGAATAT
1851 AACGGCATCA AGAAAACTTA CCGTTAATAG CTCAATCAAC ATCGGAAGCA
1901 ACTCCCACTT AATTCTCCAT AGTAAAGGTC AGCGTGGCGG AGGCGTTCAG
1951 ATTGATGGAG ATATTACTTC TAAAGGCGGA AATTTAACCA TTTATTCTGG
2001 CGGATGGGTT GATGTTCATA AAAATATTAC GCTTGATCAG GGTTTTTAA
2051 ATATTACCGC CGCTTCCGTA GCTTTTGAAG GTGGAAATAA CAAAGCACGC
2101 GACGCGGCAA ATGCTAAAAT TGTCGCCCAG GGCACTGTAA CCATTACAGG
2151 AGAGGGAAAA GATTTCAGGG CTAACAACGT ATCTTTAAAC GGAACGGGTA
2201 AAGGTCTGAA TATCATTTCA TCAGTGAATA ATTTAACCCA CAATCTTAGT
2251 GGCACAATTA ACATATCTGG GAATATAACA ATTAACCAAA CTACGAGAAA
2301 GAACACCTCG TATTGGCAAA CCAGCCATGA TTCGCACTGG AACGTCAGTG
2351 CTCTTAATCT AGAGACAGGC GCAAATTTTA CCTTTATTAA ATACATTTCA
```

FIG. 3D.

```
2401 AGCAATAGCA AAGGCTTAAC AACACAGTAT AGAAGCTCTG CAGGGGTGAA
2451 TTTTAACGGC GTAAATGGCA ACATGTCATT CAATCTCAAA GAAGGAGCGA
2501 AAGTTAATTT CAAATTAAAA CCAAACGAGA ACATGAACAC AAGCAAACCT
2551 TTACCAATTC GGTTTTTAGC CAATATCACA GCCACTGGTG GGGGCTCTGT
2601 TTTTTTTGAT ATATATGCCA ACCATTCTGG CAGAGGGGCT GAGTTAAAAA
2651 TGAGTGAAAT TAATATCTCT AACGGCGCTA ATTTTACCTT AAATTCCCAT
2701 GTTCGCGGCG ATGACGCTTT TAAAATCAAC AAAGACTTAA CCATAAATGC
2751 AACCAATTCA AATTTCAGCC TCAGACAGAC GAAAGATGAT TTTTATGACG
2801 GGTACGCACG CAATGCCATC AATTCAACCT ACAACATATC CATTCTGGGC
2851 GGTAATGTCA CCCTTGGTGG ACAAAACTCA AGCAGCAGCA TTACGGGGAA
2901 TATTACTATC GAGAAAGCAG CAAATGTTAC GCTAGAAGCC AATAACGCCC
2951 CTAATCAGCA AAACATAAGG GATAGAGTTA TAAAACTTGG CAGCTTGCTC
3001 GTTAATGGGA GTTTAAGTTT AACTGGCGAA AATGCAGATA TTAAAGGCAA
3051 TCTCACTATT TCAGAAAGCG CCACTTTTAA AGGAAAGACT AGAGATACCC
3101 TAAATATCAC CGGCAATTTT ACCAATAATG GCACTGCCGA AATTAATATA
3151 ACACAAGGAG TGGTAAAACT TGGCAATGTT ACCAATGATG GTGATTTAAA
```

FIG. 3E.

```
3201  CATTACCACT  CACGCTAAAC  GCAACCAAAG  AAGCATCATC  GGCGGAGATA
3251  TAATCAACAA  AAAAGGAAGC  TTAAATATTA  CAGACAGTAA  TAATGATGCT
3301  GAAATCCAAA  TTGGCGGCAA  TATCTCGCAA  AAAGAAGGCA  ACCTCACGAT
3351  TTCTTCCGAT  AAAATTAATA  TCACCAAAACA  GATAACAATC  AAAAAGGGTA
3401  TTGATGGAGA  GGACTCTAGT  TCAGATGCGA  CAAGTAATGC  CAACCTAACT
3451  ATTAAAACCA  AAGAATTGAA  ATTGACAGAA  GACCTAAGTA  TTTCAGGTTT
3501  CAATAAAGCA  GAGATTACAG  CCAAAGATGG  TAGAGATTTA  ACTATTGGCA
3551  ACAGTAATGA  CGGTAACAGC  GGTGCCGAAG  CCAAAAACAGT  AACTTTTAAC
3601  AATGTTAAAG  ATTCAAAAAT  CTCTGCTGAC  GGTCACAATG  TGACACTAAA
3651  TAGCAAAGTG  AAAACATCTA  GCAGCAATGG  CGGACGTGAA  AGCAATAGCG
3701  ACAACGATAC  CGGCTTAACT  ATTACTGCAA  AAAATGTAGA  AGTAAACAAA
3751  GATATTACTT  CTCTCAAAAC  AGTAAATATC  ACCGCGTCGG  AAAAGGTTAC
3801  CACCACAGCA  GGCTCGACCA  TTAACGCAAC  AAATGGCAAA  GCAAGTATTA
3851  CAACCAAAAC  AGGTGATATC  AGCGGTACGA  TTTCCGGTAA  CACGGTAAGT
3901  GTTAGCGCGA  CTGGTGATTT  AACCACTAAA  TCCGGCTCAA  AAATTGAAGC
3951  GAAATCGGGT  GAGGCTAATG  AACAGGTACA  TAACAAGTGC  ATTGGCGGTA
```

FIG. 3F.

```
4001 CAATTTCCGG TAATACGGTA AATGTTACGG CAAACGCTGG CGATTTAACA
4051 GTTGGGAATG GCGCAGAAAT TAATGCGACA GAAGGAGCTG CAACCTTAAC
4101 CGCAACAGGG AATACCTTGA CTACTGAAGC CGGTTCTAGC ATCACTTCAA
4151 CTAAGGGTCA GGTAGACCTC TTGGCTCAGA ATGGTAGCAT CGCAGGAAGC
4201 ATTAATGCTG CTAATGTGAC ATTAAATACT ACAGGCACCT TAACCACCGT
4251 GGCAGGCTCG GATATTAAAG CAACCAGCGG CACCTTGGTT ATTAACGCAA
4301 AAGATGCTAA GCTAAATGGT GATGCATCAG GTGATAGTAC AGAAGTGAAT
4351 GCAGTCAACG CAAGCGGCTC TGGTAGTGTG ACTGCGGCAA CCTCAAGCAG
4401 TGTGAATATC ACTGGGGATT TAAACACAGT AAATGGGTTA AATATCATTT
4451 CGAAAGATGG TAGAAACACT GTGCGCTTAA GAGGCAAGGA AATTGAGGTG
4501 AAATATATCC AGCCAGGTGT AGCAAGTGTA GAAGAAGTAA TTGAAGCGAA
4551 ACGGTCCTT GAAAAAGTAA AAGATTATC TGATGAAGAA AGAGAAACAT
4601 TAGCTAAACT TGGTGTAAGT GCTGTACGTT TTGTTGAGCC AAATAATACA
4651 ATTACAGTCA ATACACAAAA TGAATTTACA ACCAGACCGT CAAGTCAAGT
4701 GATAATTTCT GAAGGTAAGG CGTGTTTCTC AAGTGGTAAT GGCGCACGAG
4751 TATGTACCAA TGTTGCTGAC GATGGACAGC CGTAGTCAGT AATTGACAAG
4801 GTAGATTTCA TCCTGCAATG AAGTCATTTT ATTTTCGTAT TATTTACTGT
```

FIG. 3G.

```
4851  GTGGGTTAAA GTTCAGTACG GGCTTTACCC ATCTTGTAAA AAATTACGGA
4901  GAATACAATA AAGTATTTTT AACAGGTTAT TATTATG
```

FIG. 4A. AMINO ACID SEQUENCE OF HIGH MOLECULAR WEIGHT
PROTEIN 2

```
  1  MNKIYRLKFS KRLNALVAVS ELARGCDHST EKGSEKPARM KVRHLALKPL
 51  SAMLLSLGVT SIPQSVLASG LQGMDVVHGT ATMQVDGNKT IIRNSVDAII
101  NWKQFNIDQN EMVQFLQENN NSAVFNRVTS NQISQLKGIL DSNGQVFLIN
151  PNGITIGKDA IINTNGFTAS TLDISNENIK ARNFTFEQTK DKALAEIVNH
201  GLITVGKDGS VNLIGGKVKN EGVISVNGGS ISLLAGQKIT ISDIINPTIT
251  YSIAAPENEA VNLGDIFAKG GNINVRAATI RNQGKLSADS VSKDKSGNIV
301  LSAKEGEAEI GGVISAQNQQ AKGGKLMITG DKVTLKTGAV IDLSGKEGGE
351  TYLGGDERGE GKNGIQLAKK TSLEKGSTIN VSGKEKGGRA IVWGDIALID
401  GNINAQGSGD IAKTGGFVET SGHDLFIKDN AIVDAKEWLL DFDNVSINAE
451  DPLRNNTGIN DEFPTGTGEA SDPKKNSELK TTLTNTTISN YLKNAWTMNI
501  TASRKLTVNS SINIGSNSHL ILHSKGQRGG GVQIDGDITS KGGNLTIYSG
551  GWVDVHKNIT LDQGFLNITA ASVAFEGGNN KARDAANAKI VAQGTVTITG
601  EGKDFRANNV SLNGTGKGLN IISSVNNLTH NLSGTINISG NITINQTTRK
651  NTSYWQTSHD SHWNVSALNL ETGANFTFIK YISSNSKGLT TQYRSSAGVN
701  FNGVNGNMSF NLKEGAKVNF KLKPNENMNT SKPLPIRFLA NITATGGGSV
```

FIG. 4B.

```
 751  FFDIYANHSG  RGAELKMSEI  NISNGANFTL  NSHVRGDDAF  KINKDLTINA
 801  TNSNFSLRQT  KDDFYDGYAR  NAINSTYNIS  ILGGNVTLGG  QNSSSSITGN
 851  ITIEKAANVT  LEANNAPNQQ  NIRDRVIKLG  SLLVNGSLSL  TGENADIKGN
 901  LTISESATFK  GKTRDTLNIT  GNFTNNGTAE  INITQGVVKL  GNVTNDGDLN
 951  ITTHAKRNQR  SIIGGDIINK  KGSLNITDSN  NDAEIQIGGN  ISQKEGNLTI
1001  SSDKINITKQ  ITIKKGIDGE  DSSSDATSNA  NLTIKTKELK  LTEDLSISGF
1051  NKAEITAKDG  RDLTIGNSND  GNSGAEAKTV  TFNNVKDSKI  SADGHNVTLN
1101  SKVKTSSSNG  GRESNSDNDT  GLTITAKNVE  VNKDITSLKT  VNITASEKVT
1151  TTAGSTINAT  NGKASITTKT  GDISGTISGN  TVSVSATVDL  TTKSGSKIEA
1201  KSGEANVTSA  TGTIGGTISG  NTVNVTANAG  DLTVGNGAEI  NATEGAATLT
1251  ATGNTLTTEA  GSSITSTKGQ  VDLLAQNGSI  AGSINAANVT  LNTTGTLTTV
1301  AGSDIKATSG  TLVINAKDAK  LNGDASGDST  EVNAVNASGS  GSVTAATSSS
1351  VNITGDLNTV  NGLNIISKDG  RNTVRLRGKE  IEVKYIQPGV  ASVEEVIEAK
1401  RVLEKVKDLS  DEERETLAKL  GVSAVRFVEP  NNTITVNTQN  EFTTRPSSQV
1451  IISEGKACFS  SGNGARVCTN  VADDGQP
```

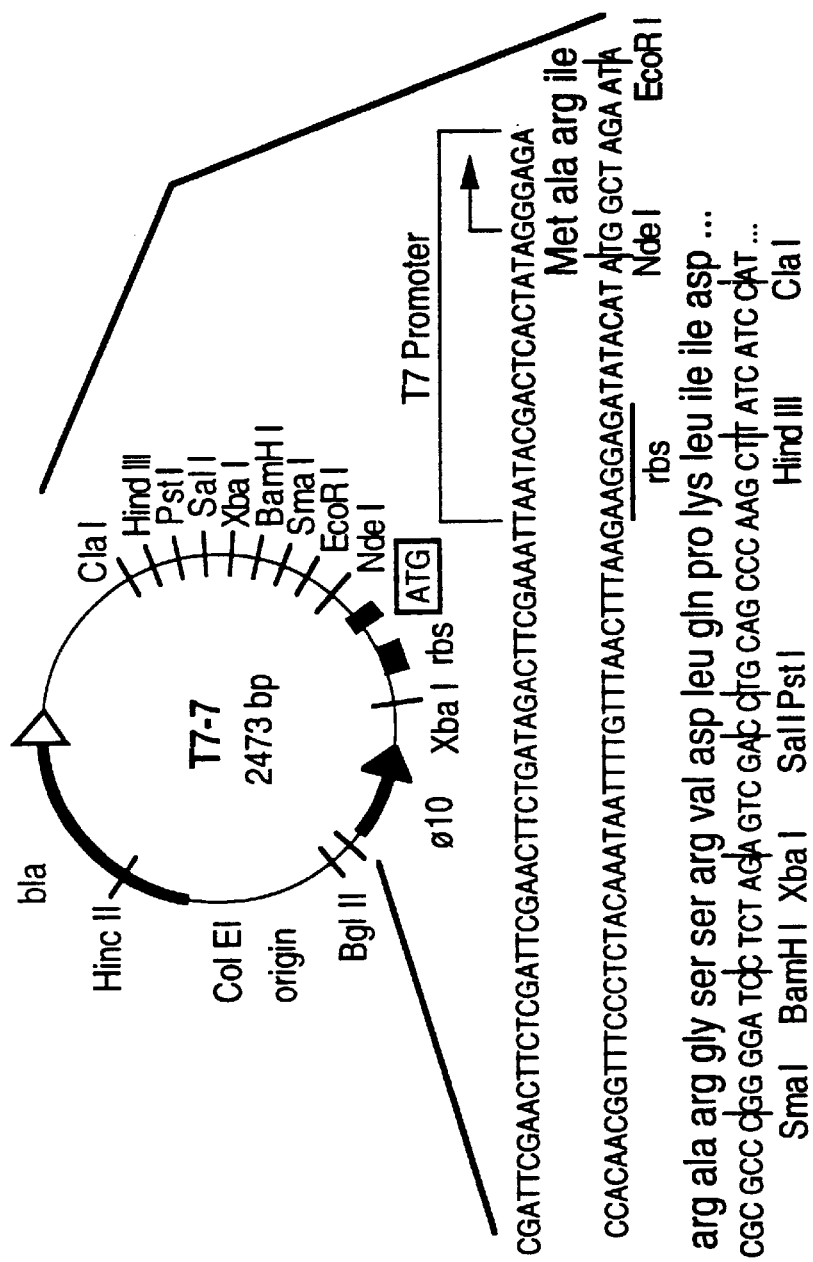

FIG. 5B.

(A) Partial restriction maps of representative HMW1 and HMW2 recombinant phage and of HMW1 plasmid subclones. The shaded boxes indicate the locations of the structural genes. In the recombinant phage, transcription proceeds from left to right for the HMW1 gene and from right to left for the HMW2 gene. The methods used for construction of the plasmids shown are described in the text. (B) Restriction map of the T7 expression vector pT7-7. This vector contains the T7 RNA polymerase promoter φ10, a ribosome - binding site (rbs), and the translational start site for the T7 gene 10 protein upstream from a multiple cloning site (37).

FIG. 6A.

```
  1  ACAGCGTTCT CTTAATACTA GTACAAACCC ACAATAAAAT ATGACAAACA
 51  ACAATTACAA CACCTTTTTT GCAGTCTATA TGCAAATATT TTAAAAAATA
101  GTATAAATCC GCCATATAAA ATGGTATAAT CTTTCATCTT TCATCTTTCA
151  TCTTTCATCT TTCATCTTTC ATCTTTCATC TTTCATCTTT CATCTTTCAT
201  CTTTCATCTT TCATCTTTCA TCTTTCATCT TTCATCTTTC ACATGAAATG
251  ATGAACCGAG GGAAGGGAGG GAGGGGCAAG AATGAAGAGG GAGCTGAACG
301  AACGCAAATG ATAAAGTAAT TTAATTGTTC AACTAACCTT AGGAGAAAAT
351  ATGAACAAGA TATATCGTCT CAAATTCAGC AAACGCCTGA ATGCTTTGGT
401  TGCTGTGTCT GAATTGGCAC GGGGTTGTGA CCATTCCACA GAAAAAGGCA
451  GCGAAAAACC TGCTCGCATG AAAGTGCGTC ACTTAGCGTT AAAGCCACTT
501  TCCGCTATGT TACTATCTTT AGGTGTAACA TCTATTCCAC AATCTGTTTT
551  AGCAAGCGGC TTACAAGGAA TGGATGTAGT ACACGGCACA GCCACTATGC
601  AAGTAGATGG TAATAAAACC ATTATCCGCA ACAGTGTTGA CGCTATCATT
651  AATTGGAAAC AATTTAACAT CGACCAAAAT GAAATGGTGC AGTTTTTACA
701  AGAAAACAAC AACTCCGCCG TATTCAACCG TGTTACATCT AACCAAATCT
751  CCCAATTAAA AGGGATTTTA GATTCTAACG GACAAGTCTT TTTAATCAAC
```

FIG. 6B.

```
 801  CCAAATGGTA TCACAATAGG TAAAGACGCA ATTATTAACA CTAATGCTT
 851  TACGGCTTCT ACGCTAGACA TTTCTAACGA AAACATCAAG GCGGTAATT
 901  TCACCTTCGA GCAAACCAAA GATAAAGCGC TCGCTGAAAT TGTGAATCAC
 951  GGTTTAATTA CTGTCGGTAA AGACGGCAGT GTAAATCTTA TTGGTGGCAA
1001  AGTGAAAAAC GAGGGTGTGA TTAGCGTAAA TGGTGGCAGC ATTTCTTTAC
1051  TCGCAGGGCA AAAAATCACC ATCAGCGATA TAATAAACCC AACCATTACT
1101  TACAGCATTG CCGCGCCTGA AAATGAAGCG GTCAATCTGG GCGATATTTT
1151  TGCCAAAGGC GGTAACATTA ATGTCCGTGC TGCCACTATT CGAAACCAAG
1201  CTTTCCGCCA AAGAGGGTGA AGCGGAAATT GGCGGTGTAA TTTCCGCTCA
1301  AAATCAGCAA GCTAAAGGCG GCAAGCTGAT GATTACAGGC GATAAAGTCA
1351  CATTAAAAAC AGGTGCAGTT ATCGACCTTT CAGGTAAAGA AGGGGAGAA
1401  ACTTACCTTG GCGGTGACGA GCGCGGCGAA GGTAAAAACG GCATTCAATT
1451  AGCAAAGAAA ACCTCTTTAG AAAAAGGCTC AACCATCAAT GTATCAGGCA
1501  AAGAAAAAGG CGGACGCGCT ATTGTGTGGG GCGATATTGC GTTAATTGAC
1551  GGCAATATTA ACGCTCAAGG TAGTGGTGAT ATCGCTAAAA CCGGTGGTTT
1601  TGTGGAGACG TCGGGGCATG ATTTATTCAT CAAAGACAAT GCAATTGTTG
```

FIG. 6C.

```
1651  ACGCCAAAGA GTGGTTGTTA GACCCGGATA ATGTATCTAT TAATGCAGAA
1701  ACAGCAGGAC GCAGCAATAC TTCAGAAGAC GATGAATACA CGGGATCCGG
1751  GAATAGTGCC AGCACCCCAA AACGAAACAA AGAAAAGACA ACATTAACAA
1801  ACACAACTCT TGAGAGTATA CTAAAAAAAG GTACCTTTGT TAACATCACT
1851  GCTAATCAAC GCATCTATGT CAATAGCTCC ATTAATTTAT CCAATGGCAG
1901  CTTAACTCTT TGGAGTGAGG GTCGGAGCGG TGGCGGCGTT GAGATTAACA
1951  ACGATATTAC CACCGGTGAT GATACCAGAG GTGCAAACTT AACAATTTAC
2001  TCAGGCGGCT GGGTTGATGT TCATAAAAAT ATCTCACTCG GGGCGCAAGG
2051  TAACATAAAC ATTACAGCTA AACAAGATAT CGCCTTTGAG AAAGGAAGCA
2101  ACCAAGTCAT TACAGGTCAA GGGACTATTA CCTCAGGCAA TCAAAAAGGT
2151  TTTAGATTTA ATAATGTCTC TCTAAACGGC ACTGGCAGCG GACTGCAATT
2201  CACCACTAAA AGAACCAATA AATACGCTAT CACAAATAAA TTTGAAGGGA
2251  CTTTAAATAT TTCAGGGAAA GTGAACATCT CAATGGTTTT ACCTAAAAAT
2301  GAAAGTGGAT ATGATAAATT CAAAGGACGC ACTTACTGGA ATTAACCTC
2351  GAAAGTGGAT ATGATAAATT CAAAGGACGC CCTCACTATT GACTCCAGAG
2401  GAAGCGATAG TGCAGGCACA CTTACCCAGC CTTATAATTT AAACGGTATA
2451  TCATTCAACA AAGACACTAC CTTTAATGTT GAACGAAATG CAAGAGTCAA
```

FIG. 6D.

```
2501  CTTTGACATC  AAGGCACCAA  TAGGGATAAA  TAAGTATTCT  AGTTTGAATT
2551  ACGCATCATT  TAATGGAAAC  ATTTCAGTTT  CGGGAGGGGG  GAGTGTTGAT
2601  TTCACACTTC  TCGCCTCATC  CTCTAACGTC  CAAACCCCCG  GTGTAGTTAT
2651  AAATTCTAAA  TACTTTAATG  TTTCAACAGG  GTCAAGTTTA  AGATTTAAAA
2701  CTTCAGGCTC  AACAAAAACT  GGCTTCTCAA  TAGAGAAAGA  TTTAACTTTA
2751  AATGCCACCG  GAGGCAACAT  AACACTTTTG  CAAGTTGAAG  GCACCGATGG
2801  AATGATTGGT  AAAGGCATTG  TAGCCAAAAA  AAACATAACC  TTTGAAGGAG
2851  GTAAGATGAG  GTTTGGCTCC  AGGAAAGCCG  TAACAGAAAT  CGAAGGCAAT
2901  GTTACTATCA  ATAACAACGC  TAACGTCACT  CTTATCGGTT  CGGATTTTGA
2951  CAACCATCAA  AAACCTTTAA  CTATTAAAAA  AGATGTCATC  ATTAATAGCG
3001  GCAACCTTAC  CGCTGGAGGC  AATATTGTCA  ATATAGCCGG  AAATCTTACC
3051  GTTGAAAGTA  ACGCTAATTT  CAAAGCTATC  ACAAATTTCA  CTTTTAATGT
3101  AGCGGGCTTG  TTTGACAACA  AAGGCAATTC  AAATATTTCC  ATTGCCAAAG
3151  GAGGGGCTCG  CTTTAAAGAC  ATTGATAATT  CCAAGAATTT  AAGCATCACC
3201  ACCAACTCCA  GCTCCACTTA  CCGCACTATT  ATAAGCGGCA  ATATAACCAA
3251  TAAAAACGGT  GATTTAAATA  TTACGAACGA  AGGTAGTGAT  ACTGAAATGC
```

FIG. 6E.

```
3301  AAATTGGCGG  CGATGTCTCG  CAAAAGAAG   GTAATCTCAC  GATTCTTCT
3351  GACAAAATCA  ATATTACCAA  ACAGATAACA  ATCAAGGCAG  GTGTTGATGG
3401  GGAGAATTCC  GATTCAGACG  CGACAAACAA  TGCCAATCTA  ACCATTAAAA
3451  CCAAAGAATT  GAAATTAACG  CAAGACCTAA  ATATTTCAGG  TTTCAATAAA
3501  GCAGAGATTA  CAGCTAAAGA  TGGTAGTGAT  TTAACTATTG  GTAACACCAA
3551  TAGTGCTGAT  GGTACTAATG  CCAAAAAAGT  AACCTTTAAC  CAGGTTAAAG
3601  ATTCAAAAAT  CTCTGCTGAC  GGTCACAAGG  TGACACTACA  CAGCAAAGTG
3651  GAAACATCCG  GTAGTAATAA  CAACACTGAA  GATAGCAGTG  ACAATAATGC
3701  CGGCTTAACT  ATCGATGCAA  AAAATGTAAC  AGTAAACAAC  AATATTACTT
3751  CTCACAAAGC  AGTGAGCATC  TCTGCGACAA  GTGGAGAAAT  TACCACTAAA
3801  ACAGGTACAA  CCATTAAACGC AACCACTGGT  AACGTGGAGA  TAACCGCTCA
3851  AACAGGTAGT  ATCCTAGGTG  GAATTGAGTC  CAGCTCTGGC  TCTGTAACAC
3901  TTACTGCAAC  CGAGGGCGCT  CTTGCTGTAA  GCAATATTTC  GGGCAACACC
3951  GTTACTGTTA  CTGCAAATAG  CGGTGCATTA  ACCACTTTGG  CAGGCTCTAC
4001  AATTAAAGGA  ACCGAGAGTG  TAACCACTTC  AAGTCAATCA  GGCGATATCG
4051  GCGGTACGAT  TTCTGGTGGC  ACAGTAGAGG  TTAAAGCAAC  CGAAAGTTTA
```

FIG. 6F.

```
4101 ACCACTCAAT CCAATTCAAA AATTAAAGCA ACAACAGGCG AGGCTAACGT
4151 AACAAGTGCA ACAGGTACAA TTGGTGGTAC GATTTCCGGT AATACGGTAA
4201 ATGTTACGGC AAACGCTGGC GATTTAACAG TTGGGAATGG CGCAGAAATT
4251 AATGCGACAG AAGGAGCTGC AACCTTAACT ACATCATCGG GCAAATTAAC
4301 TACCGAAGCT AGTTCACACA TTACTTCAGC CAAGGGTCAG GTAAATCTTT
4351 CAGCTCAGGA TGGTAGCCGT GCAGGAAGTA TTAATGCCGC CAATGTGACA
4401 CTAAATACTA CAGGCACTTT AACTACCGTG AAGGGTTCAA ACATTAATGC
4451 AACCAGCGGT ACCTTGGTTA TTAACGCAAA AGACGCTGAG CTAAATGGCG
4501 CAGCATTGGG TAACCACACA GTGGTAAATG CAACCAACGC AAATGGCTCC
4551 GGCAGCGTAA TCGCGACAAC CTCAAGCAGA GTGAACATCA CTGGGGATTT
4601 AATCACAATA AATGGATTAA ATATCATTTC AAAAAACGGT ATAAACACCG
4651 TACTGTTAAA AGGCGTAAA ATTGATGTGA AATACATTCA ACCGGGTATA
4701 GCAAGCGTAG ATGAAGTAAT TGAAGCGAAA CGCATCCTTG AGAAGGTAAA
4751 AGATTTATCT GATGAAGAAA GAGAAGCGTT AGCTAAACTT GGCGTAAGTG
4801 CTGTACGTTT TATTGAGCCA AATAATACAA TTACAGTCGA TACACAAAAT
4851 GAATTTGCAA CCAGACCATT AAGTCGAATA GTGATTTCTG AAGGCAGGGC
4901 GTGTTTCTCA AACAGTGATG GCGCGACGGT GTGCGTTAAT ATCGCTGATA
```

FIG. 6G.

```
4951 ACGGGCGGTA GCGGTCAGTA ATTGACAAGG TAGATTTCAT CCTGCAATGA
5001 AGTCATTTTA TTTTCGTATT ATTTACTGTG TGGGTTAAAG TTCAGTACGG
5051 GCTTTACCCA TCTTGTAAAA AATTACGGAG AATACAATAA AGTATTTTTA
5101 ACAGGTTATT ATTATGAAAA ATATAAAAAG CAGATTAAAA CTCAGTGCAA
5151 TATCAGTATT GCTTGGCCTG GCTTCTTCAT CATTGTATGC AGAAGAAGCG
5201 TTTTTAGTAA AAGGCTTTCA GTTATCTGGT GCACTTGAAA CTTTAAGTGA
5251 AGACGCCCAA CTGTCTGTAG CAAAATCTTT ATCTAAATAC CAAGGCTCGC
5301 AAACTTTAAC AAACCTAAAA ACAGCACAGC TTGAATTACA GGCTGTGCTA
5351 GATAAGATTG AGCCAAATAA GTTTGATGTG ATATTGCCAC AACAAACCAT
5401 TACGGATGGC AATATTATGT TTGAGCTAGT CTCGAAATCA GCCGCAGAAA
5451 GCCAAGTTTT TTATAAGGCG AGCCAGGGTT ATAGTGAAGA AATATCGCT
5501 CGTAGCCTGC CATCTTTGAA ACAAGGAAAA GTGTATGAAG ATGGTCGTCA
5551 GTGGTTCGAT TTGCGTGAAT TCAATATGGC AAAAGAAAAT CCACTTAAAG
5601 TCACTCGCGT GCATTACGAG TTAAACCCTA AAAACAAAAC CTCTGATTTG
5651 GTAGTTGCAG GTTTTCGCC TTTGGCAAA ACGCGTAGCT TTGTTCCTA
5701 TGATAATTTC GGCGCAAGGG AGTTTAACTA TCAACGTGTA AGTCTAGGTT
```

FIG. 6H.

```
5751  TTGTAAATGC  CAATTTGACC  GGACATGATG  ATGTATTAAA  TCTAAACGCA
5801  TTGACCAATG  TAAAAGCACC  ATCAAAATCT  TATGCGGTAG  GCATAGGATA
5851  TACTTATCCG  TTTTATGATA  AACACCAATC  CTTAAGTCTT  TATACCAGCA
5901  TGAGTTATGC  TGATTCTAAT  GATATCGACG  GCTTACCAAG  TGCGATTAAT
5951  CGTAAATTAT  CAAAAGGTCA  ATCTATCTCT  GCGAATCTGA  AATGGAGTTA
6001  TTATCTCCCG  ACATTTAACC  TTGGAATGGA  AGACCAGTTT  AAAATTAATT
6051  TAGGCTACAA  CTACCGCCAT  ATTAATCAAA  CATCCGAGTT  AAACACCCTG
6101  GGTGCAACGA  AGAAAAAATT  TGCAGTATCA  GGCGTAAGTG  CAGGCATTGA
6151  TGGACATATC  CAATTTACCC  CTAAAACAAT  CTTTAATATT  GATTTAACTC
6201  ATCATTATTA  CGCGAGTAAA  TTACCAGGCT  CTTTTGGAAT  GGAGCGCATT
6251  GGCGAAACAT  TTAATCGCAG  CTATCACATT  AGCACAGCCA  GTTTAGGGTT
6301  GAGTCAAGAG  TTTGCTCAAG  GTTGGCATTT  TAGCAGTCAA  TTATCGGGTC
6351  AGTTTACTCT  ACAAGATATA  AGTAGCATAG  ATTTATTCTC  TGTAACAGGT
6401  ACTTATGGCG  TCAGAGGCTT  TAAATACGGC  GGTGCAAGTG  GTGAGCGCGG
6451  TCTTGTATGG  CGTAATGAAT  TAAGTATGCC  AAAATACACC  CGCTTTCAAA
6501  TCAGCCCTTA  TGCGTTTTAT  GATGCAGGTC  AGTTCCGTTA  TAATAGCGAA
6551  AATGCTAAAA  CTTACGGCGA  AGATATGCAC  ACGGTATCCT  CTGCGGGTTT
```

FIG. 6I.

```
6601  AGGCATTAAA  ACCTCTCCTA  CACAAAACTT  AAGCTTAGAT  GCTTTGTTG
6651  CTCGTCGCTT  TGCAAATGCC  AATAGTGACA  ATTTGAATGG  CAACAAAAAA
6701  CGCACAAGCT  CACCTACAAC  CTTCTGGGGT  AGATTAACAT  TCAGTTCTA
6751  ACCCTGAAAT  TTAATCAACT  GGTAAGCGTT  CCGCCTACCA  GTTTATAACT
6801  ATATGCTTTA  CCCGCCAATT  TACAGTCTAT  ACGCAACCCT  GTTTTCATCC
6851  TTATATATCA  AACAAACTAA  GCAAACCAAG  CAAACCAAGC  AAACCAAGCA
6901  AACCAAGCAA  ACCAAGCAAA  CCAAGCAAAC  CAAGCAAACC  AAGCAAACCA
6951  AGCAAACCAA  GCAAACCAAG  CAAACCAAGC  AAACCAAGCA  ATGCTAAAAA
7001  ACAATTTATA  TGATAAACTA  AAACATACTC  CATACCATGG  CAATACAAGG
7051  GATTTAATAA  TATGACAAAA  GAAAATTTAC  AAAGTGTTCC  ACAAAATACG
7101  ACCGCTTCAC  TTGTAGAATC  AAACAACGAC  CAAACTTCCC  TGCAAATACT
7151  TAAACAACCA  CCCAAACCCA  ACCTATTACG  CCTGGAACAA  CATGTCGCCA
7201  AAAAGATTA  TGAGCTTGCT  TGCCGGAAT  TAATGGCGAT  TTTGGAAAAA
7251  ATGGACGCTA  ATTTTGGAGG  CGTTCACGAT  ATTGAATTTG  ACGCACCTGC
7301  TCAGCTGGCA  TATCTACCCG  AAAAACTACT  AATTCATTTT  GCCACTCGTC
7351  TCGCTAATGC  AATTACAACA  CTCTTTTCCG  ACCCCGAATT  GGCAATTTCC
```

FIG. 6J.

```
7401  GAAGAAGGGG  CATTAAAGAT  GATTAGCCTG  CAACGCTGGT  TGACGCTGAT
7451  TTTGCCTCT   TCCCCCTACG  TTAACGCAGA  CCATATTCTC  AATAAATATA
7501  ATATCAACCC  AGATTCCGAA  GGTGGCTTTC  ATTTAGCAAC  AGACAACTCT
7551  TCTATTGCTA  AATTCTGTAT  TTTTTACTTA  CCCGAATCCA  ATGTCAATAT
7601  GAGTTTAGAT  GCGTTATGGG  CAGGGAATCA  ACAACTTTGT  GCTTCATTGT
7651  GTTTTGCGTT  GCAGTCTTCA  CGTTTTATTG  GTACTGCATC  TGCGTTTCAT
7701  AAAAGAGCGG  TGGTTTTACA  GTGGTTCCT   AAAAAACTCG  CCGAAATTGC
7751  TAATTTAGAT  GAATTGCCTG  CAAATATCCT  TCATGATGTA  TATATGCACT
7801  GCAGTTATGA  TTTAGCAAAA  AACAAGCACG  ATGTTAAGCG  TCCATTAAAC
7851  GAACTTGTCC  GCAAGCATAT  CCTCACGCAA  GGATGGCAAG  ACCGCTACCT
7901  TTACACCTTA  GGTAAAAAGG  ACGGCAAACC  TGTGATGATG  GTACTGCTTG
7951  AACATTTTAA  TTCGGGACAT  TCGATTTATC  GCACGCATTC  AACTTCAATG
8001  ATTGCTGCTC  GAGAAAAATT  CTATTTAGTC  GGCTTAGGCC  ATGAGGGCGT
8051  TGATAACATA  GGTCGAGAAG  TGTTTGACGA  GTTCTTTGAA  ATCAGTAGCA
8101  ATAATATAAT  GGAGAGACTG  TTTTTTATCC  GTAAACAGTG  CGAAACTTTC
8151  CAACCCGCAG  TGTTCTATAT  GCCAAGCATT  GGCATGGATA  TTACCACGAT
```

FIG. 6K.

```
8201  TTTGTGAGC AACACTCGGC TTGCCCCTAT TCAAGCTGTA GCCTTGGGTC
8251  ATCCTGCCAC TACGCATTCT GAATTTATTG ATTATGTCAT CGTAGAAGAT
8301  GATTATGTGG GCAGTGAAGA TTGTTTAGC  GAAACCCTTT TACGCTTACC
8351  CAAAGATGCC CTACCTTATG TACCATCTGC ACTCGCCCCA CAAAAAGTGG
8401  ATTATGTACT CAGGGAAAAC CCTGAAGTAG TCAATATCGG TATTGCCGCT
8451  ACCACAATGA AATTAAACCC TGAATTTTTG CTAACATTGC AAGAAATCAG
8501  AGATAAAGCT AAAGTCAAAA TACATTTTCA TTTCGCACTT GGACAATCAA
8551  CAGGCTTGAC ACACCCTTAT GTCAAATGGT TTATCGAAAG CTATTTAGGT
8601  GACGATGCCA CTGCACATCC CCACGCACCT TATCACGATT ATCTGGCAAT
8651  ATTGCGTGAT TGCGATATGC TACTAAATCC GTTTCCTTTC GGTAATACTA
8701  ACGGCATAAT TGATATGGTT ACATTAGGTT TAGTTGGTGT ATGCAAAACG
8751  GGGGATGAAG TACATGAACA TATTGATGAA GGTCTGTTTA AACGCTTAGG
8801  ACTACCAGAA TGGCTGATAG CCGACACACG AGAAACATAT ATTGAATGTG
8851  CTTTGCGTCT AGCAGAAAAC CATCAAGAAC GCCTTGAACT CCGTCGTTAC
8901  ATCATAGAAA ACAAAGGCTT ACAAAAGCTT TTTACAGGCG ACCCTCGTCC
8951  ATTGGGCAAA ATACTGCTTA AGAAAACAAA TGAATGGAAG CGGAAGCACT
9001  TGAGTAAAAA ATAACGGTTT TTTAAAGTAA AAGTGCGGTT AATTTTCAAA
```

FIG. 6L.

```
9051  GCGTTTTAAA AACCTCTCAA AAATCAACCG CACTTTTATC TTTATAACGC
9101  TCCCGCGCGC TGACAGTTTA TCTCTTTCTT AAAATACCCA TAAAATTGTG
9151  GCAATAGTTG GGTAATCAAA TTCAATTGTT GATACGGCAA ACTAAAGACG
9201  GCGCGTTCTT CGGCAGTCAT C
```

FIG. 7A.

```
  1  CGCCACTTCA ATTTTGGATT GTTGAAATTC AACTAACCAA AAAGTGCGGT
 51  TAAAATCTGT GGAGAAAATA GGTTGTAGTG AAGAACGAGG TAATTGTTCA
101  AAAGGATAAA GCTCTCTTAA TTGGGCATTG GTTGGCGTTT CTTTTTCGGT
151  TAATAGTAAA TTATATTCTG GACGACTATG CAATCCACCA ACAACTTTAC
201  CGTTGGTTTT AAGCGTTAAT GTAAGTTCTT GCTCTTCTTG GCGAATACGT
251  AATCCCATTT TTTGTTTAGC AAGAAAATGA TCGGGATAAT CATAATAGGT
301  GTTGCCCAAA AATAAATTTT GATGTTCTAA AATCATAAAT TTTGCAAGAT
351  ATTGTGGCAA TTCAATACCT ATTGTGGCG AAATGCCAA ATCAACTGGT TAAATATACA
401  ATTTCTTGTA GCATAATATT TCCCACTCAA TCCCACTCAA ATCAACTGGT TAAATATACA
451  AGATAATAAA AATAAATCAA GATTTTTGTG ATGACAAACA ACAATTACAA
501  CACCTTTTTT GCAGTCTATA TGCAAATATT TTAAAAAAAT AGTATAAATC
551  CGCCATATAA AATGGTATAA TCTTTCATCT TTCATCTTTC ATCTTTCATC
601  TTTCATCTTT CATCTTTCAT CTTTCATCTT TCATCTTTCA TCTTTCATCT
651  TTCATCTTTC ATCTTTCATC TTTCATCTTT CACATGAAAT GATGAACCGA
701  GGGAAGGGAG GGAGGGGCAA GAATGAAGAG GGAGCTGAAC GAACGCAAAT
751  GATAAAGTAA TTTAATTGTT CAACTAACCT TAGGAGAAAA TATGAACAAG
```

FIG. 7B.

```
801   ATATATCGTC TCAAATTCAG CAAACGCCTG AATGCTTTGG TTGCTGTGTC
851   TGAATTGGCA CGGGGTTGTG ACCATTCCAC AGAAAAAGGC AGCGAAAAAC
901   CTGCTCGCAT GAAAGTGCGT CACTTAGCGT TAAAGCCACT TTCCGCTATG
951   TTACTATCTT TAGGTGTAAC ATCTATTCCA CAATCTGTTT TAGCAAGCGG
1001  CAATTTAACA TCGACCAAAA TGAAATGGTG CAGTTTTTAC AAGAAAACAA
1051  GTAATAAAAC CATTATCCGC AACAGTGTTG ACGCTATCAT TAATTGGAAA
1101  CAATTTAACA TCGACCAAAA TGAAATGGTG CAGTTTTTAC AAGAAAACAA
1151  CAACTCCGCC GTATTCAACC GTGTTACATC TAACCAAATC TCCCAATTAA
1201  AAGGGATTTT AGATTCTAAC GGACAAGTCT TTTTAATCAA CCCAAATGGT
1251  ATCACAATAG GTAAAGACGC AATTATTAAC ACTAATGGCT TTACGGCTTC
1301  TACGCTAGAC ATTTCTAACG AAAACATCAA GGCGCGTAAT TTCACCTTCG
1351  AGCAAACCAA AGATAAAGCG CTCGCTGAAA TTGTGAATCA CGGTTTAATT
1401  ACTGTCGGTA AAGACGGCAG TGTAAATCTT ATTGGTGGCA AAGTGAAAAA
1451  CGAGGGTGTG ATTAGCGTAA ATGGTGGCAG CATTCTTTTA CTCGCAGGGC
1501  AAAAAATCAC CATCAGCGAT ATAATAAACC CAACCATTAC TTACAGCATT
1551  GCCGCGCCTG AAAATGAAGC GGTCAATCTG GGCGATATTT TTGCCAAAGG
```

FIG. 7C.

```
1601  CGGTAACATT  AATGTCCGTG  CTGCCACTAT  TCGAAACCAA  GGTAAACTTT
1651  CTGCTGATTC  TGTAAGCAAA  GATAAAGCG   GCAATATTGT  TCTTTCCGCC
1701  AAAGAGGGTG  AAGCGGAAAT  TGGCGGTGTA  ATTCCGCTC   AAAATCAGCA
1751  AGCTAAAGGC  GGCAAGCTGA  TGATTACAGG  CGATAAAGTC  ACATTAAAAA
1801  CAGGTGCAGT  TATCGACCTT  TCAGGTAAAG  AAGGGGGAGA  AACTTACCTT
1851  GGCGGGTGACG AGCGCGGCGA  AGGTAAAAAC  GGCATTCAAT  TAGCAAAGAA
1901  AACCTCTTTA  GAAAAAGGCT  CAACCATCAA  TGTATCAGGC  AAAGAAAAAG
1951  GCGGACGCGC  TATTGTGTGG  GGCGATATTG  CGTTAATTGA  CGGCAATATT
2001  AACGCTCAAG  GTAGTGGTGA  TATCGCTAAA  ACCGGTGGTT  TTGTGGAGAC
2051  ATCGGGCAT   TATTTATCCA  TTGACAGCAA  TGCAATTGTT  AAAACAAAAG
2101  AGTGGTTGCT  AGACCCTGAT  GATGTAACAA  TTGAAGCCGA  AGACCCCCTT
2151  CGCAATAATA  CCGGTATAAA  TGATGAATTC  CCAACAGGCA  CCGGTGAAGC
2201  AAGCGACCCT  AAAAAAAATA  GCGAACTCAA  AACAACGCTA  ACCAATACAA
2251  CTATTCAAA   TTATCTGAAA  AACGCCTGGA  CAATGAATAT  AACGGCATCA
2301  AGAAAACTTA  CCGTTAATAG  CTCAATCAAC  ATCGGAAGCA  ACTCCCACTT
2351  AATTCTCCAT  AGTAAAGGTC  AGCGTGGCGG  AGCGCGTTCAG ATTGATGGAG
2401  ATATTACTTC  TAAAGGCGGA  AATTTAACCA  TTTATTCTGG  CGGATGGGTT
```

FIG. 7D.

```
2451  GATGTTCATA  AAAATATTAC  GCTTGATCAG  GGTTTTTAA   ATATTACCGC
2501  CGCTTCCGTA  GCTTTTGAAG  GTGGAAATAA  CAAAGCACGC  GACGCGGCAA
2551  ATGCTAAAAT  TGTCGCCCAG  GGCACTGTAA  CCATTACAGG  AGAGGGAAAA
2601  GATTTCAGGG  CTAACAACGT  ATCTTTAAAC  GGAACGGGTA  AAGGTCTGAA
2651  TATCATTTCA  TCAGTGAATA  ATTTAACCCA  CAATCTTAGT  GGCACAATTA
2701  ACATATCTGG  GAATATAACA  ATTAACCAAA  CTACGAGAAA  GAACACCTCG
2751  TATTGGCAAA  CCAGCCATGA  TTCGCACTGG  AACGTCAGTG  CTCTTAATCT
2801  AGAGACAGGC  GCAAATTTTA  CCTTTATTAA  ATACATTTCA  AGCAATAGCA
2851  AAGGCTTAAC  AACACAGTAT  AGAAGCTCTG  CAGGGGTGAA  TTTTAACGGC
2901  GTAAATGGCA  ACATGTCATT  CAATCTCAAA  GAAGGAGCGA  AAGTTAATTT
2951  CAAATTAAAA  CCAAACGAGA  ACATGAACAC  AAGCAAACCT  TTACCAATTC
3001  GGTTTTTAGC  CAATATCACA  GCCACTGGTG  GGGCTCTGT   TTTTTTGAT
3051  ATATATGCCA  ACCATTCTGG  CAGAGGGGCT  GAGTTAAAAA  TGAGTGAAAT
3101  TAATATCTCT  AACGGCGCTA  ATTTTACCTT  AAATTCCCAT  GTTCGCGGCG
3151  ATGACGCTTT  TAAAATCAAC  AAAGACTTAA  CCATAAATGC  AACCAATTCA
3201  AATTTCAGCC  TCAGACAGAC  GAAAGATGAT  TTTTATGACG  GGTACGCACG
```

FIG. 7E.

```
3251  CAATGCCATC  AATTCAACCT  ACAACATATC  CATTCTGGGC  GGTAATGTCA
3301  CCCTTGGTGG  ACAAAACTCA  AGCAGCAGCA  TTACGGGGAA  TATTACTATC
3351  GAGAAAGCAG  CAAATGTTAC  GCTAGAAGCC  AATAACGCCC  CTAATCAGCA
3401  AAACATAAGG  GATAGAGTTA  TAAAACTTGG  CAGCTTGCTC  GTTAATGGGA
3451  GTTTAAGTTT  AACTGGCGAA  AATGCAGATA  TTAAAGGCAA  TCTCACTATT
3501  TCAGAAAGCG  CCACTTTTAA  AGGAAAGACT  AGAGATACCC  TAAATATCAC
3551  CGGCAATTTT  ACCAATAATG  GCACTGCCGA  AATTAATATA  ACACAAGGAG
3601  TGGTAAAACT  TGGCAATGTT  ACCAATGATG  GTGATTTAAA  CATTACCACT
3651  CACGCTAAAC  GCAACCAAAG  AAGCATCATC  GGCGGAGATA  TAATCAACAA
3701  AAAAGGAAGC  TTAAATATTA  CAGACAGTAA  TAATGATGCT  GAAATCCAAA
3751  TTGGCGGCAA  TATCTCGCAA  AAAGAAGGCA  ACCTCACGAT  TTCTTCCGAT
3801  AAAATTAATA  TCACCAAACA  GATAACAATC  AAAAAGGGTA  TTGATGGAGA
3851  GGACTCTAGT  TCAGATGCGA  CAAGTAATGC  CAACCTAACT  ATTAAACCA
3901  AAGAATTGAA  ATTGACAGAA  GACCTAAGTA  TTTCAGTTT  CAATAAAGCA
3951  GAGATTACAG  CCAAAGATGG  TAGAGATTA  ACTATTGGCA  ACAGTAATGA
4001  CGGTAACAGC  GGTGCCGAAG  CCAAAACAGT  AACTTTTAAC  AATGTTAAAG
```

FIG. 7F.

```
4051 ATTCAAAAAT CTCTGCTGAC GGTCACAATG TGACACTAAA TAGCAAAGTG
4101 AAAACATCTA GCAGCAATGG CGGACGTGAA AGCAATAGCG ACAACGATAC
4151 CGGCTTAACT ATTACTGCAA AAAATGTAGA AGTAAACAAA GATATTACTT
4201 CTCTCAAAAC AGTAAATATC ACCGCGTCGG AAAAGGTTAC CACCACAGCA
4251 GGCTCGACCA TTAACGCAAC AAATGGCAAA GCAAGTATTA CAACCAAAAC
4301 AGGTGATATC AGCGGTACGA TTTCCGGTAA CACGGTAAGT GTTAGCGCGA
4351 CTGGTGATTT AACCACTAAA TCCGGCTCAA AAATTGAAGC GAAATCGGGT
4401 GAGGCTAATG TAACAAGTGC ACAGGTACA ATTGGCGGTA CAATTCCGG
4451 TAATACGGTA AATGTTACGG CAAACGCTGG CGATTTAACA GTTGGGAATG
4501 GCGCAGAAAT TAATGCGACA GAAGGAGCTG CAACCTTAAC CGCAACAGGG
4551 AATACCTTGA CTACTGAAGC CGGTTCTAGC ATCACTTCAA CTAAGGGTCA
4601 GGTAGACCTC TTGGCTCAGA ATGGTAGCAT CGCAGGAAGC ATTAATGCTG
4651 CTAATGTGAC ATTAAATACT ACAGGCACCT TAACCACCGT GGCAGGCTCG
4701 GATATTAAAG CAACCAGCGG CACCTTGGTT ATTAACGCAA AAGATGCTAA
4751 GCTAAATGGT GATGCATCAG GTGATAGTAC AGAAGTGAAT GCAGTCAACG
4801 ACTGGGGATT TGGTAGTGTG ACTGCGGGCAA CCTCAAGCAG TGTGAATATC
4851 ACTGGGGATT TAAACACAGT AAATGGGTTA AATATCATTT CGAAAGATGG
```

FIG. 7G.

```
4901  TAGAAACACT  GTGCGCTTAA  GAGGCAAGGA  AATTGAGGTG  AAATATATCC
4951  AGCCAGGTGT  AGCAAGTGTA  GAAGAAGTAA  TTGAAGCGAA  ACGCGTCCTT
5001  GAAAAAGTAA  AAGATTTATC  AGAGAAACAT  AGAGAAACAT  TAGCTAAACT
5051  TGGTGTAAGT  GCTGTACGTT  TGATGAAGAA  TTGTTGAGCC  ATTACAGTCA
5101  ATACACAAAA  TGAATTTACA  ACCAGACCGT  CAAGTCAAGT  GATAATTTCT
5151  GAAGGTAAGG  CGTGTTCTC   AAGTGGTAAT  GGCGCACGAG  TATGTACCAA
5201  TGTTGCTGAC  GATGGACAGC  CGTAGTCAGT  AATTGACAAG  GTAGATTTCA
5251  TCCTGCAATG  AAGTCATTTT  ATTTTCGTAT  TATTTACTGT  GTGGGTTAAA
5301  GTTCAGTACG  GGCTTTACCC  ATCTTGTAAA  AAATTACGGA  GAATACAATA
5351  AAGTATTTTT  AACAGGTTAT  TATTATGAAA  AATATAAAAA  GCAGATTAAA
5401  ACTCAGTGCA  ATATCAGTAT  TGCTTGGCCT  GGCTTCTTCA  TCATTGTATG
5451  CAGAAGAAGC  GTTTTTAGTA  AAAGGCTTTC  AGTTATCTGG  TGCACTTGAA
5501  ACTTTAAGTG  AAGACGCCCA  ACTGTCTGTA  GCAAAATCTT  TATCTAAATA
5551  CCAAGGCTCG  CAAACTTAAA  CAAACCTAAA  AACAGCACAG  CTTGAATTAC
5601  AGGCTGTGCT  AGATAAGATT  GAGCCAAATA  AATTTGATGT  GATATTGCCG
5651  CAACAAACCA  TTACGGATGG  CAATATCATG  TTTGAGCTAG  TCTCGAAATC
```

FIG. 7H.

```
5701  AGCCGCAGAA  AGCCAAGTTT  TTTATAAGGC  GAGCCAGGGT  TATAGTGAAG
5751  AAAATATCGC  TCGTAGCCTG  CCATCTTTGA  AACAAGGAAA  AGTGTATGAA
5801  GATGGTCGTC  AGTGGTTCGA  TTTGCGTGAA  TTTAATATGG  CAAAAGAAAA
5851  CCCGCTTAAG  GTTACCCGTG  TACATTACGA  ACTAAACCCT  AAAAACAAAA
5901  CCTCTAATTT  GATAATTGCG  GGCTTCTCGC  CTTTGGTAA   AACGCGTAGC
5951  TTTATTTCTT  ATGATAATTT  CGGCGCGAGA  GAGTTTAACT  ACCAACGTGT
6001  AAGCTTGGGT  TTTGTTAATG  CCAATTTAAC  TGGTCATGAT  GATGTGTTAA
6151  TTATACCAGT  ATGAGTTATG  CTGATTCTAA  TGATATCGAC  GGCTTACCAA
6201  GTGCGATTAA  TCGTAAATTA  TCAAAAGGTC  AATCTATCTC  TGCGAATCTG
6251  AAATGGAGTT  ATTATCTCCC  AACATTTAAC  CTTGGCATGG  AAGACCAATT
6301  TAAAATTAAT  TTAGGCTACA  ACTACCGCCA  TATTAATCAA  ACCTCCGCGT
6351  TAAATCGCTT  GGGTGAAACG  AAGAAAAAAT  TTGCAGTATC  AGGCGTAAGT
6401  GCAGGCATTG  ATGGACATAT  CCAATTTACC  CCTAAAAACAA  TCTTTAATAT
6451  TGATTAACT   CATCATTATT  ACGCGAGTAA  ATTACCAGGC  TCTTTTGGAA
6501  TGGAGCGCAT  TGGCGAAACA  TTTAATCGCA  GCTATCACAT  TAGCACAGCC
6551  AGTTTAGGGT  TGAGTCAAGA  GTTGCTCAA   GGTTGGCATT  TTAGCAGTCA
6601  ATTATCAGGT  CAATTTACTC  TACAAGATAT  TAGCAGTATA  GATTATTCT
```

FIG. 7I.

```
6651  CTGTAACAGG  TACTTATGGC  GTCAGAGGCT  TTAAATACGG  CGGTGCAAGT
6701  GGTGAGCGCG  GTCTTGTATG  GCGTAATGAA  TTAAGTATGC  CAAAATACAC
6751  CCGCTTCCAA  ATCAGCCCTT  ATGCGTTTTA  TGATGCAGGT  CAGTTCCGTT
6801  ATAATAGCGA  AAATGCTAAA  ACTTACGGCG  AAGATATGCA  CACGGTATCC
6851  TCTGCGGGTT  TAGGCATTAA  AACCTCTCCT  ACACAAAACT  TAAGCCTAGA
6901  TGCTTTTGTT  GCTCGTCGCT  TTGCAAATGC  CAATAGTGAC  AATTTGAATG
6951  GCAACAAAAA  ACGCACAAGC  TCACCTACAA  CCTTCTGGGG  GAGATTAACA
7001  TTCAGTTTCT  AACCCTGAAA  TTTAATCAAC  TGGTAAGCGT  TCCGCCTACC
7051  AGTTTATAAC  TATATGCTTT  ACCCGCCAAT  TTACAGTCTA  TAGGCAACCC
7101  TGTTTTTACC  CTTATATATC  AAATAAACAA  GCTAAGCTGA  ATTTATATGA
7151  CCAAGCAAAC  TCAAGCAAGC  CAAGTAATAC  TAAAAAAACA  TTAATAATAT
7201  TAAACTAAAG  TATACTCCAT  GCCATGGCGA  TACAAGGGAT  GCTTTACTTG
7251  GACAAAAGAA  AATTTGCAAA  ACGCTCCTCA  AGATGCGACC  ACAACCACGC
7301  CGGAATTAAG  CAACAATCAA  ACTCCCCTGC  GAATATTTAA  AAGATTATGA
7351  AAGCCCAGCC  TATTACGCTT  GGAACAACAT  ATCGCAAAAA  GACGCTAATT
7401  GTTTGCTTGT  CGTGAATTAA  TGGTGATTCT  TCT         GGAAAAAATG
```

FIG. 7J.

```
7451  TTGGAGGCGT  TCACGATATT  GAATTTGACG  CACCCGCTCA  GCTGGCATAT
7501  CTACCCGAAA  AATTACTAAT  TTATTTTGCC  ACTCGTCTCG  CTAATGCAAT
7551  TACAACACTC  TTTTCCGACC  CCGAATTGGC  AATTCTGAA   GAAGGGGCGT
7601  TAAAGATGAT  TAGCCTGCAA  CGCTGGTTGA  CGCTGATTTT  TGCCTCTTCC
7651  CCCTACGTTA  ACGCAGACCA  TATTCTCAAT  AAATATAATA  TCAACCCAGA
7701  TTCCGAAGGT  GGCTTTCATT  TAGCAACAGA  CAACTCTTCT  ATTGCTAAAT
7751  TCTGTATTTT  TTACTTACCC  GAATCCAATG  TCAATATGAG  TTTAGATGCG
7801  TTATGGGCAG  GGAATCAACA  ACTTTGTGCT  TCATTGTGTT  TTGCGTTGCA
7851  GTCTTCACGT  TTTATTGGTA  CCGCATCTGC  GTTTCATAAA  AGAGCGGTGG
7901  TTTTACAGTG  GTTTCCTAAA  AAACTCGCCG  AAATTGCTAA  TTTAGATGAA
7951  TTGCCTGCAA  ATATCCTTCA  TGATGTATAT  ATGCACTGCA  GTTATGATTT
8001  AGCAAAAAAC  AAGCACGATG  TTAAGCGTCC  ATTAAACGAA  CTTGTCCGCA
8051  AGCATATCCT  CACGCAAGGA  TGGCAAGACC  GCTACCTTTA  CACCTTAGGT
8101  AAAAGGACG   GCAAACCTGT  GATGATGGTA  CTGCTTGAAC  ATTTAATTC
8151  GGGACATTCG  ATTTATCGTA  CACATTCAAC  TTCAATGATT  GCTGCTCGAG
8201  AAAAATTCTA  TTTAGTCGGC  TTAGGCCATG  AGGGCGTTGA  TAAATAGGT
```

FIG. 7K.

```
8251  CGAGAAGTGT TTGACGAGTT CTTTGAAATC AGTAGCAATA ATATAATGGA
8301  GAGACTGTTT TTTATCCGTA AACAGTGCGA AACTTTCCAA CCCGCAGTGT
8351  TCTATATGCC AAGCATTGGC ATGGATATTA CCACGATTTT TGTGAGCAAC
8401  ACTCGGCTTG CCCCTATTCA AGCTGTAGCC CTGGGTCATC CTGCCACTAC
8451  GCATTCTGAA TTTATTGATT ATGTCATCGT AGAAGATGAT TATGTGGGCA
8501  GTGAAGATTG TTTCAGCGAA ACCCTTTTAC GCTTACCCAA AGATGCCCTA
8551  CCTTATGTAC CTTCTGCACT ATGTCGGTAT TGCCGCTACC ATGTACTCAG
8601  GGAAACCCT GAAGTAGTCA ATATCGGTAT TGCCGCTACC ACAATGAAAT
8651  TAAACCCTGA ATTTTGCTA ACATTGCAAG AAATCAGAGA TAAAGCTAAA
8701  GTCAAAATAC CGCACTTAT CGCACTTGGA CAATCAACAG GCTTGACACA
8751  CCCTTATGTC AAATGGTTTA TCGAAAGCTA TTTAGGTGAC GATGCCACTG
8801  CACATCCCCA TAAATCCGTT TCCTTTCGGT CACGATTATC TGGCAATATT GCGTGATTGC
8851  GATATGCTAC TAGGTTTAG AATACTAACG GCATAATTGA
8901  TATGGTTACA TGATGAAGGT TTGGTGTATG CAAAACGGGG GATGAAGTAC
8951  ATGAACATAT TGTTTAAAC CTGTTTAAAC GCTTAGGACT ACCAGAATGG
9001  CTGATAGCCG ACACACGAGA AACATATATT GAATGTGCTT TGCGTCTAGC
9051  AGAAAACCAT CAAGAACGCC TTGAACTCCG TCGTTACATC ATAGAAAACA
```

FIG. 7L.

```
9101  ACGGCTTACA AAAGCTTTTT ACAGGCGACC CTCGTCCATT GGGCAAAATA
9151  CTGCTTAAGA AAACAAATGA ATGGAAGCGG AAGCACTTGA GTAAAAATA
9201  ACGGTTTTTT AAAGTAAAAG TGCGGTTAAT TTTCAAAGCG TTTTAAAAAC
9251  CTCTCAAAAA TCAACCGCAC TTTTATCTTT ATAACGATCC CGCACGCTGA
9301  CAGTTTATCA GCCTCCCGCC ATAAAACTCC GCCTTTCATG GCGGAGATTT
9351  TAGCCAAAAC TGGCAGAAAT TAAAGGCTAA AATCACCAAA TTGCACCACA
9401  AAATCACCAA TACCCACAAA AAA
```

FIG. 8A.

```
  1 GATCAATCTG GGCGATATTT TTGCCAAAGG TGGTAACATT AATGTCCGCG
 51 CTGCCACTAT TCGCAATAAA GGTAAACTTT CTGCCGACTC TGTAAGCAAA
101 GATAAAAGTG GTAACATTGT TCTCTCTGCC AAAGAAGGTG AAGCGGAAAT
151 TGGCGGTGTA ATTTCCGCTC AAAATCAGCA AGCCAAAGT GGTAAGTTGA
201 TGATTACAGG CGATAAAGTT ACATTGAAAA CGGGTGCAGT TATCGACCTT
251 TCGGGTAAAG AAGGGGGAGA AACTTATCTT GGCGGTGACG AGCGTGGCGA
301 AGGTAAAAAC GGCATTCAAT TAGCAAAGAA AACCACTTTA GAAAAGGCT
351 CAACAATTAA TGTGTCAGGT AAAGAAAAAG GTGGGCGCGC TATTGTATGG
401 GGCGATATTG CGTTAATTGA CGGCAATATT AATGCCCAAG GTAAAGATAT
451 CGCTAAAACT GGTGGTTTTG TGGAGACGTC GGGGCATTAC TTATCCATTG
501 ATGATAACGC AATTGTTAAA ACAAAAGAAT GGCTACTAGA CCCAGAGAAT
551 GTGACTATTG AAGCTCCTTC CGCTTCTCGC GTCGAGCTGG GTGCCGATAG
601 GAATTCCCAC TCGGCAGAGG TGATAAAAGT GACCCTAAAA AAAAATAACA
651 CCTCCTTGAC AACACTAACC AATACAACCA TTTCAAATCT TCTGAAAAGT
701 GCCCACGTGG TGAACATAAC GGCAAGGAGA AAACTTACCG TTAATAGCTC
751 TATCAGTATA GAAAGAGGCT CCCACTTAAT TCTCCACAGT GAAGGTCAGG
```

FIG. 8B.

```
 801  GCGGTCAAGG  TGTTCAGATT  GATAAAGATA  TTACTTCTGA  AGGCGGAAAT
 851  TTAACCATTT  ATTCTGGCGG  ATGGGTTGAT  GTTCATAAAA  ATATTACGCT
 901  TGGTAGCGGC  TTTTTAAACA  TCACAACTAA  AGAAGGAGAT  ATCGCCTTCG
 951  AAGACAAGTC  TGGACGGAAC  AACCTAACCA  TTACAGCCCA  AGGGACCATC
1001  ACCTCAGGTA  ATAGTAACGG  CTTTAGATTT  AACAACGTCT  CTCTAAACAG
1051  CCTTGGCGGA  AAGCTGAGCT  TTACTGACAG  CAGAGAGGAC  AGAGGTAGAA
1101  GAACTAAGGG  TAATATCTCA  AACAAATTTG  ACGGAACGTT  AAACATTTCC
1151  GGAACTGTAG  ATATCTCAAT  GAAAGCACCC  AAAGTCAGCT  GGTTTACAG
1201  AGACAAAGGA  CGCACCTACT  GGAACGTAAC  CACTTTAAAT  GTTACCTCGG
1251  GTAGTAAATT  TAACCTCTCC  ATTGACAGCA  CAGGAAGTGG  CTCAACAGGT
1301  CCAAGCATAC  GCAATGCAGA  ATTAAATGGC  ATAACATTTA  ATAAAGCCAC
1351  TTTTAATATC  GCACAAGGCT  CAACAGCTAA  CTTTAGCATC  AAGGCATCAA
1401  TAATGCCCTT  TAAGAGTAAC  GCTAACTACG  CATTATTTAA  TGAAGATATT
1451  TCAGTCTCAG  GGGGGGGTAG  CGTTAATTTC  AAACTTAACG  CCTCATCTAG
1501  CAACATACAA  ACCCCTGGCG  TAATTATAAA  ATCTCAAAAC  TTTAATGTCT
1551  CAGGAGGGTC  AACTTTAAAT  CTCAAGGCTG  AAGGTTCAAC  AGAAACCGCT
1601  TTTTCAATAG  AAAATGATTT  AAACTTAAAC  GCCACCGGTG  GCAATATAAC
```

FIG. 8C.

```
1651  AATCAGACAA  GTCGAGGGTA  CCGATTCACG  CGTCAACAAA  GGTGTCGCAG
1701  CCAAAAAAAA  CATAACTTTT  AAAGGGGGTA  ATATCACCTT  CGGCTCTCAA
1751  AAAGCCACAA  CAGAAATCAA  AGGCAATGTT  ACCATCAATA  AAAACACTAA
1801  CGCTACTCTT  CGTGGTGCGA  ATTTTGCCGA  AAACAAATCG  CCTTTAAATA
1851  TAGCAGGAAA  TGTTATTAAT  AATGGCAACC  TTACCACTGC  CGGCTCCATT
1901  ATCAATATAG  CCGGAAATCT  TACTGTTTCA  AAAGGCGCTA  ACCTTCAAGC
1951  TATAACAAAT  TACACTTTTA  ATGTAGCCGG  CTCATTTGAC  AACAATGGCG
2001  CTTCAAACAT  TTCCATTGCC  AGAGGAGGGG  CTAAATTTAA  AGATATCAAT
2051  AACACCAGTA  GCTTAAATAT  TACCACCAAC  TCTGATACCA  CTTACCGCAC
2101  CATTATAAAA  GGCAATATAT  CCAACAAATC  AGGTGATTTG  AATATTATTG
2151  ATAAAAAAAG  CGACGCTGAA  ATCCAAATTG  GCGGCAATAT  CTCACAAAAA
2201  GAAGGCAATC  TCACAATTTC  TTCTGATAAA  GTAAATATTA  CCAATCAGAT
2251  AACAATCAAA  GCAGGCGTTG  AAGGGGGGCG  TTCTGATTCA  AGTGAGGCAG
2301  AAAATGCTAA  CCTAACTATT  CAAACCAAAG  AGTTAAAATT  GGCAGGAGAC
2351  CTAAATATTT  CAGGCTTTAA  TAAAGCAGAA  ATTACAGCTA  AAATGGCAG
2401  TGATTTAACT  ATTGGCAATG  CTAGCGGTGG  TAATGCTGAT  GCTAAAAAAG
```

FIG. 8D.

```
2451 TGACTTTGA CAAGGTTAAA GATTCAAAAA TCTCGACTGA CGGTCACAAT
2501 GTAACACTAA ATAGCGAAGT GAAAACGTCT AATGGTAGTA GCAATGCTGG
2551 TAATGATAAC AGCACCGGTT TAACCATTTC CGCAAAAGAT GTAACGGTAA
2601 ACAATAACGT TACCTCCCAC AAGACAATAA ATATCTCTGC CGCAGCAGGA
2651 AATGTAACAA CCAAAGAAGG CACAACTATC AATGCAACCA CAGGCAGCGT
2701 GGAAGTAACT GCTCAAAATG GTACAATTAA AGGCAACATT ACCTCGCAAA
2751 ATGTAACAGT GACAGCAACA GAAAATCTTG TTACCACAGA GAATGCTGTC
2801 ATTAATGCAA CCAGCGGCAC AGTAAACATT AGTACAAAAA CAGGGATAT
2851 TAAAGGTGGA ATTGAATCAA CTTCCGGTAA TGTAAATATT ACAGCGAGCG
2901 GCAATACACT TAAGGTAAGT AATATCACTG GTCAAGATGT AACAGTAACA
2951 GCGGATGCAG GAGCCTTGAC AACTACAGCA GGCTCAACCA TTAGTGCGAC
3001 AACAGGCAAT GCAAATATTA CAACCAAAAC AGGTGATATC AACGGTAAAG
3051 TTGAATCCAG CTCCGGCTCT GTAACACTTG TTGCAACTGG AGCAACTCTT
3101 GCTGTAGGTA ATATTTCAGG TAACACTGTT ACTATTACTG CGGATAGCGG
3151 TAAATTAACC TCCACAGTAG GTTCTACAAT TAATGGGACT AATAGTGTAA
3201 CCACCTCAAG CCAATCAGGC GATATTGAAG GTACAATTTC TGGTAATACA
3251 GTAAATGTTA CAGCAAGCAC TGGTGATTTA ACTATTGGAA ATAGTGCAAA
```

FIG. 8E.

```
3301  AGTTGAAGCG AAAAATGGAG CTGCAACCTT AACTGCTGAA TCAGGCAAAT
3351  TAACCACCCA AACAGGCTCT AGCATTACCT CAAGCAATGG TCAGACAACT
3401  CTTACAGCCA AGGATAGCAG TATCGCAGGA AACATTAATG CTGCTAATGT
3451  GACGTTAAAT ACCACAGGCA CTTTAACTAC TACAGGGGAT TCAAAGATTA
3501  ACGCAACCAG TGGTACCTTA ACAATCAATG CAAAAGATGC CAAATTAGAT
3551  GGTGCTGCAT CAGGTGACCG CACAGTAGTA AATGCAACTA ACGCAAGTGG
3601  CTCTGGTAAC GTGACTGCGA AAACCTCAAG CAGCCGTGAAT ATCACCGGGG
3651  ATTTAAACAC AATAAATGGG TTAAATATCA TTTCGGAAAA TGGTAGAAAC
3701  ACTGTGCGCT TAAGAGGCAA GGAAATTGAT GTGAAAATATA TCCAACCAGG
3751  TGTAGCAAGC GTAGAAGAGG TAATTGAAGC GAAACGCGTC CTTGAGAAGG
3801  TAAAAGATTT ATCTGATGAA GAAAGAGAAA CACTAGCCAA ACTTGGTGTA
3851  AGTGCTGTAC GTTTCGTTGA GCCAAATAAT GCCATTACGG TTAATACACA
3901  AAACGAGTTT ACAACCAAAC CATCAAGTCA AGTGACAATT TCTGAAGGTA
3951  AGGCGTGTTT CTCAAGTGGT AATGGCGCAC AGTGATGTAC CAATGTTGCT
4001  GACGATGGAC AGCAGTAGTC AGTAATTGAC AAGGTAGATT TCATCCTGCA
4051  ATGAAGTCAT TTTATTTTCG TATTATTTAC TGTGTGGGTT AAAGTTCAGT
```

FIG. 8F.

```
4101  ACGGGCTTTA CCCACCCTTGT AAAAAATTAC GAAAAATACA ATAAAGTATT
4151  TTTAACAGGT TATTATTATG AAAAACATAA AAAGCAGATT AAAACTCAGT
4201  GCAATATCAA TATTGCTTGG CTTGGCTTCT TCATCGACGT ATGCAGAAGA
4251  AGCGTTTTTA GTAAAAGGCT TTCAGTTATC TGGCGCG
```

FIG. 9A.

```
  1  GGGAATGAGC GTCGTACACG GTACAGCAAC CATGCAAGTA GACGGCAATA
 51  AAACCACTAT CCGTAATAGC GTCAATGCTA TCATCAATTG GAAACAATTT
101  AACATTGACC AAAATGAAAT GGAGCAGTTT TTACAAGAAA GCAGCAACTC
151  TGCCGTTTTC AACCGTGTTA CATCTGACCA AATCTCCCAA TTAAAAGGGA
201  TTTTAGATTC TAACGGACAA GTCTTTTTAA TCAACCCAAA TGGTATCACA
251  ATAGGTAAAG ACGCAATTAT TAACACTAAT GGCTTTACTG CTTCTACGCT
301  AGACATTTCT AACGAAAACA TCAAGGGCCG TAATTTCACC CTTGAGCAAA
351  CCAAGGATAA AGCACTCGCT GAAATCGTGA ATCACGGTTT AATTACCGTT
401  GGTAAAGACG GTAGCGTAAA CCTTATTGGT GGCAAAGTGA AAAACGAGGG
451  CGTGATTAGC GTAAATGGCG GTAGTATTTC TTTACTTGCA GGGCAAAAAA
501  TCACCATCAG CGATATAATA AATCCAACCA TCACTTACAG CATTGCTGCA
551  CCTGAAAACG AAGCGGATCAA TCTGGGCGAT ATTTTTGCCA AAGGTGGTAA
601  CATTAATGTC CGCGCTGCCA CTATTCGCAA TAAAGGTAAA CTTTCTGCCG
651  ACTCTGTAAG CAAAGATAAA AGTGGTAACA TTGTTCTCTC TGCCAAAGAA
701  GGTGAAGCGG AAATTGGCGG TGTAATTTCC GCTCAAAATC AGCAAGCCAA
751  AGGTGGTAAG TTGATGATTA CAGGTGATAA AGTCACATTA AAAACAGGTG
```

FIG. 9B.

```
 801  CAGTTATCGA CCTTTCAGGT AAAGAAGGGG GAGAGACTTA TCTTGGCGGT
 851  GATGAGCGTG GCGAAGGTAA AAATGGTATT CAATTAGCGA AGAAAACCTC
 901  TTTAGAAAAA GGCTCGACAA TTAATGTATC AGGCAAAGAA AAAGGCGGGC
 951  GCGCTATTGT ATGGGGCGAT ATTGCATTAA TTAATGGTAA CATTAATGCT
1001  CAAGGTAGCG ATATTGCTAA AACTGGCGGC TTTGTGAAAA CATCAGGACA
1051  TGACTTATCC ATTGGTGATG ATGTGATTGT TGACGCTAAA GAGTGGTTAT
1101  TAGACCCAGA TGATGTGTCC ATTGAAACTC TTACATCTGG ACGCAATAAT
1151  ACCGGCGAAA ACCAAGGATA TACAACAGGA GATGGGACTA AAGAGTCACC
1201  TAAAGGTAAT AGTATTTCTA AACCTACATT AACAAACTCA ACTCTTGAGC
1251  AAATCCTAAG AAGAGGTTCT TATGTTAATA TCACTGCTAA TAATAGAATT
1301  TATGTTAATA GCTCCATCAA CTTATCTAAT GGCAGTTTAA CACTTCACAC
1351  TAAACGAGAT GGAGTTAAAA TTAACGGTGA TATTACCTCA AACGAAAATG
1401  GTAATTTAAC CATTAAAGCA GGCTCTTGGG TTGATGTTCA TAAAAACATC
1451  ACGCTTGGTA CGGGTTTTTT GAATATTGTC GCTGGGGATT CTGTAGCTTT
1501  TGAGAGAGAG GGCGATAAAG CACGTAACGC AACAGATGCT CAAATTACCG
1551  CACAAGGGAC GATAACCGTC AATAAAGATG ATAAACAATT TAGATTCAAT
1601  AATGTATCTA TTAACGGGAC GGGCAAGGGT TTAAAGTTTA TTGCAAATCA
```

FIG. 9C.

```
1651  AAATAATTTC  ACTCATAAAT  TTGATGGCGA  AATTAACATA  TCTGGAATAG
1701  TAACAATTAA  CCAAACCACG  AAAAAAGATG  TTAAATACTG  GAATGCATCA
1751  AAAGACTCTT  ACTGGAATGT  TTCTTCTCTT  ACTTTGAATA  CGGTGCAAAA
1801  ATTTACCTTT  ATAAAATTCG  TTGATAGCGG  CTCAAATTCC  CAAGATTTGA
1851  GGTCATCACG  TAGAAGTTTT  GCAGGCGTAC  ATTTTAACGG  CATCGGAGGC
1901  AAAACAAACT  TCAACATCGG  AGCTAACGCA  AAAGCCTTAT  TTAAATTAAA
1951  ACCAAACGCC  GCTACAGACC  CAAAAAAAGA  ATTACCTATT  ACTTTTAACG
2001  CCAACATTAC  AGCTACCGGT  AACAGTGATA  GCTCTGTGAT  GTTTGACATA
2051  CACGCCAATC  TTACCTCTAG  AGCTGCCGGC  ATAAACATGG  ATTCAATTAA
2101  CATTACCGGC  GGGCTTGACT  TTTCCATAAC  ATCCCATAAT  CGCAATAGTA
2151  ATGCTTTTGA  AATCAAAAAA  GACTTAACTA  TAAATGCAAC  TGGCTCGAAT
2201  TTTAGTCTTA  AGCAAACGAA  AGATTCTTTT  TATAATGAAT  ACAGCAAACA
2251  CGCCATTAAC  TCAAGTCATA  ATCTAACCAT  TCTTGGCGGC  AATGTCACTC
2301  TAGGTGGGGA  AAATTCAAGC  AGTAGCATTA  CGGGCAATAT  CAATATCACC
2351  AATAAAGCAA  ATGTTACATT  ACAAGCTGAC  ACCAGCAACA  GCAACACAGG
2401  CTTGAAGAAA  AGAACTCTAA  CTCTTGGCAA  TATATCTGTT  GAGGGAATT
```

FIG. 9D.

```
2451 TAAGCCTAAC TGGTGCAAAT GCAAACATTG TCGGCAATCT TTCTATTGCA
2501 GAAGATTCCA CATTTAAAGG AGAAGCCAGT GACAACCTAA ACATCACCGG
2551 CACCTTTACC AACAACGGTA CCGCCAACAT TAATATAAAA CAAGGAGTGG
2601 TAAAACTCCA AGGCGATATT ATCAATAAAG GTGGTTTAAA TATCACTACT
2651 AACGCCTCAG GCACTCAAAA AACCATTATT AACGGAAATA TAACTAACGA
2701 AAAAGGCGAC TTAAACATCA AGAATATTAA AAAGAAGGCA AGCCGACGCC GAAATCCAAA
2751 TTGGCGGCAA TATCTCACAA AAAGAAGGCA ATCTCACAAT TTCTTCTGAT
2801 AAAGTAAATA TTACCAATCA GATAACAATC AAAGCAGGCG TTGAAGGGGG
2851 GCGTTCTGAT TCAAGTGAGG CAGAAAATGC TAACCTAACT ATTCAAACCA
2901 AAGAGTTAAA ATTGGCAGGA GACCTAAATA TTTCAGGCTT TAATAAAGCA
2951 GAAATTACAG CTAAAAATGG CAGTGATTTA ACTATTGGCA ATGCTAGCGG
3001 TGGTAATGCT GATGCTAAAA AAGTGACTTT TGACAAGGTT AAAGATTCAA
3051 AAATCTCGAC TGACGGTCAC AATGTAACAC TAAATAGCGA AGTGAAAACG
3101 TCTAATGGTA GTAGCAATGC TGGTAATGAT AACAGCACCG GTTAACCAT
3151 TTCCGCAAAA GATGTAACGG TAAACAATAA CGTTACCTCC CACAAGACAA
3201 TAAATATCTC TGCCGCAGCA GGAAATGTAA CAACCAAAGA AGGCACAACT
3251 ATCAATGCAA CCACAGGCAG CGTGGAAGTA ACTGCTCAAA ATGGTACAAT
```

FIG. 9E.

```
3301  TAAAGGCAAC  ATTACCTCGC  AAAATGTAAC  AGTGACAGCA  ACAGAAAATC
3351  TTGTTACCAC  AGAGAATGCT  GTCATTAATG  CAACCAGCGG  CACAGTAAAC
3401  ATTAGTACAA  AAACAGGGGA  TATTAAAGGT  GGAATTGAAT  CAACTTCCGG
3451  TAATGTAAAT  ATTACAGCGA  GCGGCAATAC  ACTTAAGGTA  AGTAATATCA
3501  CTGGTCAAGA  TGTAACAGTA  ACAGCGGATG  CAGGAGCCTT  GACAACTACA
3551  GCAGGCTCAA  CCATTAGTGC  GACAACAGGC  AATGCAAATA  TTACAACCAA
3601  AACAGGTGAT  ATCAACGGTA  AAGTTGAATC  CAGCTCCGC   TCTGTAACAC
3651  TTGTTGCAAC  TGGAGCAACT  CTTGCTGTAG  GTAATATTTC  AGGTAACACT
3701  GTTACTATTA  CTGCGGATAG  CGGTAAATTA  ACCTCCACAG  TAGGTTCTAC
3751  AATTAATGGG  ACTAATAGTG  TAACCACCTC  AAGCCAATCA  GGCGATATTG
3801  AAGGTACAAT  TTCTGGTAAT  ACAGTAAATG  TTACAGCAAG  CACTGGTGAT
3851  TTAACTATTG  GAAATAGTGC  AAAAGTTGAA  GCGAAAAATG  GAGCTGCAAC
3901  CTTAACTGCT  GAATCAGGCA  AATTAACCAC  CCAAACAGGC  TCTAGCATTA
3951  CCTCAAGCAA  TGGTCAGACA  ACTCTTACAG  CCAAGGATAG  CAGTATCGCA
4001  GGAAACATTA  ATGCTGCTAA  TGTGACGTTA  AATACCACAG  GCACTTTAAC
4051  TACTACAGGG  GATTCAAAGA  CAGTGGTACC  CAGTGGTACC  TTAACAATCA
```

FIG. 9F.

```
4101  ATGCAAAAGA TGCCAAATTA GATGGTGCTG CATCAGGTGA CCGCACAGTA
4151  GTAAATGCAA CTAACGCAAG TGGCTCTGGT AACGTGACTG CGAAAACCTC
4201  AAGCAGCGTG AATATCACCG GGGATTTAAA CACAATAAAT GGGTTAAATA
4251  TCATTTCGGA AAATGGTAGA AACACTGTGC GCTTAAGAGG CAAGGAAATT
4301  GATGTGAAAT ATATCCAACC AGGTGTAGCA AGCCGTAGAAG AGGTAATTGA
4351  AGCGAAACGC GTCCTTGAGA AGGTAAAAGA TTTATCTGAT GAAGAAAGAG
4401  AAACACTAGC CAAACTTGGT GTAAGTGCTG TACGTTTCGT TGAGCCAAAT
4451  AATGCCATTA CGGTTAATAC ACAAAACGAG TTTACAACCA AACCATCAAG
4501  TCAAGTGACA ATTTCTGAAG GTAAGGCGTG TTTCTCAAGT GGTAATGGCG
4551  CACGAGTATG TACCAATGTT GCTGACGATG GACAGCAGTA GTCAGTAATT
4601  GACAAGGTAG ATTTCATCCT GCAATGAAGT CATTTATTT TCGTATTATT
4651  TACTGTGTGG GTTAAAGTTC AGTACGGGCT TTACCCACCT TGTAAAAAAT
4701  TA
```

FIG. 10A. COMPARISON OF DERIVED AMINO ACID SEQUENCE

```
              1                                                          50
Hmw3com    ..........  ..........  ..........  ..........  ..........
Hmw4com    ..........  ..........  ..........  ..........  ..........
Hmw1com    MNKIYRLKFS  KRLNALVAVS  ELARGCDHST  EKGSEKPARM  KVRHLALKPL
Hmw2com    MNKIYRLKFS  KRLNALVAVS  ELARGCDHST  EKGSEKPARM  KVRHLALKPL 51                                                        100
Hmw3com    ..........  ..........  ..........  ..........  ..........
Hmw4com    ..........  ..........  ..GMSVVHGT  ATMQVDGNKT  TIRNSVNAII
Hmw1com    SAMLLSLGVT  SIPQSVLASG  LQGMSVVHGT  ATMQVDGNKT  TIRNSVNAII
Hmw2com    SAMLLSLGVT  SIPQSVLASG  LQGMSVVHGT  ATMQVDGNKT  TIRNSVNAII 101                                                       150
Hmw3com    ..........  ..........  ..........  ..........  ..........
Hmw4com    NWKQFNIDQN  EMEQFLQESS  NSAVFNRVTS  DQISQLKGIL  DSNGQVFLIN
```

FIG. 10B.

```
Hmw1com  NWKQFNIDQN  EMVQFLQENN  NSAVFNRVTS  NQISQLKGIL  DSNGQVFLIN
Hmw2com  NWKQFNIDQN  EMVQFLQENN  NSAVFNRVTS  NQISQLKGIL  DSNGQVFLIN
                               151                                200
Hmw3com  ..........  ..........  ..........  ..........  ..........
Hmw4com  PNGITIGKDA  IINTNGFTAS  TLDISNENIK  ARNFTLEQTK  DKALAEIVNH
Hmw1com  PNGITIGKDA  IINTNGFTAS  TLDISNENIK  ARNFTLEQTK  DKALAEIVNH
Hmw2com  PNGITIGKDA  IINTNGFTAS  TLDISNENIK  ARNFTLEQTK  DKALAEIVNH
                               201                                250
Hmw3com  ..........  ..........  ..........  ..........  ..........
Hmw4com  GLITVGKDGS  VNLIGGKVKN  EGVISVNGGS  ISLLAGQKIT  ISDIINPTIT
Hmw1com  GLITVGKDGS  VNLIGGKVKN  EGVISVNGGS  ISLLAGQKIT  ISDIINPTIT
Hmw2com  GLITVGKDGS  VNLIGGKVKN  EGVISVNGGS  ISLLAGQKIT  ISDIINPTIT
                               251                                300
Hmw3com  ..........  INLGDIFAKG  GNINVRAATI  RNKGKLSADS  VSKDKSGNIV
```

FIG. 10C.

| | | | | | |
|---|---|---|---|---|---|
| Hmw4com | YSIAAPENEA | INLGDIFAKG | GNINVRAATI | RNKGKLSADS | VSKDKSGNIV |
| Hmw1com | YSIAAPENEA | VNLGDIFAKG | GNINVRAATI | RNKGKLSADS | VSKDKSGNIV |
| Hmw2com | YSIAAPENEA | VNLGDIFAKG | GNINVRAATI | RNKGKLSADS | VSKDKSGNIV |

301                                                              350

| | | | | | |
|---|---|---|---|---|---|
| Hmw3com | LSAKEGEAEI | GGVISAQNQQ | AKGGKLMITG | DKVTLKTGAV | IDLSGKEGGE |
| Hmw4com | LSAKEGEAEI | GGVISAQNQQ | AKGGKLMITG | DKVTLKTGAV | IDLSGKEGGE |
| Hmw1com | LSAKEGEAEI | GGVISAQNQQ | AKGGKLMITG | DKVTLKTGAV | IDLSGKEGGE |
| Hmw2com | LSAKEGEAEI | GGVISAQNQQ | AKGGKLMITG | DKVTLKTGAV | IDLSGKEGGE |

351                                                              400

| | | | | | |
|---|---|---|---|---|---|
| Hmw3com | TYLGGDERGE | GKNGIQLAKK | TTLEKGSTIN | VSGKEKGGRA | IVWGDIALID |
| Hmw4com | TYLGGDERGE | GKNGIQLAKK | TTLEKGSTIN | VSGKEKGGRA | IVWGDIALID |
| Hmw1com | TYLGGDERGE | GKNGIQLAKK | TTLEKGSTIN | VSGKEKGGRA | IVWGDIALID |
| Hmw2com | TYLGGDERGE | GKNGIQLAKK | TTLEKGSTIN | VSGKEKGGRA | IVWGDIALID |

FIG. 10D.

```
       401                                                          450
Hmw3com  GNINAQGK.D  IAKTGGFVET  SGHYLSIDDN  AIVKTKEWLL  DPENVTIEAP
Hmw4com  GNINAQGS.D  IAKTGGFVET  SGHDLSIGDD  VIVDAKEWLL  DPDDVSIETL
Hmw1com  GNINAQGSGD  IAKTGGFVET  SGHDLFIKDN  AIVDAKEWLL  DPDNVTINAE
Hmw2com  GNINAQGSGD  IAKTGGFVET  SGHYLSIESN  AIVKTKEWLL  DPDDVTIEAE 451                                                          500
Hmw3com  SASRVELGAD  RNSHSAEVIK  VTLKKNNTSL  TTLTNTTISN  LLKSAHVVNI
Hmw4com  TSGRNNTGEN  QGYTTGDGTK  ESPKGNSISK  PTLTNSTLEQ  ILRRGSYVNI
Hmw1com  TAGRSNTSED  DEYTGSGNSA  STPKRNKE.K  TTLTNTTLES  ILKKGTFVNI
Hmw2com  DPLRNNTGIN  DEFPTGTGEA  SDPKKNSELK  TTLTNTTISN  YLKNAWTMNI 501                                                          550
Hmw3com  TARRKLTVNS  SISIERGSHL  ILHSEGQGGQ  GVQIDKDITS  .E...GGNLT
Hmw4com  TANNRIYVNS  SINLSNGS.L  TLHTK...RD  GVKINGDITS  NE...NGNLT
Hmw1com  TANQRIYVNS  SINL.SNGSL  TLWSEGRSGG  GVEINNDITT  GDDTRGANLT
Hmw2com  TASRKLTVNS  SINGSNGSHL  ILHSKGQRGG  GVQIDGDIT.  ...SKGGNLT
```

FIG. 10E.

```
        551                                                         600
Hmw3com IYSGGWVDVH KNITLGS.GF LNITTKEGDI AFEDKSGR.. ..NNLTITAQ
Hmw4com IKAGSWVDVH KNITLGT.GF LNIVAGDS.V AFEREGDKAR NATDAQITAQ
Hmw1com IYSGGWVDVH KNISLGAQGN INITAKQD.I AFEKGSNQV. ......ITGQ
Hmw2com IYSGGWVDVH KNITLD.QGF LNITA.AS.V AFEGGNNKAR DANNLTITAQ 601                                                         650
Hmw3com GTITSG.NSN GFRFNNVSLN SLGGKLSFTD SREDRGRRTK GNISNKFDGT
Hmw4com GTITVNKDDK QFRFNNVSIN GTGKGLKFIA NQN....... .NFTHKFDGE
Hmw1com GTIT.SGNQK GFRFNNVSLN GTGSGLQFTT KRTN......K YAITNKFEGT
Hmw2com GTVTITGEGK DFRANNVSLN GTGKGLNIIS SVNN...... ..LTHNLSGT 651                                                         700
Hmw3com LNISGTVDIS MKAPKVSWFY RD.KGRTYWN VTTLNVTSGS KFNLSIDSTG
Hmw4com INISGIVTIN QTTKKDVKYW NA.SKDSYWN VSSLTNTVQ  KFTF.IKFVD
Hmw1com LNISGKVNIS MVLPKNESGY DKFKGRTYWN LTSLNVSESG EFNLTIDSRG
```

FIG. 10F.

```
Hmw2com  INISGNITIN QTTRKNTSYW QTSHD.SHWN VSALNLETGA NFTF.IKYIS
              701                                          750

Hmw3com  SGSTG...PS IRNA..ELNG ITFN....KA TFNIAQGSTA NFSIKASIMP
Hmw4com  SGSNS...QD LRSSRRSFAG VHFNGIGGKT NFNIGANAKA LFKLKPNAAT
Hmw1com  SDSAGTLTQ. ....PYNLNG ISFN...KDT TFNVERNARV NFDIKAPIGI
Hmw2com  SNSKGLTTQY RSSAGVNFNG V..N...GNM SFNLKEGAKV NFKLKPNENM
              751                                          800

Hmw3com  FKSNANYAL. FNEDISVSG. .GGSVNFKLN ASSSNIQTPG VIIKSQNFNV
Hmw4com  DPKKELPIT. FNANITATGN SDSSVMFDIH A...NLTSRA AGINMDSINI
Hmw1com  NKYSSLNYAS FNGNISVSG. .GGSVDFTLL ASSSNVQTPG VVINSKYFNV
Hmw2com  NTSKPLPI.R FLANITATG. .GGSVFFDIY ANHS...GRG AELKMSEINI
              801                                          850

Hmw3com  SGGSTLNLKA EGSTETAFSI ENDLNLNATG GNITIRQVEG T..DSRVNKG
Hmw4com  TGGLDFSITS HNRNSNAFEI KKDLTINATG SNFSLKQTKD SFYNEYSKHA
```

FIG. 10G.

```
Hmw1com  STGSSLRFKT SGSTKTGFSI EKDLTLNATG GNITLLQVEG T..DGMIGKG
Hmw2com  SNGANFTLNS HVRGDDAFKI NKDLTINATN SNFSLRQTKD DFYDGYARNA
         851                                                  900

Hmw3com  VAAKKNITFK GGNITFGSQK ATTEIKGNVT INKNTNATLR GANFAEN....
Hmw4com  INSSHNLTIL GGNVTLGGEN SSSSITGNIN ITNKANVTLQ ADTSNSNTGL
Hmw1com  IVAKKNITFE GGNITFGSRK AVTEIEGNVT INNNANVTLI GSDFDNHQ..
Hmw2com  INSTYNISIL GGNVTLGGQN SSSSITGNIT IEKAANVTLE ANNAPNQQNI
         901                                                  950

Hmw3com  KSPLNIAGNV INNGNLTTAG SIINIAGNLT VSKGANLQAI TNYTFNVAGS
Hmw4com  KKRTLTLGNI SVEGNLSLTG ANANIVGNLS IAEDSTFKGE ASDNLNITGT
Hmw1com  KPLTIKKDVI INSGNLTAGG NIVNIAGNLT VESNANFKAI TNFTFNVGGL
Hmw2com  RDRVIKLGSL LVNGSLSLTG ENADIKGNLT ISESATFKGK TRDTLNITGN
         951                                                 1000
```

FIG. 10H.

| | | | | | | |
|---|---|---|---|---|---|---|
| Hmw3com | FDNNGASNIS | IARGGAKFK. | DINNTSSLNI | TTNSDTTYRT | IIKGNISNKS | |
| Hmw4com | FTNNGTANIN | IKQGVVKLQG | DINNKGGLNI | TTNASGTQKT | IINGNITNEK | |
| Hmw1com | FDNKGNSNIS | IAKGGARFK. | DIDNSKNLSI | TTNSSSTYRT | IISGNITNKN | |
| Hmw2com | FTNNGTAEIN | ITQGVVKLG. | NVTNDGDLNI | TTHAKRNQRS | IIGGDIINNK | |

1001                                                                   1050

| | | | | | | |
|---|---|---|---|---|---|---|
| Hmw3com | GDLNIIDKKS | DAEIQIGGNI | SQKEGNLTIS | SDKVNITNQI | TIKAGVEGGR | |
| Hmw4com | GDLNIKNIKA | DAEIQIGGNI | SQKEGNLTIS | SDKVNITNQI | TIKAGVEGGR | |
| Hmw1com | GDLNITNEGS | DTEMQIGGDI | SQKEGNLTIS | SDKINITKQI | TIKAGVDGEN | |
| Hmw2com | GSLNITDSNN | DAEIQIGGNI | SQKEGNLTIS | SDKINITKQI | TIKKGIDGED | |

1051                                                                   1100

| | | | | | | |
|---|---|---|---|---|---|---|
| Hmw3com | SDSSEAENAN | LTIQTKELKL | AGDLNISGFN | KAEITAKNGS | DLTIGNASGG | |
| Hmw4com | SDSSEAENAN | LTIQTKELKL | AGDLNISGFN | KAEITAKNGS | DLTIGNASGG | |
| Hmw1com | SDSDATNNAN | LTIKTKELKL | TQDLNISGFN | KAEITAKDGS | DLTIGNTNSA | |
| Hmw2com | SSSDATSNAN | LTIKTKELKL | TEDLSISGFN | KAEITAKDGR | DLTIGNSNDG | |

FIG. 10I.

```
          1101                                                          1150
Hmw3com   N..ADAKKVT  FDKVKDSKIS  TDGHNVTLNS  EVKT..SNGS  SNAGNDNSTG
Hmw4com   N..ADAKKVT  FDKVKDSKIS  TDGHNVTLNS  EVKT..SNGS  SNAGNDNSTG
Hmw1com   D.GTNAKKVT  FNQVKDSKIS  ADGHKVTLHS  KVETSGSNNN  TEDSSDNNAG
Hmw2com   NSGAEAKKVT  FNNVKDSKIS  ADGHNVTLNS  KVKTSSSNGG  RESNSDNDTG 1151                                                          1200
Hmw3com   LTISAKDVTV  NNNVTSHKTI  NISAAAGNVT  TKEGTTINAT  TGSVEVTAQN
Hmw4com   LTISAKDVTV  NNNVTSHKTI  NISAAAGNVT  TKEGTTINAT  TGSVEVTAQN
Hmw1com   LTIDAKNVTV  NNNITSHKAV  SISATSGEIT  TKTGTTINAT  TGNVEIT....
Hmw2com   LTITAKNVEV  NKDVTSLKTV  NITA.SEKVT  TTAGSTINAT  NGKASIT....

1201                                                          1250
Hmw3com   GTIKGNITSQ  NVTVTATENL  VTTENAVINA  TSGTVNISTK  TGDIKGGIES
Hmw4com   GTIKGNITSQ  NVTVTATENL  VTTENAVINA  TSGTVNISTK  TGDIKGGIES
Hmw1com   ..........  ..........  ..........  ........AQ  TGDIKGGIES
```

FIG. 10J.

```
Hmw2com  ..........  ..........  ..........  ..........  ..........  .....TK T.
              1251                                                            1300
Hmw3com  TSGNVNITAS  GNTLKVSNIT  GQDVTVTADA  GALTTTAGST  ISATTGNANI
Hmw4com  TSGNVNITAS  GNTLKVSNIT  GQDVTVTADA  GALTTTAGST  ISATTGNANI
Hmw1com  SSGSVTLTAT  EGALAVSNIS  GNTVTVTANS  GALTTLAGST  IKG.TESVTT
Hmw2com  ..........  ..........  ..........  ..........  ..........
              1301                                                            1350
Hmw3com  TTKTGDINGK  VESSSGSVTL  VATGATLAVG  NISGNTVTIT  ADSGKLTSTV
Hmw4com  TTKTGDINGK  VESSSGSVTL  VATGATLAVG  NISGNTVTIT  ADSGKLTSTV
Hmw1com  SSQSGDIG..  ..........  .......... G  TISGGTVEVK  ATESLTTQSN
Hmw2com  ....GDIS..  ..........  .......... G  TISGNTVSVS  ATVDLTTKSG
              1351                                                            1400
Hmw3com  GSTINGTNSV  TTSSQSGDIE  GTISGNTVNV  TASTGDLTIG  NSAKVEAKNG
Hmw4com  GSTINGTNSV  TTSSQSGDIE  GTISGNTVNV  TASTGDLTIG  NSAKVEAKNG
```

FIG. 10K.

```
Hmw1com  SKIKATTGEA  NVTSATGTIG  GTISGNTVNV  TANAGDLTVG  NGAEINATEG
Hmw2com  SKIEAKSGEA  NVTSATGTIG  GTISGNTVNV  TANAGDLTVG  NGAEINATEG
         1401                                           1450

Hmw3com  AATLTAESGK  LTTQTGSSIT  SSNGQTTLTA  KDSSIAGNIN  AANVTLNTTG
Hmw4com  AATLTAESGK  LTTQTGSSIT  SSNGQTTLTA  KDSSIAGNIN  AANVTLNTTG
Hmw1com  AATLTTSSGK  LTTEASSHIT  SAKGQVNLSA  QDSSVAGSIN  AANVTLNTTG
Hmw2com  AATLTATGNT  LTTEAGSSIT  STKGQVDLLA  QNSSIAGNIN  AANVTLNTTG
         1451                                           1500

Hmw3com  TLTTTGDSKI  NATSGTLTIN  AKDAKLDGAA  SGDRTVVNAT  NASGSGNVTA
Hmw4com  TLTTTGDSKI  NATSGTLTIN  AKDAKLDGAA  SGDRTVVNAT  NASGSGNVTA
Hmw1com  TLTTVKGSNI  NATSGTLTIN  AKDAELNGAA  LGNHTVVNAT  NANGSGSVIA
Hmw2com  TLTTVAGSDI  KATSGTLTIN  AKDAKLNGDA  SGDSTEVNAV  NASGSGSVTA
         1501                                           1550
```

FIG. 10L.

| | | | | | |
|---|---|---|---|---|---|
| Hmw3com | KTSSSVNITG | DLNTINGLNI | ISENGRNTVR | LRGKEIDVKY | IQPGVASVEE |
| Hmw4com | KTSSSVNITG | DLNTINGLNI | ISENGRNTVR | LRGKEIDVKY | IQPGVASVEE |
| Hmw1com | TTSSRVNITG | DLITINGLNI | ISKNGINTVL | LKGVKIDVKY | IQPGIASVDE |
| Hmw2com | ATSSSVNITG | DLNTVNGLNI | ISKDGRNTVR | LRGKEIEVKY | IQPGVASVEE |

1551                                                          1600

| | | | | | |
|---|---|---|---|---|---|
| Hmw3com | VIEAKRVLEK | VKDLSDEERE | TLAKLGVSAV | RFVEPNNAIT | VNTQNEFTTK |
| Hmw4com | VIEAKRVLEK | VKDLSDEERE | TLAKLGVSAV | RFVEPNNAIT | VNTQNEFTTK |
| Hmw1com | VIEAKRILEK | VKDLSDEERE | ALAKLGVSAV | RFIEPNNTIT | VDTQNEFATR |
| Hmw2com | VIEAKRVLEK | VKDLSDEERE | TLAKLGVSAV | RFVEPNNTIT | VNTQNEFTTR |

1601                                         1632

| | | | |
|---|---|---|---|
| Hmw3com | PSSQVTISEG | KACFSSGNGA | RVCTNVADDG QQ |
| Hmw4com | PSSQVTISEG | KACFSSGNGA | RVCTNVADDG QQ |
| Hmw1com | PLSRIVISEG | RACFSNSDGA | TVCVNIADNG R. |
| Hmw2com | PSSQVIISEG | KACFSSGNGA | RVCTNVADDG QP |

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 5116 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
ACAGCGTTCT CTTAATACTA GTACAAACCC ACAATAAAAT ATGACAAACA ACAATTACAA      60
CACCTTTTTT GCAGTCTATA TGCAAATATT TTAAAAAATA GTATAAATCC GCCATATAAA     120
ATGGTATAAT CTTTCATCTT TCATCTTTCA TCTTTCATCT TTCATCTTTC ATCTTTCATC     180
TTTCATCTTT CATCTTTCAT CTTTCATCTT TCATCTTTCA TCTTTCATCT TTCATCTTTC     240
ACATGCCCTG ATGAACCGAG GGAAGGGAGG GAGGGGCAAG AATGAAGAGG GAGCTGAACG     300
AACGCAAATG ATAAAGTAAT TTAATTGTTC AACTAACCTT AGGAGAAAAT ATGAACAAGC     360
TATATCGTCT CAAATTCAGC AAACGCCTGA ATGCTTTGGT TGCTGTGTCT GAATTGGCAC     420
GGGGTTGTGA CCATTCCACA GAAAAGGCA GCGAAAAACC TGCTCGCATG AAAGTGCGTC      480
ACTTAGCGTT AAAGCCACTT TCCGCTATGT TACTATCTTT AGGTGTAACA TCTATTCCAC     540
AATCTGTTTT AGCAAGCGGC TTACAAGGAA TGGATGTAGT ACACGGCACA GCCACTATGC     600
AAGTAGATGG TAATAAAACC ATTATCCGCA ACAGTGTTGA CGATATCATT AATTGGAAAC     660
AATTTAACAT CGACCAAAAT GAAATGGTGC AGTTTTTACA AGAAACAAC AACTCCGCCG      720
TATTCAACCG TGTTACATCT AACCAAATCT CCCAATTAAA AGGGATTTTA GATTCTAACG     780
GACAAGTCTT TTTAATCAAC CCAAATGGTA TCACAATAGG TAAAGACGCA ATTATTAACA     840
CTAATGGCTT TACGGCTTCT ACGCTAGACA TTTCTAACGA AAACATCAAG GCGCGTAATT     900
TCACCTTCGA GCAAACCAAA GATAAAGCGC TCGCTGAAAT TGTGAATCAC GGTTTAATTA     960
CTGTCGGTAA AGACGGCAGT GTAAATCTTA TTGGTGGCAA AGTGAAAAAC GAGGGTGTGA    1020
TTAGCGTAAA TGGTGGCAGC ATTTCTTTAC TCGCAGGGCA AAAAATCACC ATCAGCGATA    1080
TAATAAACCC AACCATTACT TACAGCATTG CCGCGCCTGA AAATGAAGCG GTCAATCTGG    1140
GCGATATTTT TGCCAAGGC GGTAACATTA ATGTCCGTGC TGCCACTATT CGAAACCAAG     1200
GTAAACTTTC TGCTGATTCT GTAAGCAAAG ATAAAGCGG CAATATTGTT CTTTCCGCCA     1260
AAGAGGGTGA AGCGGAAATT GGCGGTGTAA TTTCCGCTCA AAATCAGCAA GCTAAAGGCG    1320
GCAAGCTGAT GATTACAGGC GATAAAGTCA CATTAAAAAC AGGTGCAGTT ATCGACCTTT    1380
CAGGTAAAGA AGGGGGAGAA ACTTACCTTG GCGGTGACGA GCGCGGCGAA GGTAAAAAGG    1440
GCATTCAATT AGCAAAGAAA ACCTCTTTAG AAAAAGGCTC AACCATCAAT GTATCAGGCA    1500
AAGAAAAAGG CGGACGCGCT ATTGTGTGGG GCGATATTGC GTTAATTGAC GGCAATATTA    1560
ACGCTCAAGG TAGTGGTGAT ATCGCTAAAA CCGGTGGTTT TGTGGAGACG TCGGGGCATG    1620
ATTTATTCAT CAAAGACAAT GCAATTGTTG ACGCCAAAGA GTGGTTGTTA GACCCGGATA    1680
ATGTATCTAT TAATGCAGAA ACAGCAGGAC GCAGCAATAC TTCAGAAGAC GATGAATACA    1740
CGGGATCCGG GAATAGTGCC AGCACCCCAA AACGAAACAA AGAAAGACA ACATTAACAA     1800
ACACAACTCT TGAGAGTATA CTAAAAAAG GTACCTTTGT TAACATCACT GCTAATCAAC     1860
GCATCTATGT CAATAGCTCC ATTAATTTAT CCAATGGCAG CTTAACTCTT TGGAGTGAGG    1920
GTCGGAGCGG TGGCGGCGTT GAGATTAACA ACGATATTAC CACCGGTGAT GATACCAGAG    1980
GTGCAAACTT AACAATTTAC TCAGGCGGCT GGGTTGATGT TCATAAAAAT ATCTCACTCG    2040
GGGCGCAAGG TAACATAAAC ATTACAGCTA ACAAGATAT CGCCTTTGAG AAAGGAAGCA     2100
ACCAAGTCAT TACAGGTCAA GGGACTATTA CCTCAGGCAA TCAAAAGGT TTTAGATTTA     2160
ATAATGTCTC TCTAAACGGC ACTGGCAGCG GACTGCAATT CACCACTAAA AGAACCAATA    2220
AATACGCTAT CACAAATAAA TTTGAAGGGA CTTTAAATAT TTCAGGGAAA GTGAACATCT    2280
CAATGGTTTT ACCTAAAAAT GAAAGTGGAT ATGATAAATT CAAAGGACGC ACTTACTGGA    2340
```

```
ATTTAACCTC CTTAAATGTT TCCGAGAGTG GCGAGTTTAA CCTCACTATT GACTCCAGAG    2400
GAAGCGATAG TGCAGGCACA CTTACCCAGC CTTATAATTT AAACGGTATA TCATTCAACA    2460
AAGACACTAC CTTTAATGTT GAACGAAATG CAAGAGTCAA CTTTGACATC AAGGCACCAA    2520
TAGGGATAAA TAAGTATTCT AGTTTGAATT ACGCATCATT TAATGGAAAC ATTTCAGTTT    2580
CGGGAGGGGG GAGTGTTGAT TTCACACTTC TCGCCTCATC CTCTAACGTC CAAACCCCCG    2640
GTGTAGTTAT AAATTCTAAA TACTTTAATG TTTCAACAGG GTCAAGTTTA AGATTTAAAA    2700
CTTCAGGCTC AACAAAAACT GGCTTCTCAA TAGAGAAAGA TTTAACTTTA AATGCCACCG    2760
GAGGCAACAT AACACTTTTG CAAGTTGAAG GCACCGATGG AATGATTGGT AAAGGCATTG    2820
TAGCCAAAAA AAACATAACC TTTGAAGGAG GTAACATCAC CTTTGGCTCC AGGAAAGCCG    2880
TAACAGAAAT CGAAGGCAAT GTTACTATCA ATAACAACGC TAACGTCACT CTTATCGGTT    2940
CGGATTTTGA CAACCATCAA AAACCTTTAA CTATTAAAAA AGATGTCATC ATTAATAGCG    3000
GCAACCTTAC CGCTGGAGGC AATATTGTCA ATATAGCCGG AAATCTTACC GTTGAAAGTA    3060
ACGCTAATTT CAAAGCTATC ACAAATTTCA CTTTTAATGT AGGCGGCTTG TTTGACAACA    3120
AAGGCAATTC AAATATTTCC ATTGCCAAAG GAGGGGCTCG CTTTAAAGAC ATTGATAATT    3180
CCAAGAATTT AAGCATCACC ACCAACTCCA GCTCCACTTA CCGCACTATT ATAAGCGGCA    3240
ATATAACCAA TAAAAACGGT GATTTAAATA TTACGAACGA AGGTAGTGAT ACTGAAATGC    3300
AAATTGGCGG CGATGTCTCG CAAAAAGAAG GTAATCTCAC GATTTCTTCT GACAAAATCA    3360
ATATTACCAA ACAGATAACA ATCAAGGCAG GTGTTGATGG GGAGAATTCC GATTCAGACG    3420
CGACAAACAA TGCCAATCTA ACCATTAAAA CCAAGAATT GAAATTAACG CAAGACCTAA    3480
ATATTTCAGG TTTCAATAAA GCAGAGATTA CAGCTAAAGA TGGTAGTGAT TTAACTATTG    3540
GTAACACCAA TAGTGCTGAT GGTACTAATG CCAAAAAAGT AACCTTTAAC CAGGTTAAAG    3600
ATTCAAAAAT CTCTGCTGAC GGTCACAAGG TGACACTACA CAGCAAAGTG GAAACATCCG    3660
GTAGTAATAA CAACACTGAA GATAGCAGTG ACAATAATGC CGGCTTAACT ATCGATGCAA    3720
AAAATGTAAC AGTAAACAAC AATATTACTT CTCACAAAGC AGTGAGCATC TCTGCGACAA    3780
GTGGAGAAAT TACCACTAAA ACAGGTACAA CCATTAACGC AACCACTGGT AACGTGGAGA    3840
TAACCGCTCA AACAGGTAGT ATCCTAGGTG GAATTGAGTC CAGCTCTGGC TCTGTAACAC    3900
TTACTGCAAC CGAGGGCGCT CTTGCTGTAA GCAATATTTC GGGCAACACC GTTACTGTTA    3960
CTGCAAATAG CGGTGCATTA ACCACTTTGG CAGGCTCTAC AATTAAAGGA ACCGAGAGTG    4020
TAACCACTTC AAGTCAATCA GGCGATATCG GCGGTACGAT TTCTGGTGGC ACAGTAGAGG    4080
TTAAAGCAAC CGAAAGTTTA ACCACTCAAT CCAATTCAAA AATTAAAGCA ACAACAGGCG    4140
AGGCTAACGT AACAAGTGCA ACAGGTACAA TTGGTGGTAC GATTTCCGGT AATACGGTAA    4200
ATGTTACGGC AAACGCTGGC GATTAACAG TTGGGAATGG CGCAGAAATT AATGCGACAG    4260
AAGGAGCTGC AACCTTAACT ACATCATCGG GCAAATTAAC TACCGAAGCT AGTTCACACA    4320
TTACTTCAGC CAAGGGTCAG GTAAATCTTT CAGCTCAGGA TGGTAGCGTT GCAGGAAGTA    4380
TTAATGCCGC CAATGTGACA CTAAATACTA CAGGCACTTT AACTACCGTG AAGGGTTCAA    4440
ACATTAATGC AACCAGCGGT ACCTTGGTTA TTAACGCAAA AGACGCTGAG CTAAATGGCG    4500
CAGCATTGGG TAACCACACA GTGGTAAATG CAACCAACGC AAATGGCTCC GGCAGCGTAA    4560
TCGCGACAAC CTCAAGCAGA GTGAACATCA CTGGGGATTT AATCACAATA AATGGATTAA    4620
ATATCATTTC AAAAAACGGT ATAAACACCG TACTGTTAAA AGGCGTTAAA ATTGATGTGA    4680
AATACATTCA ACCGGGTATA GCAAGCGTAG ATGAAGTAAT TGAAGCGAAA CGCATCCTTG    4740
```

```
AGAAGGTAAA  AGATTTATCT  GATGAAGAAA  GAGAAGCGTT  AGCTAAACTT  GGAGTAAGTG    4800

CTGTACGTTT  TATTGAGCCA  AATAATACAA  TTACAGTCGA  TACACAAAAT  GAATTTGCAA    4860

CCAGACCATT  AAGTCGAATA  GTGATTTCTG  AAGGCAGGGC  GTGTTTCTCA  AACAGTGATG    4920

GCGCGACGGT  GTGCGTTAAT  ATCGCTGATA  ACGGGCGGTA  GCGGTCAGTA  ATTGACAAGG    4980

TAGATTTCAT  CCTGCAATGA  AGTCATTTTA  TTTTCGTATT  ATTTACTGTG  TGGGTTAAAG    5040

TTCAGTACGG  GCTTTACCCA  TCTTGTAAAA  AATTACGGAG  AATACAATAA  AGTATTTTA     5100

ACAGGTATT  ATTATG                                                          5116
```

( 2 ) INFORMATION FOR SEQ ID NO:2:

( i ) SEQUENCE CHARACTERISTICS:
        ( A ) LENGTH: 1536 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Met  Asn  Lys  Ile  Tyr  Arg  Leu  Lys  Phe  Ser  Lys  Arg  Leu  Asn  Ala  Leu
 1              5                   10                      15

Val  Ala  Val  Ser  Glu  Leu  Ala  Arg  Gly  Cys  Asp  His  Ser  Thr  Glu  Lys
              20                       25                      30

Gly  Ser  Glu  Lys  Pro  Ala  Arg  Met  Lys  Val  Arg  His  Leu  Ala  Leu  Lys
           35                       40                      45

Pro  Leu  Ser  Ala  Met  Leu  Leu  Ser  Leu  Gly  Val  Thr  Ser  Ile  Pro  Gln
      50                       55                      60

Ser  Val  Leu  Ala  Ser  Gly  Leu  Gln  Gly  Met  Asp  Val  Val  His  Gly  Thr
65                   70                       75                       80

Ala  Thr  Met  Gln  Val  Asp  Gly  Asn  Lys  Thr  Ile  Ile  Arg  Asn  Ser  Val
                     85                       90                      95

Asp  Ala  Ile  Ile  Asn  Trp  Lys  Gln  Phe  Asn  Ile  Asp  Gln  Asn  Glu  Met
               100                      105                     110

Val  Gln  Phe  Leu  Gln  Glu  Asn  Asn  Ser  Ala  Val  Phe  Asn  Arg  Val
          115                      120                      125

Thr  Ser  Asn  Gln  Ile  Ser  Gln  Leu  Lys  Gly  Ile  Leu  Asp  Ser  Asn  Gly
     130                      135                      140

Gln  Val  Phe  Leu  Ile  Asn  Pro  Asn  Gly  Ile  Thr  Ile  Gly  Lys  Asp  Ala
145                      150                      155                     160

Ile  Ile  Asn  Thr  Asn  Gly  Phe  Thr  Ala  Ser  Thr  Leu  Asp  Ile  Ser  Asn
                165                      170                     175

Glu  Asn  Ile  Lys  Ala  Arg  Asn  Phe  Thr  Phe  Glu  Gln  Thr  Lys  Asp  Lys
               180                      185                     190

Ala  Leu  Ala  Glu  Ile  Val  Asn  His  Gly  Leu  Ile  Thr  Val  Gly  Lys  Asp
          195                      200                     205

Gly  Ser  Val  Asn  Leu  Ile  Gly  Gly  Lys  Val  Lys  Asn  Glu  Gly  Val  Ile
     210                      215                      220

Ser  Val  Asn  Gly  Gly  Ser  Ile  Ser  Leu  Leu  Ala  Gly  Gln  Lys  Ile  Thr
225                      230                      235                     240

Ile  Ser  Asp  Ile  Ile  Asn  Pro  Thr  Ile  Thr  Tyr  Ser  Ile  Ala  Ala  Pro
                245                      250                     255

Glu  Asn  Glu  Ala  Val  Asn  Leu  Gly  Asp  Ile  Phe  Ala  Lys  Gly  Gly  Asn
          260                      265                     270

Ile  Asn  Val  Arg  Ala  Ala  Thr  Ile  Arg  Asn  Gln  Gly  Lys  Leu  Ser  Ala
```

-continued

|  |  |  | 275 |  |  |  |  | 280 |  |  |  |  | 285 |  |
|---|---|---|---|---|---|---|---|---|---|---|---|---|---|---|
| Asp | Ser | Val | Ser | Lys | Asp | Ser | Gly | Asn | Ile | Val | Leu | Ser | Ala | Lys |
|  | 290 |  |  |  | 295 |  |  |  |  | 300 |  |  |  |  |
| Glu | Gly | Glu | Ala | Glu | Ile | Gly | Gly | Val | Ile | Ser | Ala | Gln | Asn | Gln | Gln |
| 305 |  |  |  |  | 310 |  |  |  | 315 |  |  |  |  | 320 |
| Ala | Lys | Gly | Gly | Lys | Leu | Met | Ile | Thr | Gly | Asp | Lys | Val | Thr | Leu | Lys |
|  |  |  |  | 325 |  |  |  | 330 |  |  |  |  |  | 335 |
| Thr | Gly | Ala | Val | Ile | Asp | Leu | Ser | Gly | Lys | Glu | Gly | Gly | Glu | Thr | Tyr |
|  |  |  | 340 |  |  |  | 345 |  |  |  |  | 350 |  |  |
| Leu | Gly | Gly | Asp | Glu | Arg | Gly | Glu | Gly | Lys | Asn | Gly | Ile | Gln | Leu | Ala |
|  |  | 355 |  |  |  | 360 |  |  |  |  | 365 |  |  |  |
| Lys | Lys | Thr | Ser | Leu | Glu | Lys | Gly | Ser | Thr | Ile | Asn | Val | Ser | Gly | Lys |
| 370 |  |  |  |  | 375 |  |  |  | 380 |  |  |  |  |  |
| Glu | Lys | Gly | Gly | Arg | Ala | Ile | Val | Trp | Gly | Asp | Ile | Ala | Leu | Ile | Asp |
| 385 |  |  |  | 390 |  |  |  |  | 395 |  |  |  |  | 400 |
| Gly | Asn | Ile | Asn | Ala | Gln | Gly | Ser | Gly | Asp | Ile | Ala | Lys | Thr | Gly | Gly |
|  |  |  |  | 405 |  |  |  | 410 |  |  |  |  | 415 |  |
| Phe | Val | Glu | Thr | Ser | Gly | His | Asp | Leu | Phe | Ile | Lys | Asp | Asn | Ala | Ile |
|  |  |  | 420 |  |  |  | 425 |  |  |  |  | 430 |  |  |
| Val | Asp | Ala | Lys | Glu | Trp | Leu | Leu | Asp | Phe | Asp | Asn | Val | Ser | Ile | Asn |
|  |  | 435 |  |  |  | 440 |  |  |  |  | 445 |  |  |  |
| Ala | Glu | Thr | Ala | Gly | Arg | Ser | Asn | Thr | Ser | Glu | Asp | Asp | Glu | Tyr | Thr |
|  | 450 |  |  |  | 455 |  |  |  |  | 460 |  |  |  |  |
| Gly | Ser | Gly | Asn | Ser | Ala | Ser | Thr | Pro | Lys | Arg | Asn | Lys | Glu | Lys | Thr |
| 465 |  |  |  |  | 470 |  |  |  | 475 |  |  |  |  | 480 |
| Thr | Leu | Thr | Asn | Thr | Thr | Leu | Glu | Ser | Ile | Leu | Lys | Lys | Gly | Thr | Phe |
|  |  |  |  | 485 |  |  |  | 490 |  |  |  |  | 495 |  |
| Val | Asn | Ile | Thr | Ala | Asn | Gln | Arg | Ile | Tyr | Val | Asn | Ser | Ser | Ile | Asn |
|  |  |  | 500 |  |  |  | 505 |  |  |  |  | 510 |  |  |
| Leu | Ser | Asn | Gly | Ser | Leu | Thr | Leu | Trp | Ser | Glu | Gly | Arg | Ser | Gly | Gly |
|  |  | 515 |  |  |  | 520 |  |  |  |  | 525 |  |  |  |
| Gly | Val | Glu | Ile | Asn | Asn | Asp | Ile | Thr | Thr | Gly | Asp | Asp | Thr | Arg | Gly |
|  | 530 |  |  |  | 535 |  |  |  |  | 540 |  |  |  |  |
| Ala | Asn | Leu | Thr | Ile | Tyr | Ser | Gly | Gly | Trp | Val | Asp | Val | His | Lys | Asn |
| 545 |  |  |  |  | 550 |  |  |  | 555 |  |  |  |  | 560 |
| Ile | Ser | Leu | Gly | Ala | Gln | Gly | Asn | Ile | Asn | Ile | Thr | Ala | Lys | Gln | Asp |
|  |  |  |  | 565 |  |  |  | 570 |  |  |  |  | 575 |  |
| Ile | Ala | Phe | Glu | Lys | Gly | Ser | Asn | Gln | Val | Ile | Thr | Gly | Gln | Gly | Thr |
|  |  |  | 580 |  |  |  | 585 |  |  |  |  | 590 |  |  |
| Ile | Thr | Ser | Gly | Asn | Gln | Lys | Gly | Phe | Arg | Phe | Asn | Asn | Val | Ser | Leu |
|  |  | 595 |  |  |  | 600 |  |  |  |  | 605 |  |  |  |
| Asn | Gly | Thr | Gly | Ser | Gly | Leu | Gln | Phe | Thr | Thr | Lys | Arg | Thr | Asn | Lys |
|  | 610 |  |  |  | 615 |  |  |  |  | 620 |  |  |  |  |
| Tyr | Ala | Ile | Thr | Asn | Lys | Phe | Glu | Gly | Thr | Leu | Asn | Ile | Ser | Gly | Lys |
| 625 |  |  |  |  | 630 |  |  |  | 635 |  |  |  |  | 640 |
| Val | Asn | Ile | Ser | Met | Val | Leu | Pro | Lys | Asn | Glu | Ser | Gly | Tyr | Asp | Lys |
|  |  |  |  | 645 |  |  |  | 650 |  |  |  |  | 655 |  |
| Phe | Lys | Gly | Arg | Thr | Tyr | Trp | Asn | Leu | Thr | Ser | Leu | Asn | Val | Ser | Glu |
|  |  |  | 660 |  |  |  | 665 |  |  |  |  | 670 |  |  |
| Ser | Gly | Glu | Phe | Asn | Leu | Thr | Ile | Asp | Ser | Arg | Gly | Ser | Asp | Ser | Ala |
|  |  | 675 |  |  |  | 680 |  |  |  |  | 685 |  |  |  |
| Gly | Thr | Leu | Thr | Gln | Pro | Tyr | Asn | Leu | Asn | Gly | Ile | Ser | Phe | Asn | Lys |
|  | 690 |  |  |  | 695 |  |  |  |  | 700 |  |  |  |  |

-continued

```
Asp  Thr  Thr  Phe  Asn  Val  Glu  Arg  Asn  Ala  Arg  Val  Asn  Phe  Asp  Ile
705                 710                 715                 720

Lys  Ala  Pro  Ile  Gly  Ile  Asn  Lys  Tyr  Ser  Ser  Leu  Asn  Tyr  Ala  Ser
                    725                 730                 735

Phe  Asn  Gly  Asn  Ile  Ser  Val  Ser  Gly  Gly  Ser  Val  Asp  Phe  Thr
               740                 745                 750

Leu  Leu  Ala  Ser  Ser  Ser  Asn  Val  Gln  Thr  Pro  Gly  Val  Val  Ile  Asn
               755                 760                 765

Ser  Lys  Tyr  Phe  Asn  Val  Ser  Thr  Gly  Ser  Ser  Leu  Arg  Phe  Lys  Thr
770                 775                 780

Ser  Gly  Ser  Thr  Lys  Thr  Gly  Phe  Ser  Ile  Glu  Lys  Asp  Leu  Thr  Leu
785                 790                 795                 800

Asn  Ala  Thr  Gly  Gly  Asn  Ile  Thr  Leu  Leu  Gln  Val  Glu  Gly  Thr  Asp
                    805                 810                 815

Gly  Met  Ile  Gly  Lys  Gly  Ile  Val  Ala  Lys  Lys  Asn  Ile  Thr  Phe  Glu
               820                 825                 830

Gly  Gly  Asn  Ile  Thr  Phe  Gly  Ser  Arg  Lys  Ala  Val  Thr  Glu  Ile  Glu
               835                 840                 845

Gly  Asn  Val  Thr  Ile  Asn  Asn  Ala  Asn  Val  Thr  Leu  Ile  Gly  Ser
850                 855                 860

Asp  Phe  Asp  Asn  His  Gln  Lys  Pro  Leu  Thr  Ile  Lys  Lys  Asp  Val  Ile
865                 870                 875                 880

Ile  Asn  Ser  Gly  Asn  Leu  Thr  Ala  Gly  Gly  Asn  Ile  Val  Asn  Ile  Ala
                    885                 890                 895

Gly  Asn  Leu  Thr  Val  Glu  Ser  Asn  Ala  Asn  Phe  Lys  Ala  Ile  Thr  Asn
               900                 905                 910

Phe  Thr  Phe  Asn  Val  Gly  Gly  Leu  Phe  Asp  Asn  Lys  Gly  Asn  Ser  Asn
               915                 920                 925

Ile  Ser  Ile  Ala  Lys  Gly  Gly  Ala  Arg  Phe  Lys  Asp  Ile  Asp  Asn  Ser
930                 935                 940

Lys  Asn  Leu  Ser  Ile  Thr  Thr  Asn  Ser  Ser  Ser  Thr  Tyr  Arg  Thr  Ile
945                 950                 955                 960

Ile  Ser  Gly  Asn  Ile  Thr  Asn  Lys  Asn  Gly  Asp  Leu  Asn  Ile  Thr  Asn
                    965                 970                 975

Glu  Gly  Ser  Asp  Thr  Glu  Met  Gln  Ile  Gly  Gly  Asp  Val  Ser  Gln  Lys
               980                 985                 990

Glu  Gly  Asn  Leu  Thr  Ile  Ser  Ser  Asp  Lys  Ile  Asn  Ile  Thr  Lys  Gln
               995                 1000                1005

Ile  Thr  Ile  Lys  Ala  Gly  Val  Asp  Gly  Glu  Asn  Ser  Asp  Ser  Asp  Ala
               1010                1015                1020

Thr  Asn  Asn  Ala  Asn  Leu  Thr  Ile  Lys  Thr  Lys  Glu  Leu  Lys  Leu  Thr
1025                1030                1035                1040

Gln  Asp  Leu  Asn  Ile  Ser  Gly  Phe  Asn  Lys  Ala  Glu  Ile  Thr  Ala  Lys
                    1045                1050                1055

Asp  Gly  Ser  Asp  Leu  Thr  Ile  Gly  Asn  Thr  Asn  Ser  Ala  Asp  Gly  Thr
               1060                1065                1070

Asn  Ala  Lys  Lys  Val  Thr  Phe  Asn  Gln  Val  Lys  Asp  Ser  Lys  Ile  Ser
               1075                1080                1085

Ala  Asp  Gly  His  Lys  Val  Thr  Leu  His  Ser  Lys  Val  Glu  Thr  Ser  Gly
               1090                1095                1100

Ser  Asn  Asn  Asn  Thr  Glu  Asp  Ser  Ser  Asp  Asn  Ala  Gly  Leu  Thr
1105                1110                1115                1120

Ile  Asp  Ala  Lys  Asn  Val  Thr  Val  Asn  Asn  Asn  Ile  Thr  Ser  His  Lys
                    1125                1130                1135
```

-continued

```
Ala  Val  Ser  Ile  Ser  Ala  Thr  Ser  Gly  Glu  Ile  Thr  Thr  Lys  Thr  Gly
               1140               1145                    1150

Thr  Thr  Ile  Asn  Ala  Thr  Thr  Gly  Asn  Val  Glu  Ile  Thr  Ala  Gln  Thr
               1155               1160                    1165

Gly  Ser  Ile  Leu  Gly  Gly  Ile  Glu  Ser  Ser  Ser  Gly  Ser  Val  Thr  Leu
               1170               1175                    1180

Thr  Ala  Thr  Glu  Gly  Ala  Leu  Ala  Val  Ser  Asn  Ile  Ser  Gly  Asn  Thr
1185                1190                    1195                         1200

Val  Thr  Val  Thr  Ala  Asn  Ser  Gly  Ala  Leu  Thr  Thr  Leu  Ala  Gly  Ser
               1205               1210                    1215

Thr  Ile  Lys  Gly  Thr  Glu  Ser  Val  Thr  Thr  Ser  Ser  Gln  Ser  Gly  Asp
               1220               1225                    1230

Ile  Gly  Gly  Thr  Ile  Ser  Gly  Gly  Thr  Val  Glu  Val  Lys  Ala  Thr  Glu
               1235               1240                    1245

Ser  Leu  Thr  Thr  Gln  Ser  Asn  Ser  Lys  Ile  Lys  Ala  Thr  Thr  Gly  Glu
               1250               1255                    1260

Ala  Asn  Val  Thr  Ser  Ala  Thr  Gly  Thr  Ile  Gly  Gly  Thr  Ile  Ser  Gly
1265                1270                    1275                         1280

Asn  Thr  Val  Asn  Val  Thr  Ala  Asn  Ala  Gly  Asp  Leu  Thr  Val  Gly  Asn
               1285               1290                    1295

Gly  Ala  Glu  Ile  Asn  Ala  Thr  Glu  Gly  Ala  Ala  Thr  Leu  Thr  Thr  Ser
               1300               1305                    1310

Ser  Gly  Lys  Leu  Thr  Thr  Glu  Ala  Ser  Ser  His  Ile  Thr  Ser  Ala  Lys
               1315               1320                    1325

Gly  Gln  Val  Asn  Leu  Ser  Ala  Gln  Asp  Gly  Ser  Val  Ala  Gly  Ser  Ile
               1330               1335                    1340

Asn  Ala  Ala  Asn  Val  Thr  Leu  Asn  Thr  Thr  Gly  Thr  Leu  Thr  Thr  Val
1345                1350                    1355                         1360

Lys  Gly  Ser  Asn  Ile  Asn  Ala  Thr  Ser  Gly  Thr  Leu  Val  Ile  Asn  Ala
               1365               1370                    1375

Lys  Asp  Ala  Glu  Leu  Asn  Gly  Ala  Ala  Leu  Gly  Asn  His  Thr  Val  Val
               1380               1385                    1390

Asn  Ala  Thr  Asn  Ala  Asn  Gly  Ser  Gly  Ser  Val  Ile  Ala  Thr  Thr  Ser
               1395               1400                    1405

Ser  Arg  Val  Asn  Ile  Thr  Gly  Asp  Leu  Ile  Thr  Ile  Asn  Gly  Leu  Asn
               1410               1415                    1420

Ile  Ile  Ser  Lys  Asn  Gly  Ile  Asn  Thr  Val  Leu  Leu  Lys  Gly  Val  Lys
1425                1430                    1435                         1440

Ile  Asp  Val  Lys  Tyr  Ile  Gln  Pro  Gly  Ile  Ala  Ser  Val  Asp  Glu  Val
               1445               1450                    1455

Ile  Glu  Ala  Lys  Arg  Ile  Leu  Glu  Lys  Val  Lys  Asp  Leu  Ser  Asp  Glu
               1460               1465                    1470

Glu  Arg  Glu  Ala  Leu  Ala  Lys  Leu  Gly  Val  Ser  Ala  Val  Arg  Phe  Ile
               1475               1480                    1485

Glu  Pro  Asn  Asn  Thr  Ile  Thr  Val  Asp  Thr  Gln  Asn  Glu  Phe  Ala  Thr
               1490               1495                    1500

Arg  Pro  Leu  Ser  Arg  Ile  Val  Ile  Ser  Glu  Gly  Arg  Ala  Cys  Phe  Ser
1505                1510                    1515                         1520

Asn  Ser  Asp  Gly  Ala  Thr  Val  Cys  Val  Asn  Ile  Ala  Asp  Asn  Gly  Arg
               1525               1530                    1535
```

( 2 ) INFORMATION FOR SEQ ID NO:3:

( i ) SEQUENCE CHARACTERISTICS:

5,869,065

27

28

-continued (A) LENGTH: 4937 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:3:

| | | | | | | |
|---|---|---|---|---|---|---|
| TAAATATACA | AGATAATAAA | AATAAATCAA | GATTTTTGTG | ATGACAAACA | ACAATTACAA | 60 |
| CACCTTTTTT | GCAGTCTATA | TGCAAATATT | TTAAAAAAAT | AGTATAAATC | CGCCATATAA | 120 |
| AATGGTATAA | TCTTTCATCT | TTCATCTTTA | ATCTTTCATC | TTTCATCTTT | CATCTTTCAT | 180 |
| CTTTCATCTT | TCATCTTTCA | TCTTTCATCT | TTCATCTTTC | ATCTTTCATC | TTTCATCTTT | 240 |
| CACATGAAAT | GATGAACCGA | GGGAAGGGAG | GGAGGGGCAA | GAATGAAGAG | GGAGCTGAAC | 300 |
| GAACGCAAAT | GATAAAGTAA | TTTAATTGTT | CAACTAACCT | TAGGAGAAAA | TATGAACAAG | 360 |
| ATATATCGTC | TCAAATTCAG | CAAACGCCTG | AATGCTTTGG | TTGCTGTGTC | TGAATTGGCA | 420 |
| CGGGGTTGTG | ACCATTCCAC | AGAAAAGGC | TTCCGCTATG | TTACTATCTT | TAGGTGTAAC | 480 |
| CACTTAGCGT | TAAAGCCACT | TTCCGCTATG | TTACTATCTT | TAGGTGTAAC | ATCTATTCCA | 540 |
| CAATCTGTTT | TAGCAAGCGG | CTTACAAGGA | ATGGATGTAG | TACACGGCAC | AGCCACTATG | 600 |
| CAAGTAGATG | GTAATAAAAC | CATTATCCGC | AACAGTGTTG | ACGCTATCAT | TAATTGGAAA | 660 |
| CAATTTAACA | TCGACCAAAA | TGAAATGGTG | CAGTTTTTAC | AAGAAAACAA | CAACTCCGCC | 720 |
| GTATTCAACC | GTGTTACATC | TAACCAAATC | TCCCAATTAA | AAGGGATTTT | AGATTCTAAC | 780 |
| GGACAAGTCT | TTTTAATCAA | CCCAAATGGT | ATCACAATAG | GTAAAGACGC | AATTATTAAC | 840 |
| ACTAATGGCT | TTACGGCTTC | TACGCTAGAC | ATTTCTAACG | AAAACATCAA | GGCGCGTAAT | 900 |
| TTCACCTTCG | AGCAAACCAA | AGATAAAGCG | CTCGCTGAAA | TTGTGAATCA | CGGTTTAATT | 960 |
| ACTGTCGGTA | AAGACGGCAG | TGTAAATCTT | ATTGGTGGCA | AAGTGAAAAA | CGAGGGTGTG | 1020 |
| ATTAGCGTAA | ATGGTGGCAG | CATTTCTTTA | CTCGCAGGGC | AAAAAATCAC | CATCAGCGAT | 1080 |
| ATAATAAACC | CAACCATTAC | TTACAGCATT | GCCGCGCCTG | AAAATGAAGC | GGTCAATCTG | 1140 |
| GGCGATATTT | TTGCCAAAGG | CGGTAACATT | AATGTCCGTG | CTGCCACTAT | TCGAAACCAA | 1200 |
| GGTAAACTTT | CTGCTGATTC | TGTAAGCAAA | GATAAAAGCG | GCAATATTGT | TCTTTCCGCC | 1260 |
| AAAGAGGGTG | AAGCGGAAAT | TGGCGGTGTA | ATTTCCGCTC | AAAATCAGCA | AGCTAAAGGC | 1320 |
| GGCAAGCTGA | TGATTACAGG | CGATAAAGTC | ACATTAAAAA | CAGGTGCAGT | TATCGACCTT | 1380 |
| TCAGGTAAAG | AAGGGGGAGA | AACTTACCTT | GGCGGTGACG | AGCGCGGCGA | AGGTAAAAAC | 1440 |
| GGCATTCAAT | TAGCAAAGAA | AACCTCTTTA | GAAAAAGGCT | CAACCATCAA | TGTATCAGGC | 1500 |
| AAAGAAAAAG | GCGGACGCGC | TATTGTGTGG | GGCGATATTG | CGTTAATTGA | CGGCAATATT | 1560 |
| AACGCTCAAG | GTAGTGGTGA | TATCGCTAAA | ACCGGTGGTT | TTGTGGAGAC | ATCGGGGCAT | 1620 |
| TATTTATCCA | TTGACAGCAA | TGCAATTGTT | AAAACAAAAG | AGTGGTTGCT | AGACCCTGAT | 1680 |
| GATGTAACAA | TTGAAGCCGA | AGACCCCCTT | CGCAATAATA | CCGGTATAAA | TGATGAATTC | 1740 |
| CCAACAGGCA | CCGGTGAAGC | AAGCGACCCT | AAAAAAAATA | GCGAACTCAA | AACAACGCTA | 1800 |
| ACCAATACAA | CTATTTCAAA | TTATCTGAAA | AACGCCTGGA | CAATGAATAT | AACGGCATCA | 1860 |
| AGAAACTTA | CCGTTAATAG | CTCAATCAAC | ATCGGAAGCA | ACTCCCACTT | AATTCTCCAT | 1920 |
| AGTAAAGGTC | AGCGTGGCGG | AGGCGTTCAG | ATTGATGGAG | ATATTACTTC | TAAAGGCGGA | 1980 |
| AATTTAACCA | TTTATTCTGG | CGGATGGGTT | GATGTTCATA | AAAATATTAC | GCTTGATCAG | 2040 |
| GGTTTTTTAA | ATATTACCGC | CGCTTCCGTA | GCTTTTGAAG | GTGGAAATAA | CAAAGCACGC | 2100 |
| GACGCGGCAA | ATGCTAAAAT | TGTCGCCCAG | GGCACTGTAA | CCATTACAGG | AGAGGGAAAA | 2160 |

```
GATTTCAGGG CTAACAACGT ATCTTTAAAC GGAACGGGTA AAGGTCTGAA TATCATTTCA    2220

TCAGTGAATA ATTTAACCCA CAATCTTAGT GGCACAATTA ACATATCTGG AATATAACA     2280

ATTAACCAAA CTACGAGAAA GAACACCTCG TATTGGCAAA CCAGCCATGA TTCGCACTGG    2340

AACGTCAGTG CTCTTAATCT AGAGACAGGC GCAAATTTTA CCTTTATTAA ATACATTTCA    2400

AGCAATAGCA AAGGCTTAAC AACACAGTAT AGAAGCTCTG CAGGGGTGAA TTTTAACGGC    2460

GTAAATGGCA ACATGTCATT CAATCTCAAA GAAGGAGCGA AAGTTAATTT CAAATTAAAA    2520

CCAAACGAGA ACATGAACAC AAGCAAACCT TTACCAATTC GGTTTTAGC CAATATCACA     2580

GCCACTGGTG GGGGCTCTGT TTTTTTTGAT ATATATGCCA ACCATTCTGG CAGAGGGGCT    2640

GAGTTAAAAA TGAGTGAAAT TAATATCTCT AACGGCGCTA ATTTTACCTT AAATTCCCAT    2700

GTTCGCGGCG ATGACGCTTT TAAAATCAAC AAAGACTTAA CCATAAATGC AACCAATTCA    2760

AATTTCAGCC TCAGACAGAC GAAAGATGAT TTTTATGACG GGTACGCACG CAATGCCATC    2820

AATTCAACCT ACAACATATC CATTCTGGGC GGTAATGTCA CCCTTGGTGG ACAAAACTCA    2880

AGCAGCAGCA TTACGGGGAA TATTACTATC GAGAAAGCAG CAAATGTTAC GCTAGAAGCC    2940

AATAACGCCC CTAATCAGCA AAACATAAGG GATAGAGTTA TAAAACTTGG CAGCTTGCTC    3000

GTTAATGGGA GTTTAAGTTT AACTGGCGAA AATGCAGATA TTAAAGGCAA TCTCACTATT    3060

TCAGAAAGCG CCACTTTTAA AGGAAAGACT AGAGATACCC TAAATATCAC CGGCAATTTT    3120

ACCAATAATG GCACTGCCGA AATTAATATA ACACAAGGAG TGGTAAAACT TGGCAATGTT    3180

ACCAATGATG GTGATTTAAA CATTACCACT CACGCTAAAC GCAACCAAAG AAGCATCATC    3240

GGCGGAGATA TAATCAACAA AAAAGGAAGC TTAAATATTA CAGACAGTAA TAATGATGCT    3300

GAAATCCAAA TTGGCGGCAA TATCTCGCAA AAAGAAGGCA ACCTCACGAT TTCTTCCGAT    3360

AAAATTAATA TCACCAAACA GATAACAATC AAAAAGGGTA TTGATGGAGA GGACTCTAGT    3420

TCAGATGCGA CAAGTAATGC CAACCTAACT ATTAAAACCA AAGAATTGAA ATTGACAGAA    3480

GACCTAAGTA TTTCAGGTTT CAATAAAGCA GAGATTACAG CCAAAGATGG TAGAGATTTA    3540

ACTATTGGCA ACAGTAATGA CGGTAACAGC GGTGCCGAAG CCAAAACAGT AACTTTTAAC    3600

AATGTTAAAG ATTCAAAAAT CTCTGCTGAC GGTCACAATG TGACACTAAA TAGCAAAGTG    3660

AAAACATCTA GCAGCAATGG CGGACGTGAA AGCAATAGCG ACAACGATAC CGGCTTAACT    3720

ATTACTGCAA AAAATGTAGA AGTAAACAAA GATATTACTT CTCTCAAAAC AGTAAATATC    3780

ACCGCGTCGG AAAAGGTTAC CACCACAGCA GGCTCGACCA TTAACGCAAC AAATGGCAAA    3840

GCAAGTATTA CAACCAAAAC AGGTGATATC AGCGGTACGA TTTCCGGTAA CACGGTAAGT    3900

GTTAGCGCGA CTGGTGATTT AACCACTAAA TCCGGCTCAA AAATTGAAGC GAAATCGGGT    3960

GAGGCTAATG TAACAAGTGC AACAGGTACA ATTGGCGGTA CAATTTCCGG TAATACGGTA    4020

AATGTTACGG CAAACGCTGG CGATTTAACA GTTGGGAATG GCGCAGAAAT TAATGCGACA    4080

GAAGGAGCTG CAACCTTAAC CGCAACAGGG AATACCTTGA CTACTGAAGC CGGTTCTAGC    4140

ATCACTTCAA CTAAGGGTCA GGTAGACCTC TTGGCTCAGA ATGGTAGCAT CGCAGGAAGC    4200

ATTAATGCTG CTAATGTGAC ATTAAATACT ACAGGCACCT TAACCACCGT GGCAGGCTCG    4260

GATATTAAAG CAACCAGCGG CACCTTGGTT ATTAACGCAA AAGATGCTAA GCTAAATGGT    4320

GATGCATCAG GTGATAGTAC AGAAGTGAAT GCAGTCAACG CAAGCGGCTC TGGTAGTGTG    4380

ACTGCGGCAA CCTCAAGCAG TGTGAATATC ACTGGGGATT TAAACACAGT AAATGGGTTA    4440

AATATCATTT CGAAAGATGG TAGAAACACT GTGCGCTTAA GAGGCAAGGA AATTGAGGTG    4500

AAATATATCC AGCCAGGTGT AGCAAGTGTA GAAGAAGTAA TTGAAGCGAA ACGCGTCCTT    4560
```

-continued

```
GAAAAAGTAA AAGATTTATC TGATGAAGAA AGAGAAACAT TAGCTAAACT TGGTGTAAGT      4620

GCTGTACGTT TTGTTGAGCC AAATAATACA ATTACAGTCA ATACACAAAA TGAATTTACA      4680

ACCAGACCGT CAAGTCAAGT GATAATTTCT GAAGGTAAGG CGTGTTCTC AAGTGGTAAT       4740

GGCGCACGAG TATGTACCAA TGTTGCTGAC GATGGACAGC CGTAGTCAGT AATTGACAAG      4800

GTAGATTTCA TCCTGCAATG AAGTCATTTT ATTTCGTAT TATTTACTGT GTGGGTAAA       4860

GTTCAGTACG GGCTTTACCC ATCTTGTAAA AAATTACGGA GAATACAATA AAGTATTTTT     4920

AACAGGTTAT TATTATG                                                      4937
```

(2) INFORMATION FOR SEQ ID NO:4:

(i) SEQUENCE CHARACTERISTICS:
        (A) LENGTH: 1477 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met  Asn  Lys  Ile  Tyr  Arg  Leu  Lys  Phe  Ser  Lys  Arg  Leu  Asn  Ala  Leu
 1                  5                        10                       15

Val  Ala  Val  Ser  Glu  Leu  Ala  Arg  Gly  Cys  Asp  His  Ser  Thr  Glu  Lys
              20                       25                       30

Gly  Ser  Glu  Lys  Pro  Ala  Arg  Met  Lys  Val  Arg  His  Leu  Ala  Leu  Lys
              35                       40                       45

Pro  Leu  Ser  Ala  Met  Leu  Leu  Ser  Leu  Gly  Val  Thr  Ser  Ile  Pro  Gln
              50                       55                       60

Ser  Val  Leu  Ala  Ser  Gly  Leu  Gln  Gly  Met  Asp  Val  Val  His  Gly  Thr
 65                       70                       75                       80

Ala  Thr  Met  Gln  Val  Asp  Gly  Asn  Lys  Thr  Ile  Ile  Arg  Asn  Ser  Val
                        85                       90                       95

Asp  Ala  Ile  Ile  Asn  Trp  Lys  Gln  Phe  Asn  Ile  Asp  Gln  Asn  Glu  Met
                       100                      105                      110

Val  Gln  Phe  Leu  Gln  Glu  Asn  Asn  Ser  Ala  Val  Phe  Asn  Arg  Val
                 115                      120                      125

Thr  Ser  Asn  Gln  Ile  Ser  Gln  Leu  Lys  Gly  Ile  Leu  Asp  Ser  Asn  Gly
         130                      135                      140

Gln  Val  Phe  Leu  Ile  Asn  Pro  Asn  Gly  Ile  Thr  Ile  Gly  Lys  Asp  Ala
145                      150                      155                      160

Ile  Ile  Asn  Thr  Asn  Gly  Phe  Thr  Ala  Ser  Thr  Leu  Asp  Ile  Ser  Asn
                  165                      170                      175

Glu  Asn  Ile  Lys  Ala  Arg  Asn  Phe  Thr  Phe  Glu  Gln  Thr  Lys  Asp  Lys
              180                      185                      190

Ala  Leu  Ala  Glu  Ile  Val  Asn  His  Gly  Leu  Ile  Thr  Val  Gly  Lys  Asp
         195                      200                      205

Gly  Ser  Val  Asn  Leu  Ile  Gly  Gly  Lys  Val  Lys  Asn  Glu  Gly  Val  Ile
         210                      215                      220

Ser  Val  Asn  Gly  Gly  Ser  Ile  Ser  Leu  Leu  Ala  Gly  Gln  Lys  Ile  Thr
225                      230                      235                      240

Ile  Ser  Asp  Ile  Ile  Asn  Pro  Thr  Ile  Thr  Tyr  Ser  Ile  Ala  Ala  Pro
                  245                      250                      255

Glu  Asn  Glu  Ala  Val  Asn  Leu  Gly  Asp  Ile  Phe  Ala  Lys  Gly  Gly  Asn
              260                      265                      270

Ile  Asn  Val  Arg  Ala  Ala  Thr  Ile  Arg  Asn  Gln  Gly  Lys  Leu  Ser  Ala
```

-continued

|   |   |   | 275 |   |   |   | 280 |   |   |   | 285 |   |   |
|---|---|---|---|---|---|---|---|---|---|---|---|---|---|

Asp Ser Val Ser Lys Asp Ser Gly Asn Ile Val Leu Ser Ala Lys
        290                 295                 300

Glu Gly Glu Ala Glu Ile Gly Gly Val Ile Ser Ala Gln Asn Gln Gln
305                     310                 315                 320

Ala Lys Gly Gly Lys Leu Met Ile Thr Gly Asp Lys Val Thr Leu Lys
                    325                 330                     335

Thr Gly Ala Val Ile Asp Leu Ser Gly Lys Glu Gly Gly Glu Thr Tyr
                340                 345                 350

Leu Gly Gly Asp Glu Arg Gly Glu Gly Lys Asn Gly Ile Gln Leu Ala
            355                 360                 365

Lys Lys Thr Ser Leu Glu Lys Gly Ser Thr Ile Asn Val Ser Gly Lys
370                 375                 380

Glu Lys Gly Gly Phe Ala Ile Val Trp Gly Asp Ile Ala Leu Ile Asp
385                 390                 395                 400

Gly Asn Ile Asn Ala Gln Gly Ser Gly Asp Ile Ala Lys Thr Gly Gly
                405                 410                 415

Phe Val Glu Thr Ser Gly His Asp Leu Phe Ile Lys Asp Asn Ala Ile
            420                 425                 430

Val Asp Ala Lys Glu Trp Leu Leu Asp Phe Asp Asn Val Ser Ile Asn
            435                 440                 445

Ala Glu Asp Pro Leu Phe Asn Asn Thr Gly Ile Asn Asp Glu Phe Pro
        450                 455                 460

Thr Gly Thr Gly Glu Ala Ser Asp Pro Lys Lys Asn Ser Glu Leu Lys
465                 470                 475                 480

Thr Thr Leu Thr Asn Thr Thr Ile Ser Asn Tyr Leu Lys Asn Ala Trp
                485                 490                 495

Thr Met Asn Ile Thr Ala Ser Arg Lys Leu Thr Val Asn Ser Ser Ile
            500                 505                 510

Asn Ile Gly Ser Asn Ser His Leu Ile Leu His Ser Lys Gly Gln Arg
            515                 520                 525

Gly Gly Gly Val Gln Ile Asp Gly Asp Ile Thr Ser Lys Gly Gly Asn
530                 535                 540

Leu Thr Ile Tyr Ser Gly Gly Trp Val Asp Val His Lys Asn Ile Thr
545                 550                 555                 560

Leu Asp Gln Gly Phe Leu Asn Ile Thr Ala Ala Ser Val Ala Phe Glu
            565                 570                 575

Gly Gly Asn Asn Lys Ala Arg Asp Ala Ala Asn Ala Lys Ile Val Ala
        580                 585                 590

Gln Gly Thr Val Thr Ile Thr Gly Glu Gly Lys Asp Phe Arg Ala Asn
        595                 600                 605

Asn Val Ser Leu Asn Gly Thr Gly Lys Gly Leu Asn Ile Ile Ser Ser
    610                 615                 620

Val Asn Asn Leu Thr His Asn Leu Ser Gly Thr Ile Asn Ile Ser Gly
625                 630                 635                 640

Asn Ile Thr Ile Asn Gln Thr Thr Arg Lys Asn Thr Ser Tyr Trp Gln
                645                 650                 655

Thr Ser His Asp Ser His Trp Asn Val Ser Ala Leu Asn Leu Glu Thr
            660                 665                 670

Gly Ala Asn Phe Thr Phe Ile Lys Tyr Ile Ser Ser Asn Ser Lys Gly
        675                 680                 685

Leu Thr Thr Gln Tyr Arg Ser Ser Ala Gly Val Asn Phe Asn Gly Val
690                 695                 700

```
Asn Gly Asn Met Ser Phe Asn Leu Lys Glu Gly Ala Lys Val Asn Phe
705                 710                 715                 720

Lys Leu Lys Pro Asn Glu Asn Met Asn Thr Ser Lys Pro Leu Pro Ile
                725                 730                 735

Arg Phe Leu Ala Asn Ile Thr Ala Thr Gly Gly Gly Ser Val Phe Phe
                740                 745                 750

Asp Ile Tyr Ala Asn His Ser Gly Arg Gly Ala Glu Leu Lys Met Ser
            755                 760                 765

Glu Ile Asn Ile Ser Asn Gly Ala Asn Phe Thr Leu Asn Ser His Val
        770                 775                 780

Arg Gly Asp Asp Ala Phe Lys Ile Asn Lys Asp Leu Thr Ile Asn Ala
785                 790                 795                 800

Thr Asn Ser Asn Phe Ser Leu Arg Gln Thr Lys Asp Asp Phe Tyr Asp
                805                 810                 815

Gly Tyr Ala Arg Asn Ala Ile Asn Ser Thr Tyr Asn Ile Ser Ile Leu
            820                 825                 830

Gly Gly Asn Val Thr Leu Gly Gly Gln Asn Ser Ser Ser Ile Thr
            835                 840                 845

Gly Asn Ile Thr Ile Glu Lys Ala Ala Asn Val Thr Leu Glu Ala Asn
    850                 855                 860

Asn Ala Pro Asn Gln Gln Asn Ile Arg Asp Arg Val Ile Lys Leu Gly
865                 870                 875                 880

Ser Leu Leu Val Asn Gly Ser Leu Ser Leu Thr Gly Glu Asn Ala Asp
                885                 890                 895

Ile Lys Gly Asn Leu Thr Ile Ser Glu Ser Ala Thr Phe Lys Gly Lys
            900                 905                 910

Thr Arg Asp Thr Leu Asn Ile Thr Gly Asn Phe Thr Asn Asn Gly Thr
        915                 920                 925

Ala Glu Ile Asn Ile Thr Gln Gly Val Val Lys Leu Gly Asn Val Thr
    930                 935                 940

Asn Asp Gly Asp Leu Asn Ile Thr Thr His Ala Lys Arg Asn Gln Arg
945                 950                 955                 960

Ser Ile Ile Gly Gly Asp Ile Ile Asn Lys Lys Gly Ser Leu Asn Ile
            965                 970                 975

Thr Asp Ser Asn Asn Asp Ala Glu Ile Gln Ile Gly Gly Asn Ile Ser
            980                 985                 990

Gln Lys Glu Gly Asn Leu Thr Ile Ser Ser Asp Lys Ile Asn Ile Thr
        995                 1000                1005

Lys Gln Ile Thr Ile Lys Lys Gly Ile Asp Gly Glu Asp Ser Ser Ser
        1010                1015                1020

Asp Ala Thr Ser Asn Ala Asn Leu Thr Ile Lys Thr Lys Glu Leu Lys
1025                1030                1035                1040

Leu Thr Glu Asp Leu Ser Ile Ser Gly Phe Asn Lys Ala Glu Ile Thr
                1045                1050                1055

Ala Lys Asp Gly Arg Asp Leu Thr Ile Gly Asn Ser Asn Asp Gly Asn
            1060                1065                1070

Ser Gly Ala Glu Ala Lys Thr Val Thr Phe Asn Asn Val Lys Asp Ser
        1075                1080                1085

Lys Ile Ser Ala Asp Gly His Asn Val Thr Leu Asn Ser Lys Val Lys
    1090                1095                1100

Thr Ser Ser Ser Asn Gly Gly Arg Glu Ser Asn Ser Asp Asn Asp Thr
1105                1110                1115                1120

Gly Leu Thr Ile Thr Ala Lys Asn Val Glu Val Asn Lys Asp Ile Thr
            1125                1130                1135
```

-continued

```
Ser  Leu  Lys  Thr  Val  Asn  Ile  Thr  Ala  Ser  Glu  Lys  Val  Thr  Thr  Thr
               1140                    1145                    1150

Ala  Gly  Ser  Thr  Ile  Asn  Ala  Thr  Asn  Gly  Lys  Ala  Ser  Ile  Thr  Thr
               1155                    1160                    1165

Lys  Thr  Gly  Asp  Ile  Ser  Gly  Thr  Ile  Ser  Gly  Asn  Thr  Val  Ser  Val
               1170                    1175                    1180

Ser  Ala  Thr  Val  Asp  Leu  Thr  Thr  Lys  Ser  Gly  Ser  Lys  Ile  Glu  Ala
1185                    1190                    1195                         1200

Lys  Ser  Gly  Glu  Ala  Asn  Val  Thr  Ser  Ala  Thr  Gly  Thr  Ile  Gly  Gly
                    1205                    1210                    1215

Thr  Ile  Ser  Gly  Asn  Thr  Val  Asn  Val  Thr  Ala  Asn  Ala  Gly  Asp  Leu
                    1220                    1225                    1230

Thr  Val  Gly  Asn  Gly  Ala  Glu  Ile  Asn  Ala  Thr  Glu  Gly  Ala  Ala  Thr
                    1235                    1240                    1245

Leu  Thr  Ala  Thr  Gly  Asn  Thr  Leu  Thr  Thr  Glu  Ala  Gly  Ser  Ser  Ile
               1250                    1255                    1260

Thr  Ser  Thr  Lys  Gly  Gln  Val  Asp  Leu  Leu  Ala  Gln  Asn  Gly  Ser  Ile
1265                    1270                    1275                         1280

Ala  Gly  Ser  Ile  Asn  Ala  Ala  Asn  Val  Thr  Leu  Asn  Thr  Thr  Gly  Thr
                    1285                    1290                    1295

Leu  Thr  Thr  Val  Ala  Gly  Ser  Asp  Ile  Lys  Ala  Thr  Ser  Gly  Thr  Leu
               1300                    1305                    1310

Val  Ile  Asn  Ala  Lys  Asp  Ala  Lys  Leu  Asn  Gly  Asp  Ala  Ser  Gly  Asp
               1315                    1320                    1325

Ser  Thr  Glu  Val  Asn  Ala  Val  Asn  Ala  Ser  Gly  Ser  Gly  Ser  Val  Thr
               1330                    1335                    1340

Ala  Ala  Thr  Ser  Ser  Ser  Val  Asn  Ile  Thr  Gly  Asp  Leu  Asn  Thr  Val
1345                    1350                    1355                         1360

Asn  Gly  Leu  Asn  Ile  Ile  Ser  Lys  Asp  Gly  Arg  Asn  Thr  Val  Arg  Leu
                    1365                    1370                    1375

Arg  Gly  Lys  Glu  Ile  Glu  Val  Lys  Tyr  Ile  Gln  Pro  Gly  Val  Ala  Ser
                    1380                    1385                    1390

Val  Glu  Glu  Val  Ile  Glu  Ala  Lys  Arg  Val  Leu  Glu  Lys  Val  Lys  Asp
                    1395                    1400                    1405

Leu  Ser  Asp  Glu  Glu  Arg  Glu  Thr  Leu  Ala  Lys  Leu  Gly  Val  Ser  Ala
          1410                    1415                    1420

Val  Arg  Phe  Val  Glu  Pro  Asn  Asn  Thr  Ile  Thr  Val  Asn  Thr  Gln  Asn
1425                    1430                    1435                         1440

Glu  Phe  Thr  Thr  Arg  Pro  Ser  Ser  Gln  Val  Ile  Ile  Ser  Glu  Gly  Lys
                    1445                    1450                    1455

Ala  Cys  Phe  Ser  Ser  Gly  Asn  Gly  Ala  Arg  Val  Cys  Thr  Asn  Val  Ala
                    1460                    1465                    1470

Asp  Asp  Gly  Gln  Pro
               1475
```

( 2 ) INFORMATION FOR SEQ ID NO:5:

( i ) SEQUENCE CHARACTERISTICS:
        ( A ) LENGTH: 9171 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

-continued

| | | | | | |
|---|---|---|---|---|---|
| ACAGCGTTCT | CTTAATACTA | GTACAAACCC | ACAATAAAAT | ATGACAAACA | ACAATTACAA | 60 |
| CACCTTTTTT | GCAGTCTATA | TGCAAATATT | TTAAAAAATA | GTATAAATCC | GCCATATAAA | 120 |
| ATGGTATAAT | CTTTCATCTT | TCATCTTTCA | TCTTTCATCT | TTCATCTTTC | ATCTTTCATC | 180 |
| TTTCATCTTT | CATCTTTCAT | CTTTCATCTT | TCATCTTTCA | TCTTTCATCT | TTCATCTTTC | 240 |
| ACATGAAATG | ATGAACCGAG | GGAAGGGAGG | GAGGGGCAAG | AATGAAGAGG | GAGCTGAACG | 300 |
| AACGCAAATG | ATAAAGTAAT | TTAATTGTTC | AACTAACCTT | AGGAGAAAAT | ATGAACAAGA | 360 |
| TATATCGTCT | CAAATTCAGC | AAACGCCTGA | ATGCTTTGGT | TGCTGTGTCT | GAATTGGCAC | 420 |
| GGGGTTGTGA | CCATTCCACA | GAAAAAGGCA | GCGAAAAACC | TGCTCGCATG | AAAGTGCGTC | 480 |
| ACTTAGCGTT | AAAGCCACTT | TCCGCTATGT | TACTATCTTT | AGGTGTAACA | TCTATTCCAC | 540 |
| AATCTGTTTT | AGCAAGCGGC | TTACAAGGAA | TGGATGTAGT | ACACGGCACA | GCCACTATGC | 600 |
| AAGTAGATGG | TAATAAAACC | ATTATCCGCA | ACAGTGTTGA | CGCTATCATT | AATTGGAAAC | 660 |
| AATTTAACAT | CGACCAAAAT | GAAATGGTGC | AGTTTTTACA | AGAAAACAAC | AACTCCGCCG | 720 |
| TATTCAACCG | TGTTACATCT | AACCAAATCT | CCCAATTAAA | AGGGATTTTA | GATTCTAACG | 780 |
| GACAAGTCTT | TTTAATCAAC | CCAAATGGTA | TCACAATAGG | TAAAGACGCA | ATTATTAACA | 840 |
| CTAATGGCTT | TACGGCTTCT | ACGCTAGACA | TTTCTAACGA | AAACATCAAG | GCGCGTAATT | 900 |
| TCACCTTCGA | GCAAACCAAA | GATAAAGCGC | TCGCTGAAAT | TGTGAATCAC | GGTTTAATTA | 960 |
| CTGTCGGTAA | AGACGGCAGT | GTAAATCTTA | TTGGTGGCAA | AGTGAAAAAC | GAGGGTGTGA | 1020 |
| TTAGCGTAAA | TGGTGGCAGC | ATTTCTTTAC | TCGCAGGGCA | AAAAATCACC | ATCAGCGATA | 1080 |
| TAATAAACCC | AACCATTACT | TACAGCATTG | CCGCGCCTGA | AAATGAAGCG | GTCAATCTGG | 1140 |
| GCGATATTTT | TGCCAAGGC | GGTAACATTA | ATGTCCGTGC | TGCCACTATT | CGAAACCAAG | 1200 |
| CTTTCCGCCA | AAGAGGGTGA | AGCGGAAATT | GGCGGTGTAA | TTTCCGCTCA | AAATCAGCAA | 1260 |
| GCTAAAGGCG | GCAAGCTGAT | GATTACAGGC | GATAAAGTCA | CATTAAAAAC | AGGTGCAGTT | 1320 |
| ATCGACCTTT | CAGGTAAAGA | AGGGGGAGAA | ACTTACCTTG | GCGGTGACGA | GCGCGGCGAA | 1380 |
| GGTAAAAACG | GCATTCAATT | AGCAAAGAAA | ACCTCTTTAG | AAAAAGGCTC | AACCATCAAT | 1440 |
| GTATCAGGCA | AAGAAAAAGG | CGGACGCGCT | ATTGTGTGGG | GCGATATTGC | GTTAATTGAC | 1500 |
| GGCAATATTA | ACGCTCAAGG | TAGTGGTGAT | ATCGCTAAAA | CCGGTGGTTT | TGTGGAGACG | 1560 |
| TCGGGGCATG | ATTTATTCAT | CAAAGACAAT | GCAATTGTTG | ACGCCAAAGA | GTGGTTGTTA | 1620 |
| GACCCGGATA | ATGTATCTAT | TAATGCAGAA | ACAGCAGGAC | GCAGCAATAC | TTCAGAAGAC | 1680 |
| GATGAATACA | CGGGATCCGG | GAATAGTGCC | AGCACCCCAA | AACGAAACAA | AGAAAAGACA | 1740 |
| ACATTAACAA | ACACAACTCT | TGAGAGTATA | CTAAAAAAAG | GTACCTTTGT | TAACATCACT | 1800 |
| GCTAATCAAC | GCATCTATGT | CAATAGCTCC | ATTAATTTAT | CCAATGGCAG | CTTAACTCTT | 1860 |
| TGGAGTGAGG | GTCGGAGCGG | TGGCGGCGTT | GAGATTAACA | ACGATATTAC | CACCGGTGAT | 1920 |
| GATACCAGAG | GTGCAAACTT | AACAATTTAC | TCAGGCGGCT | GGGTTGATGT | TCATAAAAAT | 1980 |
| ATCTCACTCG | GGGCGCAAGG | TAACATAAAC | ATTACAGCTA | AACAAGATAT | CGCCTTTGAG | 2040 |
| AAAGGAAGCA | ACCAAGTCAT | TACAGGTCAA | GGGACTATTA | CCTCAGGCAA | TCAAAAGGT | 2100 |
| TTTAGATTTA | ATAATGTCTC | TCTAAACGGC | ACTGGCAGCG | GACTGCAATT | CACCACTAAA | 2160 |
| AGAACCAATA | AATACGCTAT | CACAAATAAA | TTTGAAGGGA | CTTTAAATAT | TTCAGGGAAA | 2220 |
| GTGAACATCT | CAATGGTTTT | ACCTAAAAAT | GAAAGTGGAT | ATGATAAATT | CAAAGGACGC | 2280 |
| ACTTACTGGA | ATTTAACCTC | GAAAGTGGAT | ATGATAAATT | CAAAGGACGC | CCTCACTATT | 2340 |
| GACTCCAGAG | GAAGCGATAG | TGCAGGCACA | CTTACCCAGC | CTTATAATTT | AAACGGTATA | 2400 |

| | | | | | | |
|---|---|---|---|---|---|---|
| TCATTCAACA | AAGACACTAC | CTTTAATGTT | GAACGAAATG | CAAGAGTCAA | CTTTGACATC | 2460 |
| AAGGCACCAA | TAGGGATAAA | TAAGTATTCT | AGTTTGAATT | ACGCATCATT | TAATGGAAAC | 2520 |
| ATTTCAGTTT | CGGGAGGGGG | GAGTGTTGAT | TTCACACTTC | TCGCCTCATC | CTCTAACGTC | 2580 |
| CAAACCCCCG | GTGTAGTTAT | AAATTCTAAA | TACTTTAATG | TTTCAACAGG | GTCAAGTTTA | 2640 |
| AGATTTAAAA | CTTCAGGCTC | AACAAAAACT | GGCTTCTCAA | TAGAGAAAGA | TTTAACTTTA | 2700 |
| AATGCCACCG | GAGGCAACAT | AACACTTTTG | CAAGTTGAAG | GCACCGATGG | AATGATTGGT | 2760 |
| AAAGGCATTG | TAGCCAAAAA | AAACATAACC | TTTGAAGGAG | GTAAGATGAG | GTTTGGCTCC | 2820 |
| AGGAAAGCCG | TAACAGAAAT | CGAAGGCAAT | GTTACTATCA | ATAACAACGC | TAACGTCACT | 2880 |
| CTTATCGGTT | CGGATTTTGA | CAACCATCAA | AAACCTTTAA | CTATTAAAAA | AGATGTCATC | 2940 |
| ATTAATAGCG | GCAACCTTAC | CGCTGGAGGC | AATATTGTCA | ATATAGCCGG | AAATCTTACC | 3000 |
| GTTGAAAGTA | ACGCTAATTT | CAAAGCTATC | ACAAATTTCA | CTTTTAATGT | AGGCGGCTTG | 3060 |
| TTTGACAACA | AAGGCAATTC | AAATATTTCC | ATTGCCAAAG | GAGGGGCTCG | CTTTAAAGAC | 3120 |
| ATTGATAATT | CCAAGAATTT | AAGCATCACC | ACCAACTCCA | GCTCCACTTA | CCGCACTATT | 3180 |
| ATAAGCGGCA | ATATAACCAA | TAAAAACGGT | GATTTAAATA | TTACGAACGA | AGGTAGTGAT | 3240 |
| ACTGAAATGC | AAATTGGCGG | CGATGTCTCG | CAAAAAGAAG | GTAATCTCAC | GATTTCTTCT | 3300 |
| GACAAAATCA | ATATTACCAA | ACAGATAACA | ATCAAGGCAG | GTGTTGATGG | GGAGAATTCC | 3360 |
| GATTCAGACG | CGACAAACAA | TGCCAATCTA | ACCATTAAAA | CCAAAGAATT | GAAATTAACG | 3420 |
| CAAGACCTAA | ATATTTCAGG | TTTCAATAAA | GCAGAGATTA | CAGCTAAAGA | TGGTAGTGAT | 3480 |
| TTAACTATTG | GTAACACCAA | TAGTGCTGAT | GGTACTAATG | CCAAAAAAGT | AACCTTTAAC | 3540 |
| CAGGTTAAAG | ATTCAAAAAT | CTCTGCTGAC | GGTCACAAGG | TGACACTACA | CAGCAAAGTG | 3600 |
| GAAACATCCG | GTAGTAATAA | CAACACTGAA | GATAGCAGTG | ACAATAATGC | CGGCTTAACT | 3660 |
| ATCGATGCAA | AAAATGTAAC | AGTAAACAAC | AATATTACTT | CTCACAAAGC | AGTGAGCATC | 3720 |
| TCTGCGACAA | GTGGAGAAAT | TACCACTAAA | ACAGGTACAA | CCATTAACGC | AACCACTGGT | 3780 |
| AACGTGGAGA | TAACCGCTCA | AACAGGTAGT | ATCCTAGGTG | GAATTGAGTC | CAGCTCTGGC | 3840 |
| TCTGTAACAC | TTACTGCAAC | CGAGGGCGCT | CTTGCTGTAA | GCAATATTTC | GGGCAACACC | 3900 |
| GTTACTGTTA | CTGCAAATAG | CGGTGCATTA | ACCACTTTGG | CAGGCTCTAC | AATTAAAGGA | 3960 |
| ACCGAGAGTG | TAACCACTTC | AAGTCAATCA | GGCGATATCG | GCGGTACGAT | TTCTGGTGGC | 4020 |
| ACAGTAGAGG | TTAAAGCAAC | CGAAAGTTTA | ACCACTCAAT | CCAATTCAAA | AATTAAAGCA | 4080 |
| ACAACAGGCG | AGGCTAACGT | AACAAGTGCA | ACAGGTACAA | TTGGTGGTAC | GATTTCCGGT | 4140 |
| AATACGGTAA | ATGTTACGGC | AAACGCTGGC | GATTTAACAG | TTGGGAATGG | CGCAGAAATT | 4200 |
| AATGCGACAG | AAGGAGCTGC | AACCTTAACT | ACATCATCGG | GCAAATTAAC | TACCGAAGCT | 4260 |
| AGTTCACACA | TTACTTCAGC | CAAGGGTCAG | GTAAATCTTT | CAGCTCAGGA | TGGTAGCGTT | 4320 |
| GCAGGAAGTA | TTAATGCCGC | CAATGTGACA | CTAAATACTA | CAGGCACTTT | AACTACCGTG | 4380 |
| AAGGGTTCAA | ACATTAATGC | AACCAGCGGT | ACCTTGGTTA | TTAACGCAAA | AGACGCTGAG | 4440 |
| CTAAATGGCG | CAGCATTGGG | TAACCACACA | GTGGTAAATG | CAACCAACGC | AAATGGCTCC | 4500 |
| GGCAGCGTAA | TCGCGACAAC | CTCAAGCAGA | GTGAACATCA | CTGGGGATTT | AATCACAATA | 4560 |
| AATGGATTAA | ATATCATTTC | AAAAAACGGT | ATAAACACCG | TACTGTTAAA | AGGCGTTAAA | 4620 |
| ATTGATGTGA | AATACATTCA | ACCGGGTATA | GCAAGCGTAG | ATGAAGTAAT | TGAAGCGAAA | 4680 |
| CGCATCCTTG | AGAAGGTAAA | AGATTTATCT | GATGAAGAAA | GAGAAGCGTT | AGCTAAACTT | 4740 |
| GGCGTAAGTG | CTGTACGTTT | TATTGAGCCA | AATAATACAA | TTACAGTCGA | TACACAAAAT | 4800 |

| | | | | | | |
|---|---|---|---|---|---|---|
| GAATTTGCAA | CCAGACCATT | AAGTCGAATA | GTGATTTCTG | AAGGCAGGGC | GTGTTTCTCA | 4860 |
| AACAGTGATG | GCGCGACGGT | GTGCGTTAAT | ATCGCTGATA | ACGGGCGGTA | GCGGTCAGTA | 4920 |
| ATTGACAAGG | TAGATTTCAT | CCTGCAATGA | AGTCATTTTA | TTTTCGTATT | ATTTACTGTG | 4980 |
| TGGGTTAAAG | TTCAGTACGG | GCTTTACCCA | TCTTGTAAAA | AATTACGGAG | AATACAATAA | 5040 |
| AGTATTTTTA | ACAGGTTATT | ATTATGAAAA | ATATAAAAG | CAGATTAAAA | CTCAGTGCAA | 5100 |
| TATCAGTATT | GCTTGGCCTG | GCTTCTTCAT | CATTGTATGC | AGAAGAAGCG | TTTTTAGTAA | 5160 |
| AAGGCTTTCA | GTTATCTGGT | GCACTTGAAA | CTTAAGTGA | AGACGCCCAA | CTGTCTGTAG | 5220 |
| CAAAATCTTT | ATCTAAATAC | CAAGGCTCGC | AAACTTTAAC | AAACCTAAAA | ACAGCACAGC | 5280 |
| TTGAATTACA | GGCTGTGCTA | GATAAGATTG | AGCCAAATAA | GTTTGATGTG | ATATTGCCAC | 5340 |
| AACAAACCAT | TACGGATGGC | AATATTATGT | TTGAGCTAGT | CTCGAAATCA | GCCGCAGAAA | 5400 |
| GCCAAGTTTT | TTATAAGGCG | AGCCAGGGTT | ATAGTGAAGA | AAATATCGCT | CGTAGCCTGC | 5460 |
| CATCTTTGAA | ACAAGGAAAA | GTGTATGAAG | ATGGTCGTCA | GTGGTTCGAT | TTGCGTGAAT | 5520 |
| TCAATATGGC | AAAAGAAAAT | CCACTTAAAG | TCACTCGCGT | GCATTACGAG | TTAAACCCTA | 5580 |
| AAAACAAAAC | CTCTGATTTG | GTAGTTGCAG | GTTTTCGCC | TTTTGGCAAA | ACGCGTAGCT | 5640 |
| TTGTTTCCTA | TGATAATTTC | GGCGCAAGGG | AGTTTAACTA | TCAACGTGTA | AGTCTAGGTT | 5700 |
| TTGTAAATGC | CAATTTGACC | GGACATGATG | ATGTATTAAA | TCTAAACGCA | TTGACCAATG | 5760 |
| TAAAAGCACC | ATCAAAATCT | TATGCGGTAG | GCATAGGATA | TACTTATCCG | TTTTATGATA | 5820 |
| AACACCAATC | CTTAAGTCTT | TATACCAGCA | TGAGTTATGC | TGATTCTAAT | GATATCGACG | 5880 |
| GCTTACCAAG | TGCGATTAAT | CGTAAATTAT | CAAAAGGTCA | ATCTATCTCT | GCGAATCTGA | 5940 |
| AATGGAGTTA | TTATCTCCCG | ACATTTAACC | TTGGAATGGA | AGACCAGTTT | AAAATTAATT | 6000 |
| TAGGCTACAA | CTACCGCCAT | ATTAATCAAA | CATCCGAGTT | AAACACCCTG | GGTGCAACGA | 6060 |
| AGAAAAATT | TGCAGTATCA | GGCGTAAGTG | CAGGCATTGA | TGGACATATC | CAATTTACCC | 6120 |
| CTAAAACAAT | CTTTAATATT | GATTTAACTC | ATCATTATTA | CGCGAGTAAA | TTACCAGGCT | 6180 |
| CTTTTGGAAT | GGAGCGCATT | GGCGAAACAT | TTAATCGCAG | CTATCACATT | AGCACAGCCA | 6240 |
| GTTTAGGGTT | GAGTCAAGAG | TTTGCTCAAG | GTTGGCATTT | TAGCAGTCAA | TTATCGGGTC | 6300 |
| AGTTTACTCT | ACAAGATATA | AGTAGCATAG | ATTTATTCTC | TGTAACAGGT | ACTTATGGCG | 6360 |
| TCAGAGGCTT | TAAATACGGC | GGTGCAAGTG | GTGAGCGCGG | TCTTGTATGG | CGTAATGAAT | 6420 |
| TAAGTATGCC | AAAATACACC | CGCTTTCAAA | TCAGCCCTTA | TGCGTTTTAT | GATGCAGGTC | 6480 |
| AGTTCCGTTA | TAATAGCGAA | AATGCTAAAA | CTTACGGCGA | AGATATGCAC | ACGGTATCCT | 6540 |
| CTGCGGGTTT | AGGCATTAAA | ACCTCTCCTA | CACAAAACTT | AAGCTTAGAT | GCTTTTGTTG | 6600 |
| CTCGTCGCTT | TGCAAATGCC | AATAGTGACA | ATTTGAATGG | CAACAAAAAA | CGCACAAGCT | 6660 |
| CACCTACAAC | CTTCTGGGGT | AGATTAACAT | TCAGTTTCTA | ACCCTGAAAT | TTAATCAACT | 6720 |
| GGTAAGCGTT | CCGCCTACCA | GTTTATAACT | ATATGCTTTA | CCCGCCAATT | TACAGTCTAT | 6780 |
| ACGCAACCCT | GTTTTCATCC | TTATATATCA | AACAAACTAA | GCAAACCAAG | CAAACCAAGC | 6840 |
| AAACCAAGCA | AACCAAGCAA | ACCAAGCAAA | CCAAGCAAAC | CAAGCAAACC | AAGCAAACCA | 6900 |
| AGCAAACCAA | GCAAACCAAG | CAAACCAAGC | AAACCAAGCA | ATGCTAAAAA | ACAATTTATA | 6960 |
| TGATAAACTA | AAACATACTC | CATACCATGG | CAATACAAGG | GATTTAATAA | TATGACAAAA | 7020 |
| GAAAATTTAC | AAAGTGTTCC | ACAAAATACG | ACCGCTTCAC | TTGTAGAATC | AAACAACGAC | 7080 |
| CAAACTTCCC | TGCAAATACT | TAAACAACCA | CCCAAACCCA | ACCTATTACG | CCTGGAACAA | 7140 |
| CATGTCGCCA | AAAAAGATTA | TGAGCTTGCT | TGCCGCGAAT | TAATGGCGAT | TTTGGAAAAA | 7200 |

```
ATGGACGCTA ATTTTGGAGG CGTTCACGAT ATTGAATTTG ACGCACCTGC TCAGCTGGCA   7260
TATCTACCCG AAAAACTACT AATTCATTTT GCCACTCGTC TCGCTAATGC AATTACAACA   7320
CTCTTTTCCG ACCCCGAATT GGCAATTTCC GAAGAAGGGG CATTAAAGAT GATTAGCCTG   7380
CAACGCTGGT TGACGCTGAT TTTTGCCTCT TCCCCCTACG TTAACGCAGA CCATATTCTC   7440
AATAAATATA ATATCAACCC AGATTCCGAA GGTGGCTTTC ATTTAGCAAC AGACAACTCT   7500
TCTATTGCTA AATTCTGTAT TTTTACTTA CCCGAATCCA ATGTCAATAT GAGTTTAGAT   7560
GCGTTATGGG CAGGGAATCA ACAACTTTGT GCTTCATTGT GTTTTGCGTT GCAGTCTTCA   7620
CGTTTTATTG GTACTGCATC TGCGTTTCAT AAAAGAGCGG TGGTTTTACA GTGGTTTCCT   7680
AAAAAACTCG CCGAAATTGC TAATTTAGAT GAATTGCCTG CAAATATCCT TCATGATGTA   7740
TATATGCACT GCAGTTATGA TTTAGCAAAA AACAAGCACG ATGTTAAGCG TCCATTAAAC   7800
GAACTTGTCC GCAAGCATAT CCTCACGCAA GGATGGCAAG ACCGCTACCT TTACACCTTA   7860
GGTAAAAAGG ACGGCAAACC TGTGATGATG GTACTGCTTG AACATTTTAA TTCGGGACAT   7920
TCGATTTATC GCACGCATTC AACTTCAATG ATTGCTGCTC GAGAAAAATT CTATTTAGTC   7980
GGCTTAGGCC ATGAGGGCGT TGATAACATA GGTCGAGAAG TGTTTGACGA GTTCTTTGAA   8040
ATCAGTAGCA ATAATATAAT GGAGAGACTG TTTTTTATCC GTAAACAGTG CGAAACTTTC   8100
CAACCCGCAG TGTTCTATAT GCCAAGCATT GGCATGGATA TTACCACGAT TTTTGTGAGC   8160
AACACTCGGC TTGCCCCTAT TCAAGCTGTA GCCTTGGGTC ATCCTGCCAC TACGCATTCT   8220
GAATTTATTG ATTATGTCAT CGTAGAAGAT GATTATGTGG GCAGTGAAGA TTGTTTTAGC   8280
GAAACCCTTT TACGCTTACC CAAAGATGCC CTACCTTATG TACCATCTGC ACTCGCCCCA   8340
CAAAAGTGG ATTATGTACT CAGGGAAAAC CCTGAAGTAG TCAATATCGG TATTGCCGCT   8400
ACCACAATGA AATTAAACCC TGAATTTTTG CTAACATTGC AAGAAATCAG AGATAAAGCT   8460
AAAGTCAAAA TACATTTTCA TTTCGCACTT GGACAATCAA CAGGCTTGAC ACACCCTTAT   8520
GTCAAATGGT TTATCGAAAG CTATTTAGGT GACGATGCCA CTGCACATCC CCACGCACCT   8580
TATCACGATT ATCTGGCAAT ATTGCGTGAT TGCGATATGC TACTAAATCC GTTTCCTTTC   8640
GGTAATACTA ACGGCATAAT TGATATGGTT ACATTAGGTT TAGTTGGTGT ATGCAAAACG   8700
GGGGATGAAG TACATGAACA TATTGATGAA GGTCTGTTTA AACGCTTAGG ACTACCAGAA   8760
TGGCTGATAG CCGACACACG AGAAACATAT ATTGAATGTG CTTTGCGTCT AGCAGAAAAC   8820
CATCAAGAAC GCCTTGAACT CCGTCGTTAC ATCATAGAAA CAACGGCTT ACAAAAGCTT   8880
TTTACAGGCG ACCCTCGTCC ATTGGGCAAA ATACTGCTTA AGAAAACAAA TGAATGGAAG   8940
CGGAAGCACT TGAGTAAAAA ATAACGGTTT TTTAAAGTAA AAGTGCGGTT AATTTTCAAA   9000
GCGTTTTAAA AACCTCTCAA AAATCAACCG CACTTTTATC TTTATAACGC TCCCGCGCGC   9060
TGACAGTTTA TCTCTTTCTT AAAATACCCA TAAAATTGTG GCAATAGTTG GGTAATCAAA   9120
TTCAATTGTT GATACGGCAA ACTAAAGACG GCGCGTTCTT CGGCAGTCAT C            9171
```

( 2 ) INFORMATION FOR SEQ ID NO:6:

( i ) SEQUENCE CHARACTERISTICS:
        ( A ) LENGTH: 9323 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
CGCCACTTCA ATTTTGGATT GTTGAAATTC AACTAACCAA AAAGTGCGGT TAAAATCTGT     60
```

-continued

| | | | | | | |
|---|---|---|---|---|---|---|
| GGAGAAAATA | GGTTGTAGTG | AAGAACGAGG | TAATTGTTCA | AAAGGATAAA | GCTCTCTTAA | 120 |
| TTGGGCATTG | GTTGGCGTTT | CTTTTTCGGT | TAATAGTAAA | TTATATTCTG | GACGACTATG | 180 |
| CAATCCACCA | ACAACTTTAC | CGTTGGTTTT | AAGCGTTAAT | GTAAGTTCTT | GCTCTTCTTG | 240 |
| GCGAATACGT | AATCCCATTT | TTTGTTTAGC | AAGAAAATGA | TCGGGATAAT | CATAATAGGT | 300 |
| GTTGCCCAAA | AATAAATTTT | GATGTTCTAA | AATCATAAAT | TTTGCAAGAT | ATTGTGGCAA | 360 |
| TTCAATACCT | ATTTGTGGCG | AAATCGCCAA | TTTAATTCA | ATTTCTTGTA | GCATAATATT | 420 |
| TCCCACTCAA | ATCAACTGGT | TAAATATACA | AGATAATAAA | AATAAATCAA | GATTTTGTG | 480 |
| ATGACAAACA | ACAATTACAA | CACCTTTTTT | GCAGTCTATA | TGCAAATATT | TTAAAAAAT | 540 |
| AGTATAAATC | CGCCATATAA | AATGGTATAA | TCTTTCATCT | TTCATCTTTC | ATCTTTCATC | 600 |
| TTTCATCTTT | CATCTTTCAT | CTTTCATCTT | TCATCTTTCA | TCTTTCATCT | TTCATCTTTC | 660 |
| ATCTTTCATC | TTTCATCTTT | CACATGAAAT | GATGAACCGA | GGGAAGGGAG | GGAGGGGCAA | 720 |
| GAATGAAGAG | GGAGCTGAAC | GAACGCAAAT | GATAAAGTAA | TTTAATTGTT | CAACTAACCT | 780 |
| TAGGAGAAAA | TATGAACAAG | ATATATCGTC | TCAAATTCAG | CAAACGCCTG | AATGCTTTGG | 840 |
| TTGCTGTGTC | TGAATTGGCA | CGGGGTTGTG | ACCATTCCAC | AGAAAAGGC | AGCGAAAAC | 900 |
| CTGCTCGCAT | GAAAGTGCGT | CACTTAGCGT | TAAAGCCACT | TTCCGCTATG | TTACTATCTT | 960 |
| TAGGTGTAAC | ATCTATTCCA | CAATCTGTTT | TAGCAAGCGG | CAATTTAACA | TCGACCAAAA | 1020 |
| TGAAATGGTG | CAGTTTTTAC | AAGAAAACAA | GTAATAAAAC | CATTATCCGC | AACAGTGTTG | 1080 |
| ACGCTATCAT | TAATTGGAAA | CAATTTAACA | TCGACCAAAA | TGAAATGGTG | CAGTTTTTAC | 1140 |
| AAGAAAACAA | CAACTCCGCC | GTATTCAACC | GTGTTACATC | TAACCAAATC | TCCCAATTAA | 1200 |
| AAGGGATTTT | AGATTCTAAC | GGACAAGTCT | TTTTAATCAA | CCCAAATGGT | ATCACAATAG | 1260 |
| GTAAAGACGC | AATTATTAAC | ACTAATGGCT | TTACGGCTTC | TACGCTAGAC | ATTTCTAACG | 1320 |
| AAAACATCAA | GGCGCGTAAT | TTCACCTTCG | AGCAAACCAA | AGATAAAGCG | CTCGCTGAAA | 1380 |
| TTGTGAATCA | CGGTTTAATT | ACTGTCGGTA | AAGACGGCAG | TGTAAATCTT | ATTGGTGGCA | 1440 |
| AAGTGAAAAA | CGAGGGTGTG | ATTAGCGTAA | ATGGTGGCAG | CATTTCTTTA | CTCGCAGGGC | 1500 |
| AAAAAATCAC | CATCAGCGAT | ATAATAAACC | CAACCATTAC | TTACAGCATT | GCCGCGCCTG | 1560 |
| AAAATGAAGC | GGTCAATCTG | GCGATATTT | TTGCCAAAGG | CGGTAACATT | AATGTCCGTG | 1620 |
| CTGCCACTAT | TCGAAACCAA | GGTAAACTTT | CTGCTGATTC | TGTAAGCAAA | GATAAAGCG | 1680 |
| GCAATATTGT | TCTTTCCGCC | AAAGAGGGTG | AAGCGGAAAT | TGGCGGTGTA | ATTTCCGCTC | 1740 |
| AAAATCAGCA | AGCTAAAGGC | GGCAAGCTGA | TGATAAAGTC | CGATAAAGTC | ACATTAAAAA | 1800 |
| CAGGTGCAGT | TATCGACCTT | TCAGGTAAAG | AAGGGGGAGA | AACTTACCTT | GGCGGTGACG | 1860 |
| AGCGCGGCGA | AGGTAAAAAC | GGCATTCAAT | TAGCAAAGAA | AACCTCTTTA | GAAAAGGCT | 1920 |
| CAACCATCAA | TGTATCAGGC | AAAGAAAAG | GCGGACGCGC | TATTGTGTGG | GGCGATATTG | 1980 |
| CGTTAATTGA | CGGCAATATT | AACGCTCAAG | GTAGTGGTGA | TATCGCTAAA | ACCGGTGGTT | 2040 |
| TTGTGGAGAC | ATCGGGGCAT | TATTTATCCA | TTGACAGCAA | TGCAATTGTT | AAAACAAAAG | 2100 |
| AGTGGTTGCT | AGACCCTGAT | GATGTAACAA | TTGAAGCCGA | AGACCCCTT | CGCAATAATA | 2160 |
| CCGGTATAAA | TGATGAATTC | CCAACAGGCA | CCGGTGAAGC | AAGCGACCCT | AAAAAAAATA | 2220 |
| GCGAACTCAA | AACAACGCTA | ACCAATACAA | CTATTTCAAA | TTATCTGAAA | AACGCCTGGA | 2280 |
| CAATGAATAT | AACGGCATCA | AGAAAACTTA | CCGTTAATAG | CTCAATCAAC | ATCGGAAGCA | 2340 |
| ACTCCCACTT | AATTCTCCAT | AGTAAAGGTC | AGCGTGGCGG | AGGCGTTCAG | ATTGATGGAG | 2400 |
| ATATTACTTC | TAAAGGCGGA | AATTTAACCA | TTTATTCTGG | CGGATGGGTT | GATGTTCATA | 2460 |

-continued

| | | | | | | |
|---|---|---|---|---|---|---|
| AAAATATTAC | GCTTGATCAG | GGTTTTTTAA | ATATTACCGC | CGCTTCCGTA | GCTTTTGAAG | 2520 |
| GTGGAAATAA | CAAAGCACGC | GACGCGGCAA | ATGCTAAAAT | TGTCGCCCAG | GGCACTGTAA | 2580 |
| CCATTACAGG | AGAGGGAAAA | GATTTCAGGG | CTAACAACGT | ATCTTTAAAC | GGAACGGGTA | 2640 |
| AAGGTCTGAA | TATCATTTCA | TCAGTGAATA | ATTTAACCCA | CAATCTTAGT | GGCACAATTA | 2700 |
| ACATATCTGG | GAATATAACA | ATTAACCAAA | CTACGAGAAA | GAACACCTCG | TATTGGCAAA | 2760 |
| CCAGCCATGA | TTCGCACTGG | AACGTCAGTG | CTCTTAATCT | AGAGACAGGC | GCAAATTTTA | 2820 |
| CCTTTATTAA | ATACATTTCA | AGCAATAGCA | AAGGCTTAAC | AACACAGTAT | AGAAGCTCTG | 2880 |
| CAGGGGTGAA | TTTTAACGGC | GTAAATGGCA | ACATGTCATT | CAATCTCAAA | GAAGGAGCGA | 2940 |
| AAGTTAATTT | CAAATTAAAA | CCAAACGAGA | ACATGAACAC | AAGCAAACCT | TTACCAATTC | 3000 |
| GGTTTTTAGC | CAATATCACA | GCCACTGGTG | GGGGCTCTGT | TTTTTTTGAT | ATATATGCCA | 3060 |
| ACCATTCTGG | CAGAGGGGCT | GAGTTAAAAA | TGAGTGAAAT | TAATATCTCT | AACGGCGCTA | 3120 |
| ATTTTACCTT | AAATTCCCAT | GTTCGCGGCG | ATGACGCTTT | TAAAATCAAC | AAAGACTTAA | 3180 |
| CCATAAATGC | AACCAATTCA | AATTTCAGCC | TCAGACAGAC | GAAAGATGAT | TTTTATGACG | 3240 |
| GGTACGCACG | CAATGCCATC | AATTCAACCT | ACAACATATC | CATTCTGGGC | GGTAATGTCA | 3300 |
| CCCTTGGTGG | ACAAAACTCA | AGCAGCAGCA | TTACGGGGAA | TATTACTATC | GAGAAAGCAG | 3360 |
| CAAATGTTAC | GCTAGAAGCC | AATAACGCCC | CTAATCAGCA | AAACATAAGG | GATAGAGTTA | 3420 |
| TAAAACTTGG | CAGCTTGCTC | GTTAATGGGA | GTTAAGTTT | AACTGGCGAA | AATGCAGATA | 3480 |
| TTAAAGGCAA | TCTCACTATT | TCAGAAAGCG | CCACTTTTAA | AGGAAAGACT | AGAGATACCC | 3540 |
| TAAATATCAC | CGGCAATTTT | ACCAATAATG | GCACTGCCGA | AATTAATATA | ACACAAGGAG | 3600 |
| TGGTAAAACT | TGGCAATGTT | ACCAATGATG | GTGATTTAAA | CATTACCACT | CACGCTAAAC | 3660 |
| GCAACCAAAG | AAGCATCATC | GGCGGAGATA | TAATCAACAA | AAAAGGAAGC | TTAAATATTA | 3720 |
| CAGACAGTAA | TAATGATGCT | GAAATCCAAA | TTGGCGGCAA | TATCTCGCAA | AAAGAAGGCA | 3780 |
| ACCTCACGAT | TTCTTCCGAT | AAAATTAATA | TCACCAAACA | GATAACAATC | AAAAAGGGTA | 3840 |
| TTGATGGAGA | GGACTCTAGT | TCAGATGCGA | CAAGTAATGC | CAACCTAACT | ATTAAAACCA | 3900 |
| AAGAATTGAA | ATTGACAGAA | GACCTAAGTA | TTTCAGGTTT | CAATAAAGCA | GAGATTACAG | 3960 |
| CCAAAGATGG | TAGAGATTTA | ACTATTGGCA | ACAGTAATGA | CGGTAACAGC | GGTGCCGAAG | 4020 |
| CCAAAACAGT | AACTTTTAAC | AATGTTAAAG | ATTCAAAAAT | CTCTGCTGAC | GGTCACAATG | 4080 |
| TGACACTAAA | TAGCAAAGTG | AAAACATCTA | GCAGCAATGG | CGGACGTGAA | AGCAATAGCG | 4140 |
| ACAACGATAC | CGGCTTAACT | ATTACTGCAA | AAAATGTAGA | AGTAAACAAA | GATATTACTT | 4200 |
| CTCTCAAAAC | AGTAAATATC | ACCGCGTCGG | AAAAGGTTAC | CACCACAGCA | GGCTCGACCA | 4260 |
| TTAACGCAAC | AAATGGCAAA | GCAAGTATTA | CAACCAAAAC | AGGTGATATC | AGCGGTACGA | 4320 |
| TTTCCGGTAA | CACGGTAAGT | GTTAGCGCGA | CTGGTGATTT | AACCACTAAA | TCCGGCTCAA | 4380 |
| AAATTGAAGC | GAAATCGGGT | GAGGCTAATG | TAACAAGTGC | AACAGGTACA | ATTGGCGGTA | 4440 |
| CAATTTCCGG | TAATACGGTA | AATGTTACGG | CAAACGCTGG | CGATTTAACA | GTTGGGAATG | 4500 |
| GCGCAGAAAT | TAATGCGACA | GAAGGAGCTG | CAACCTTAAC | CGCAACAGGG | AATACCTTGA | 4560 |
| CTACTGAAGC | CGGTTCTAGC | ATCACTTCAA | CTAAGGGTCA | GGTAGACCTC | TTGGCTCAGA | 4620 |
| ATGGTAGCAT | CGCAGGAAGC | ATTAATGCTG | CTAATGTGAC | ATTAAATACT | ACAGGCACCT | 4680 |
| TAACCACCGT | GGCAGGCTCG | GATATTAAAG | CAACCAGCGG | CACCTTGGTT | ATTAACGCAA | 4740 |
| AAGATGCTAA | GCTAAATGGT | GATGCATCAG | GTGATAGTAC | AGAAGTGAAT | GCAGTCAACG | 4800 |
| ACTGGGGATT | TGGTAGTGTG | ACTGCGGCAA | CCTCAAGCAG | TGTGAATATC | ACTGGGGATT | 4860 |

```
TAAACACAGT  AAATGGGTTA  AATATCATTT  CGAAAGATGG  TAGAAACACT  GTGCGCTTAA   4920
GAGGCAAGGA  AATTGAGGTG  AAATATATCC  AGCCAGGTGT  AGCAAGTGTA  GAAGAAGTAA   4980
TTGAAGCGAA  ACGCGTCCTT  GAAAAAGTAA  AAGATTTATC  TGATGAAGAA  AGAGAAACAT   5040
TAGCTAAACT  TGGTGTAAGT  GCTGTACGTT  TTGTTGAGCC  AAATAATACA  ATTACAGTCA   5100
ATACACAAAA  TGAATTTACA  ACCAGACCGT  CAAGTCAAGT  GATAATTTCT  GAAGGTAAGG   5160
CGTGTTTCTC  AAGTGGTAAT  GGCGCACGAG  TATGTACCAA  TGTTGCTGAC  GATGGACAGC   5220
CGTAGTCAGT  AATTGACAAG  GTAGATTTCA  TCCTGCAATG  AAGTCATTTT  ATTTTCGTAT   5280
TATTTACTGT  GTGGGTTAAA  GTTCAGTACG  GGCTTTACCC  ATCTTGTAAA  AAATTACGGA   5340
GAATACAATA  AAGTATTTTT  AACAGGTTAT  TATTATGAAA  AATATAAAAA  GCAGATTAAA   5400
ACTCAGTGCA  ATATCAGTAT  TGCTTGGCCT  GGCTTCTTCA  TCATTGTATG  CAGAAGAAGC   5460
GTTTTTAGTA  AAAGGCTTTC  AGTTATCTGG  TGCACTTGAA  ACTTAAGTG   AAGACGCCCA   5520
ACTGTCTGTA  GCAAAATCTT  TATCTAAATA  CCAAGGCTCG  CAAACTTTAA  CAAACCTAAA   5580
AACAGCACAG  CTTGAATTAC  AGGCTGTGCT  AGATAAGATT  GAGCCAAATA  AATTTGATGT   5640
GATATTGCCG  CAACAAACCA  TTACGGATGG  CAATATCATG  TTTGAGCTAG  TCTCGAAATC   5700
AGCCGCAGAA  AGCCAAGTTT  TTTATAAGGC  GAGCCAGGGT  TATAGTGAAG  AAAATATCGC   5760
TCGTAGCCTG  CCATCTTTGA  AACAAGGAAA  AGTGTATGAA  GATGGTCGTC  AGTGGTTCGA   5820
TTTGCGTGAA  TTTAATATGG  CAAAGAAAA   CCCGCTTAAG  GTTACCCGTG  TACATTACGA   5880
ACTAAACCCT  AAAAACAAAA  CCTCTAATTT  GATAATTGCG  GGCTTCTCGC  CTTTTGGTAA   5940
AACGCGTAGC  TTTATTTCTT  ATGATAATTT  CGGCGCGAGA  GAGTTTAACT  ACCAACGTGT   6000
AAGCTTGGGT  TTTGTTAATG  CCAATTTAAC  TGGTCATGAT  GATGTGTTAA  TTATACCAGT   6060
ATGAGTTATG  CTGATTCTAA  TGATATCGAC  GGCTTACCAA  GTGCGATTAA  TCGTAAATTA   6120
TCAAAAGGTC  AATCTATCTC  TGCGAATCTG  AAATGGAGTT  ATTATCTCCC  AACATTTAAC   6180
CTTGGCATGG  AAGACCAATT  TAAAATTAAT  TTAGGCTACA  ACTACCGCCA  TATTAATCAA   6240
ACCTCCGCGT  TAAATCGCTT  GGGTGAAACG  AAGAAAAAAT  TTGCAGTATC  AGGCGTAAGT   6300
GCAGGCATTG  ATGGACATAT  CCAATTTACC  CCTAAAACAA  TCTTTAATAT  TGATTTAACT   6360
CATCATTATT  ACGCGAGTAA  ATTACCAGGC  TCTTTTGGAA  TGGAGCGCAT  TGGCGAAACA   6420
TTTAATCGCA  GCTATCACAT  TAGCACAGCC  AGTTTAGGGT  TGAGTCAAGA  GTTTGCTCAA   6480
GGTTGGCATT  TTAGCAGTCA  ATTATCAGGT  CAATTACTC   TACAAGATAT  TAGCAGTATA   6540
GATTTATTCT  CTGTAACAGG  TACTTATGGC  GTCAGAGGCT  TTAAATACGG  CGGTGCAAGT   6600
GGTGAGCGCG  TCTTGTATG   GCGTAATGAA  TTAAGTATGC  CAAAATACAC  CCGCTTCCAA   6660
ATCAGCCCTT  ATGCGTTTTA  TGATGCAGGT  CAGTTCCGTT  ATAATAGCGA  AAATGCTAAA   6720
ACTTACGGCG  AAGATATGCA  CACGGTATCC  TCTGCGGGTT  TAGGCATTAA  AACCTCTCCT   6780
ACACAAAACT  TAAGCCTAGA  TGCTTTTGTT  GCTCGTCGCT  TTGCAAATGC  CAATAGTGAC   6840
AATTTGAATG  GCAACAAAAA  ACGCACAAGC  TCACCTACAA  CCTTCTGGGG  GAGATTAACA   6900
TTCAGTTTCT  AACCCTGAAA  TTTAATCAAC  TGGTAAGCGT  TCCGCCTACC  AGTTTATAAC   6960
TATATGCTTT  ACCCGCCAAT  TTACAGTCTA  TAGGCAACCC  TGTTTTACC   CTTATATATC   7020
AAATAAACAA  GCTAAGCTGA  GCTAAGCAAA  CCAAGCAAAC  TCAAGCAAGC  CAAGTAATAC   7080
TAAAAAAACA  ATTTATATGA  TAAACTAAAG  TATACTCCAT  GCCATGGCGA  TACAAGGGAT   7140
TTAATAATAT  GACAAAAGAA  AATTTGCAAA  ACGCTCCTCA  AGATGCGACC  GCTTTACTTG   7200
CGGAATTAAG  CAACAATCAA  ACTCCCCTGC  GAATATTTAA  ACAACCACGC  AAGCCCAGCC   7260
```

```
TATTACGCTT  GGAACAACAT  ATCGCAAAAA  AAGATTATGA  GTTTGCTTGT  CGTGAATTAA    7320
TGGTGATTCT  GGAAAAAATG  GACGCTAATT  TTGGAGGCGT  TCACGATATT  GAATTTGACG    7380
CACCCGCTCA  GCTGGCATAT  CTACCCGAAA  AATTACTAAT  TTATTTTGCC  ACTCGTCTCG    7440
CTAATGCAAT  TACAACACTC  TTTTCCGACC  CCGAATTGGC  AATTTCTGAA  GAAGGGGCGT    7500
TAAAGATGAT  TAGCCTGCAA  CGCTGGTTGA  CGCTGATTTT  TGCCTCTTCC  CCCTACGTTA    7560
ACGCAGACCA  TATTCTCAAT  AAATATAATA  TCAACCCAGA  TTCCGAAGGT  GGCTTTCATT    7620
TAGCAACAGA  CAACTCTTCT  ATTGCTAAAT  TCTGTATTTT  TTACTTACCC  GAATCCAATG    7680
TCAATATGAG  TTTAGATGCG  TTATGGGCAG  GGAATCAACA  ACTTTGTGCT  TCATTGTGTT    7740
TTGCGTTGCA  GTCTTCACGT  TTTATTGGTA  CCGCATCTGC  GTTTCATAAA  AGAGCGGTGG    7800
TTTTACAGTG  GTTTCCTAAA  AAACTCGCCG  AAATTGCTAA  TTTAGATGAA  TTGCCTGCAA    7860
ATATCCTTCA  TGATGTATAT  ATGCACTGCA  GTTATGATTT  AGCAAAAAAC  AAGCACGATG    7920
TTAAGCGTCC  ATTAAACGAA  CTTGTCCGCA  AGCATATCCT  CACGCAAGGA  TGGCAAGACC    7980
GCTACCTTTA  CACCTTAGGT  AAAAAGGACG  GCAAACCTGT  GATGATGGTA  CTGCTTGAAC    8040
ATTTTAATTC  GGGACATTCG  ATTTATCGTA  CACATTCAAC  TTCAATGATT  GCTGCTCGAG    8100
AAAAATTCTA  TTTAGTCGGC  TTAGGCCATG  AGGGCGTTGA  TAAAATAGGT  CGAGAAGTGT    8160
TTGACGAGTT  CTTTGAAATC  AGTAGCAATA  ATATAATGGA  GAGACTGTTT  TTTATCCGTA    8220
AACAGTGCGA  AACTTTCCAA  CCCGCAGTGT  TCTATATGCC  AAGCATTGGC  ATGGATATTA    8280
CCACGATTTT  TGTGAGCAAC  ACTCGGCTTG  CCCCTATTCA  AGCTGTAGCC  CTGGGTCATC    8340
CTGCCACTAC  GCATTCTGAA  TTTATTGATT  ATGTCATCGT  AGAAGATGAT  TATGTGGGCA    8400
GTGAAGATTG  TTTCAGCGAA  ACCCTTTTAC  GCTTACCCAA  AGATGCCCTA  CCTTATGTAC    8460
CTTCTGCACT  CGCCCCACAA  AAAGTGGATT  ATGTACTCAG  GGAAAACCCT  GAAGTAGTCA    8520
ATATCGGTAT  TGCCGCTACC  ACAATGAAAT  TAAACCCTGA  ATTTTGCTA   ACATTGCAAG    8580
AAATCAGAGA  TAAAGCTAAA  GTCAAAATAC  ATTTTCATTT  CGCACTTGGA  CAATCAACAG    8640
GCTTGACACA  CCCTTATGTC  AAATGGTTTA  TCGAAAGCTA  TTTAGGTGAC  GATGCCACTG    8700
CACATCCCCA  CGCACCTTAT  CACGATTATC  TGGCAATATT  GCGTGATTGC  GATATGCTAC    8760
TAAATCCGTT  TCCTTTCGGT  AATACTAACG  GCATAATTGA  TATGGTTACA  TTAGGTTTAG    8820
TTGGTGTATG  CAAAACGGGG  GATGAAGTAC  ATGAACATAT  TGATGAAGGT  CTGTTTAAAC    8880
GCTTAGGACT  ACCAGAATGG  CTGATAGCCG  ACACACGAGA  AACATATATT  GAATGTGCTT    8940
TGCGTCTAGC  AGAAAACCAT  CAAGAACGCC  TTGAACTCCG  TCGTTACATC  ATAGAAAACA    9000
ACGGCTTACA  AAAGCTTTTT  ACAGGCGACC  CTCGTCCATT  GGGCAAAATA  CTGCTTAAGA    9060
AAACAAATGA  ATGGAAGCGG  AAGCACTTGA  GTAAAAAATA  ACGGTTTTTT  AAAGTAAAAG    9120
TGCGGTTAAT  TTTCAAAGCG  TTTTAAAAAC  CTCTCAAAAA  TCAACCGCAC  TTTTATCTTT    9180
ATAACGATCC  CGCACGCTGA  CAGTTTATCA  GCCTCCCGCC  ATAAAACTCC  GCCTTTCATG    9240
GCGGAGATTT  TAGCCAAAAC  TGGCAGAAAT  TAAAGGCTAA  AATCACCAAA  TTGCACCACA    9300
AAATCACCAA  TACCCACAAA  AAA                                               9323
```

( 2 ) INFORMATION FOR SEQ ID NO:7:

( i ) SEQUENCE CHARACTERISTICS:
    ( A ) LENGTH: 4287 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:7:

| | | | | | | |
|---|---|---|---|---|---|---|
| GATCAATCTG | GGCGATATTT | TTGCCAAAGG | TGGTAACATT | AATGTCCGCG | CTGCCACTAT | 60 |
| TCGCAATAAA | GGTAAACTTT | CTGCCGACTC | TGTAAGCAAA | GATAAAGTG | GTAACATTGT | 120 |
| TCTCTCTGCC | AAAGAAGGTG | AAGCGGAAAT | TGGCGGTGTA | ATTTCCGCTC | AAAATCAGCA | 180 |
| AGCCAAAGGT | GGTAAGTTGA | TGATTACAGG | CGATAAAGTT | ACATTGAAAA | CGGGTGCACT | 240 |
| TATCGACCTT | TCGGGTAAAG | AAGGGGGAGA | AACTTATCTT | GGCGGTGACG | AGCGTGGCGA | 300 |
| AGGTAAAAAC | GGCATTCAAT | TAGCAAAGAA | AACCACTTTA | GAAAAGGCT | CAACAATTAA | 360 |
| TGTGTCAGGT | AAAGAAAAG | CTGGGCGCGC | TATTGTATGG | GGCGATATTG | CGTTAATTGA | 420 |
| CGGCAATATT | AATGCCCAAG | GTAAAGATAT | CGCTAAAACT | GGTGGTTTTG | TGGAGACGTC | 480 |
| GGGGCATTAC | TTATCCATTG | ATGATAACGC | AATTGTTAAA | ACAAAAGAAT | GGCTACTAGA | 540 |
| CCCAGAGAAT | GTGACTATTG | AAGCTCCTTC | CGCTTCTCGC | GTCGAGCTGG | GTGCCGATAG | 600 |
| GAATTCCCAC | TCGGCAGAGG | TGATAAAAGT | GACCCTAAAA | AAAATAACA | CCTCCTTGAC | 660 |
| AACACTAACC | AATACAACCA | TTTCAAATCT | TCTGAAAAGT | GCCCACGTGG | TGAACATAAC | 720 |
| GGCAAGGAGA | AAACTTACCG | TTAATAGCTC | TATCAGTATA | GAAAGAGGCT | CCCACTTAAT | 780 |
| TCTCCACAGT | GAAGGTCAGG | GCGGTCAAGG | TGTTCAGATT | GATAAAGATA | TTACTTCTGA | 840 |
| AGGCGGAAAT | TTAACCATTT | ATTCTGGCGG | ATGGGTTGAT | GTTCATAAAA | ATATTACGCT | 900 |
| TGGTAGCGGC | TTTTTAAACA | TCACAACTAA | AGAAGGAGAT | ATCGCCTTCG | AAGACAAGTC | 960 |
| TGGACGGAAC | AACCTAACCA | TTACAGCCCA | AGGGACCATC | ACCTCAGGTA | ATAGTAACGG | 1020 |
| CTTTAGATTT | AACAACGTCT | CTCTAAACAG | CCTTGGCGGA | AAGCTGAGCT | TTACTGACAG | 1080 |
| CAGAGAGGAC | AGAGGTAGAA | GAACTAAGGG | TAATATCTCA | AACAAATTTG | ACGGAACGTT | 1140 |
| AAACATTTCC | GGAACTGTAG | ATATCTCAAT | GAAAGCACCC | AAAGTCAGCT | GGTTTTACAG | 1200 |
| AGACAAAGGA | CGCACCTACT | GGAACGTAAC | CACTTTAAAT | GTTACCTCGG | GTAGTAAATT | 1260 |
| TAACCTCTCC | ATTGACAGCA | CAGGAAGTGG | CTCAACAGGT | CCAAGCATAC | GCAATGCAGA | 1320 |
| ATTAAATGGC | ATAACATTTA | ATAAAGCCAC | TTTTAATATC | GCACAAGGCT | CAACAGCTAA | 1380 |
| CTTTAGCATC | AAGGCATCAA | TAATGCCCTT | TAAGAGTAAC | GCTAACTACG | CATTATTTAA | 1440 |
| TGAAGATATT | TCAGTCTCAG | GGGGGGGTAG | CGTTAATTTC | AAACTTAACG | CCTCATCTAG | 1500 |
| CAACATACAA | ACCCCTGGCG | TAATTATAAA | ATCTCAAAAC | TTTAATGTCT | CAGGAGGGTC | 1560 |
| AACTTTAAAT | CTCAAGGCTG | AAGGTTCAAC | AGAAACCGCT | TTTTCAATAG | AAAATGATTT | 1620 |
| AAACTTAAAC | GCCACCGGTG | GCAATATAAC | AATCAGACAA | GTCGAGGGTA | CCGATTCACG | 1680 |
| CGTCAACAAA | GGTGTCGCAG | CCAAAAAAAA | CATAACTTTT | AAAGGGGGTA | ATATCACCTT | 1740 |
| CGGCTCTCAA | AAAGCCACAA | CAGAAATCAA | AGGCAATGTT | ACCATCAATA | AAAACACTAA | 1800 |
| CGCTACTCTT | CGTGGTGCGA | ATTTTGCCGA | AAACAAATCG | CCTTTAAATA | TAGCAGGAAA | 1860 |
| TGTTATTAAT | AATGGCAACC | TTACCACTGC | CGGCTCCATT | ATCAATATAG | CCGGAAATCT | 1920 |
| TACTGTTTCA | AAAGGCGCTA | ACCTTCAAGC | TATAACAAAT | TACACTTTTA | ATGTAGCCGG | 1980 |
| CTCATTTGAC | AACAATGGCG | CTTCAAACAT | TTCCATTGCC | AGAGGAGGGG | CTAAATTTAA | 2040 |
| AGATATCAAT | AACACCAGTA | GCTTAAATAT | TACCACCAAC | TCTGATACCA | CTTACCGCAC | 2100 |
| CATTATAAAA | GGCAATATAT | CCAACAAATC | AGGTGATTTG | AATATTATTG | ATAAAAAAG | 2160 |
| CGACGCTGAA | ATCCAAATTG | GCGGCAATAT | CTCACAAAAA | GAAGGCAATC | TCACAATTTC | 2220 |
| TTCTGATAAA | GTAAATATTA | CCAATCAGAT | AACAATCAAA | GCAGGCGTTG | AAGGGGGGCG | 2280 |

-continued

| | | | | | |
|---|---|---|---|---|---|
| TTCTGATTCA | AGTGAGGCAG | AAAATGCTAA | CCTAACTATT | CAAACCAAAG | AGTTAAAATT | 2340
| GGCAGGAGAC | CTAAATATTT | CAGGCTTTAA | TAAAGCAGAA | ATTACAGCTA | AAAATGGCAG | 2400
| TGATTTAACT | ATTGGCAATG | CTAGCGGTGG | TAATGCTGAT | GCTAAAAAG | TGACTTTTGA | 2460
| CAAGGTTAAA | GATTCAAAAA | TCTCGACTGA | CGGTCACAAT | GTAACACTAA | ATAGCGAAGT | 2520
| GAAACGTCT | AATGGTAGTA | GCAATGCTGG | TAATGATAAC | AGCACCGGTT | TAACCATTTC | 2580
| CGCAAAAGAT | GTAACGGTAA | ACAATAACGT | TACCTCCCAC | AAGACAATAA | ATATCTCTGC | 2640
| CGCAGCAGGA | AATGTAACAA | CCAAGAAGG | CACAACTATC | AATGCAACCA | CAGGCAGCGT | 2700
| GGAAGTAACT | GCTCAAAATG | GTACAATTAA | AGGCAACATT | ACCTCGCAAA | ATGTAACAGT | 2760
| GACAGCAACA | GAAAATCTTG | TTACCACAGA | GAATGCTGTC | ATTAATGCAA | CCAGCGGCAC | 2820
| AGTAAACATT | AGTACAAAAA | CAGGGGATAT | TAAAGGTGGA | ATTGAATCAA | CTTCCGGTAA | 2880
| TGTAAATATT | ACAGCGAGCG | GCAATACACT | TAAGGTAAGT | AATATCACTG | GTCAAGATGT | 2940
| AACAGTAACA | GCGGATGCAG | GAGCCTTGAC | AACTACAGCA | GGCTCAACCA | TTAGTGCGAC | 3000
| AACAGGCAAT | GCAAATATTA | CAACCAAAAC | AGGTGATATC | AACGGTAAAG | TTGAATCCAG | 3060
| CTCCGGCTCT | GTAACACTTG | TTGCAACTGG | AGCAACTCTT | GCTGTAGGTA | ATATTTCAGG | 3120
| TAACACTGTT | ACTATTACTG | CGGATAGCGG | TAAATTAACC | TCCACAGTAG | GTTCTACAAT | 3180
| TAATGGGACT | AATAGTGTAA | CCACCTCAAG | CCAATCAGGC | GATATTGAAG | GTACAATTTC | 3240
| TGGTAATACA | GTAAATGTTA | CAGCAAGCAC | TGGTGATTTA | ACTATTGGAA | ATAGTGCAAA | 3300
| AGTTGAAGCG | AAAAATGGAG | CTGCAACCTT | AACTGCTGAA | TCAGGCAAAT | TAACCACCCA | 3360
| AACAGGCTCT | AGCATTACCT | CAAGCAATGG | TCAGACAACT | CTTACAGCCA | AGGATAGCAG | 3420
| TATCGCAGGA | AACATTAATG | CTGCTAATGT | GACGTTAAAT | ACCACAGGCA | CTTTAACTAC | 3480
| TACAGGGGAT | TCAAAGATTA | ACGCAACCAG | TGGTACCTTA | ACAATCAATG | CAAAAGATGC | 3540
| CAAATTAGAT | GGTGCTGCAT | CAGGTGACCG | CACAGTAGTA | AATGCAACTA | ACGCAAGTGG | 3600
| CTCTGGTAAC | GTGACTGCGA | AAACCTCAAG | CAGCGTGAAT | ATCACCGGGG | ATTTAAACAC | 3660
| AATAAATGGG | TTAAATATCA | TTTCGGAAAA | TGGTAGAAAC | ACTGTGCGCT | TAAGAGGCAA | 3720
| GGAAATTGAT | GTGAAATATA | TCCAACCAGG | TGTAGCAAGC | GTAGAAGAGG | TAATTGAAGC | 3780
| GAAACGCGTC | CTTGAGAAGG | TAAAAGATTT | ATCTGATGAA | GAAAGAGAAA | CACTAGCCAA | 3840
| ACTTGGTGTA | AGTGCTGTAC | GTTTCGTTGA | GCCAAATAAT | GCCATTACGG | TTAATACACA | 3900
| AAACGAGTTT | ACAACCAAAC | CATCAAGTCA | AGTGACAATT | TCTGAAGGTA | AGGCGTGTTT | 3960
| CTCAAGTGGT | AATGGCGCAC | GAGTATGTAC | CAATGTTGCT | GACGATGGAC | AGCAGTAGTC | 4020
| AGTAATTGAC | AAGGTAGATT | TCATCCTGCA | ATGAAGTCAT | TTTATTTTCG | TATTATTTAC | 4080
| TGTGTGGGTT | AAAGTTCAGT | ACGGGCTTTA | CCCACCTTGT | AAAAAATTAC | GAAAAATACA | 4140
| ATAAAGTATT | TTTAACAGGT | TATTATTATG | AAAAACATAA | AAAGCAGATT | AAAACTCAGT | 4200
| GCAATATCAA | TATTGCTTGG | CTTGGCTTCT | TCATCGACGT | ATGCAGAAGA | AGCGTTTTTA | 4260
| GTAAAAGGCT | TTCAGTTATC | TGGCGCG | | | | 4287

( 2 ) INFORMATION FOR SEQ ID NO:8:

( i ) SEQUENCE CHARACTERISTICS:
        ( A ) LENGTH: 4702 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

| | | | | | |
|---|---|---|---|---|---|
|GGGAATGAGC|GTCGTACACG|GTACAGCAAC|CATGCAAGTA|GACGGCAATA|AAACCACTAT|60|
|CCGTAATAGC|ATCAATGCTA|TCATCAATTG|GAAACAATTT|AACATTGACC|AAAATGAAAT|120|
|GGAGCAGTTT|TTACAAGAAA|GCAGCAACTC|TGCCGTTTTC|AACCGTGTTA|CATCTGACCA|180|
|AATCTCCCAA|TTAAAGGGA|TTTTAGATTC|TAACGGACAA|GTCTTTTAA|TCAACCCAAA|240|
|TGGTATCACA|ATAGGTAAAG|ACGCAATTAT|TAACACTAAT|GGCTTTACTG|CTTCTACGCT|300|
|AGACATTTCT|AACGAAAACA|TCAAGGCGCG|TAATTTCACC|CTTGAGCAAA|CCAAGGATAA|360|
|AGCACTCGCT|GAAATCGTGA|ATCACGGTTT|AATTACCGTT|GGTAAAGACG|GTAGCGTAAA|420|
|CCTTATTGGT|GGCAAAGTGA|AAAACGAGGG|CGTGATTAGC|GTAAATGGCG|GTAGTATTTC|480|
|TTTACTTGCA|GGGCAAAAAA|TCACCATCAG|CGATATAATA|AATCCAACCA|TCACTTACAG|540|
|CATTGCTGCA|CCTGAAAACG|AAGCGATCAA|TCTGGGCGAT|ATTTTGCCA|AGGTGGTAA|600|
|CATTAATGTC|CGCGCTGCCA|CTATTCGCAA|TAAAGGTAAA|CTTTCTGCCG|ACTCTGTAAG|660|
|CAAAGATAAA|AGTGGTAACA|TTGTTCTCTC|TGCCAAAGAA|GGTGAAGCGG|AAATTGGCGG|720|
|TGTAATTTCC|GCTCAAAATC|AGCAAGCCAA|AGGTGGTAAG|TTGATGATTA|CAGGTGATAA|780|
|AGTCACATTA|AAAACAGGTG|CAGTTATCGA|CCTTTCAGGT|AAAGAAGGGG|GAGAGACTTA|840|
|TCTTGGCGGT|GATGAGCGTG|GCGAAGGTAA|AAATGGTATT|CAATTAGCGA|AGAAAACCTC|900|
|TTTAGAAAAA|GGCTCGACAA|TTAATGTATC|AGGCAAAGAA|AAAGGCGGGC|GCGCTATTGT|960|
|ATGGGGCGAT|ATTGCATTAA|TTAATGGTAA|CATTAATGCT|CAAGGTAGCG|ATATTGCTAA|1020|
|AACTGGCGGC|TTTGTGGAAA|CATCAGGACA|TGACTTATCC|ATTGGTGATG|ATGTGATTGT|1080|
|TGACGCTAAA|GAGTGGTTAT|TAGACCCAGA|TGATGTGTCC|ATTGAAACTC|TTACATCTGG|1140|
|ACGCAATAAT|ACCGGCGAAA|ACCAAGGATA|TACAACAGGA|GATGGGACTA|AAGAGTCACC|1200|
|TAAAGGTAAT|AGTATTTCTA|AACCTACATT|AACAAACTCA|ACTCTTGAGC|AAATCCTAAG|1260|
|AAGAGGTTCT|TATGTTAATA|TCACTGCTAA|TAATAGAATT|TATGTTAATA|GCTCCATCAA|1320|
|CTTATCTAAT|GGCAGTTTAA|CACTTCACAC|TAAACGAGAT|GGAGTTAAAA|TTAACGGTGA|1380|
|TATTACCTCA|AACGAAAATG|GTAATTTAAC|CATTAAAGCA|GGCTCTTGGG|TTGATGTTCA|1440|
|TAAAAACATC|ACGCTTGGTA|CGGGTTTTTT|CAATATTGTC|GCTGGGGATT|CTGTAGCTTT|1500|
|TGAGAGAGAG|GGCGATAAAG|CACGTAACGC|AACAGATGCT|CAAATTACCG|CACAAGGGAC|1560|
|GATAACCGTC|AATAAGATG|ATAAACAATT|TAGATTCAAT|AATGTATCTA|TTAACGGGAC|1620|
|GGGCAAGGGT|TTAAAGTTTA|TTGCAAATCA|AAATAATTTC|ACTCATAAAT|TTGATGGCGA|1680|
|AATTAACATA|TCTGGAATAG|TAACAATTAA|CCAAACCACG|AAAAAGATG|TTAAATACTG|1740|
|GAATGCATCA|AAAGACTCTT|ACTGGAATGT|TTCTTCTCTT|ACTTGAATA|CGGTGCAAAA|1800|
|ATTTACCTTT|ATAAAATTCG|TTGATAGCGG|CTCAAATTCC|CAAGATTTGA|GGTCATCACG|1860|
|TAGAAGTTTT|GCAGGCGTAC|ATTTTAACGG|CATCGGAGGC|AAAACAAACT|TCAACATCGG|1920|
|AGCTAACGCA|AAAGCCTTAT|TTAAATTAAA|ACCAAACGCC|GCTACAGACC|CAAAAAAGA|1980|
|ATTACCTATT|ACTTTTAACG|CCAACATTAC|AGCTACCGGT|AACAGTGATA|GCTCTGTGAT|2040|
|GTTTGACATA|CACGCCAATC|TTACCTCTAG|AGCTGCCGGC|ATAAACATGG|ATTCAATTAA|2100|
|CATTACCGGC|GGGCTTGACT|TTTCCATAAC|ATCCCATAAT|CGCAATAGTA|ATGCTTTTGA|2160|
|AATCAAAAAA|GACTTAACTA|TAAATGCAAC|TGGCTCGAAT|TTTAGTCTTA|AGCAAACGAA|2220|
|AGATTCTTTT|TATAATGAAT|ACAGCAAACA|CGCCATTAAC|TCAAGTCATA|ATCTAACCAT|2280|
|TCTTGGCGGC|AATGTCACTC|TAGGTGGGGA|AAATTCAAGC|AGTAGCATTA|CGGGCAATAT|2340|
|CAATATCACC|AATAAAGCAA|ATGTTACATT|ACAAGCTGAC|ACCAGCAACA|GCAACACAGG|2400|

```
CTTGAAGAAA AGAACTCTAA CTCTTGGCAA TATATCTGTT GAGGGGAATT TAAGCCTAAC    2460

TGGTGCAAAT GCAAACATTG TCGGCAATCT TTCTATTGCA GAAGATTCCA CATTTAAAGG    2520

AGAAGCCAGT GACAACCTAA ACATCACCGG CACCTTTACC AACAACGGTA CCGCCAACAT    2580

TAATATAAAA CAAGGAGTGG TAAAACTCCA AGGCGATATT ATCAATAAAG GTGGTTTAAA    2640

TATCACTACT AACGCCTCAG GCACTCAAAA AACCATTATT AACGGAAATA TAACTAACGA    2700

AAAAGGCGAC TTAAACATCA AGAATATTAA AGCCGACGCC GAAATCCAAA TTGGCGGCAA    2760

TATCTCACAA AAAGAAGGCA ATCTCACAAT TTCTTCTGAT AAAGTAAATA TTACCAATCA    2820

GATAACAATC AAAGCAGGCG TTGAAGGGGG GCGTTCTGAT TCAAGTGAGG CAGAAAATGC    2880

TAACCTAACT ATTCAAACCA AAGAGTTAAA ATTGGCAGGA GACCTAAATA TTTCAGGCTT    2940

TAATAAAGCA GAAATTACAG CTAAAAATGG CAGTGATTTA ACTATTGGCA ATGCTAGCGG    3000

TGGTAATGCT GATGCTAAAA AAGTGACTTT TGACAAGGTT AAAGATTCAA AAATCTCGAC    3060

TGACGGTCAC AATGTAACAC TAAATAGCGA AGTGAAAACG TCTAATGGTA GTAGCAATGC    3120

TGGTAATGAT AACAGCACCG GTTTAACCAT TTCCGCAAAA GATGTAACGG TAAACAATAA    3180

CGTTACCTCC CACAAGACAA TAAATATCTC TGCCGCAGCA GGAAATGTAA CAACCAAAGA    3240

AGGCACAACT ATCAATGCAA CCACAGGCAG CGTGGAAGTA ACTGCTCAAA ATGGTACAAT    3300

TAAAGGCAAC ATTACCTCGC AAAATGTAAC AGTGACAGCA ACAGAAAATC TTGTTACCAC    3360

AGAGAATGCT GTCATTAATG CAACCAGCGG CACAGTAAAC ATTAGTACAA AAACAGGGGA    3420

TATTAAAGGT GGAATTGAAT CAACTTCCGG TAATGTAAAT ATTACAGCGA GCGGCAATAC    3480

ACTTAAGGTA AGTAATATCA CTGGTCAAGA TGTAACAGTA ACAGCGGATG CAGGAGCCTT    3540

GACAACTACA GCAGGCTCAA CCATTAGTGC GACAACAGGC AATGCAAATA TTACAACCAA    3600

AACAGGTGAT ATCAACGGTA AAGTTGAATC CAGCTCCGGC TCTGTAACAC TTGTTGCAAC    3660

TGGAGCAACT CTTGCTGTAG GTAATATTTC AGGTAACACT GTTACTATTA CTGCGGATAG    3720

CGGTAAATTA ACCTCCACAG TAGGTTCTAC AATTAATGGG ACTAATAGTG TAACCACCTC    3780

AAGCCAATCA GGCGATATTG AAGGTACAAT TTCTGGTAAT ACAGTAAATG TTACAGCAAG    3840

CACTGGTGAT TTAACTATTG GAAATAGTGC AAAAGTTGAA GCGAAAAATG GAGCTGCAAC    3900

CTTAACTGCT GAATCAGGCA AATTAACCAC CCAAACAGGC TCTAGCATTA CCTCAAGCAA    3960

TGGTCAGACA ACTCTTACAG CCAAGGATAG CAGTATCGCA GGAAACATTA ATGCTGCTAA    4020

TGTGACGTTA AATACCACAG GCACTTTAAC TACTACAGGG GATTCAAAGA TTAACGCAAC    4080

CAGTGGTACC TTAACAATCA ATGCAAAAGA TGCCAAATTA GATGGTGCTG CATCAGGTGA    4140

CCGCACAGTA GTAAATGCAA CTAACGCAAG TGGCTCTGGT AACGTGACTG CGAAAACCTC    4200

AAGCAGCGTG AATATCACCG GGATTTAAA CACAATAAAT GGGTTAAATA TCATTTCGGA    4260

AAATGGTAGA AACACTGTGC GCTTAAGAGG CAAGGAAATT GATGTGAAAT ATATCCAACC    4320

AGGTGTAGCA AGCGTAGAAG AGGTAATTGA AGCGAAACGC GTCCTTGAGA AGGTAAAAGA    4380

TTTATCTGAT GAAGAAAGAG AAACACTAGC CAAACTTGGT GTAAGTGCTG TACGTTTCGT    4440

TGAGCCAAAT AATGCCATTA CGGTTAATAC ACAAAACGAG TTTACAACCA AACCATCAAG    4500

TCAAGTGACA ATTTCTGAAG GTAAGGCGTG TTTCTCAAGT GGTAATGGCG CACGAGTATG    4560

TACCAATGTT GCTGACGATG GACAGCAGTA GTCAGTAATT GACAAGGTAG ATTTCATCCT    4620

GCAATGAAGT CATTTTATTT TCGTATTATT TACTGTGTGG GTTAAAGTTC AGTACGGGCT    4680

TTACCCACCT TGTAAAAAAT TA                                            4702
```

HIGH MOLECULAR WEIGHT SURFACE PROTEINS OF NON-TYPEABLE HAEMOPHILUS

This application is a 35 USC 371 of PCT/US94/02550 filed Mar. 15, 1994.

FIELD OF INVENTION

This invention relates to high molecular weight proteins of non-typeable haemophilus.

BACKGROUND TO THE INVENTION

Non-typeable *Haemophilus influenzae* are non-encapsulated organisms that are defined by their lack of reactivity with antisera against known *H. influenzae* capsular antigens.

These organisms commonly inhabit the upper respiratory tract of humans and are frequently responsible for infections, such as otitis media, sinusitis, conjunctivitis, bronchitis and pneumonia. Since these organisms do not have a polysaccharide capsule, they are not controlled by the present *Haemophilus influenzae* type b (Hib) vaccines, which are directed towards Hib bacterial capsular polysaccharides. The non-typeable strains, however, do produce surface antigens that can elicit bactericidal antibodies. Two of the major outer membrane proteins, P2 and P6, have been identified as targets of human serum bactericidal activity. However, it has been shown that the P2 protein sequence is variable, in particular in the non-typeable Haemophilus strains. Thus, a P2-based vaccine would not protect against all strains of the organism.

There have previously been identified by Barenkamp et al (*Pediatr. Infect. Dis. J.,* 9:333–339, 1990) a group of high-molecular-weight (HMW) proteins that appeared to be major targets of antibodies present in human convalescent sera. Examination of a series of middle ear isolates revealed the presence of one or two such proteins in most strains. However, prior to the present invention, the structures of these proteins were unknown as were pure isolates of such proteins.

SUMMARY OF INVENTION

The inventors, in an effort to further characterize the high molecular weight (HMW) Haemophilus proteins, have cloned, expressed and sequenced the genes coding for two immunodominant HMW proteins (designated HMW1 and HMW2) from a prototype non-typeable Haemophilus strain and have cloned, expressed and almost completely sequenced the genes coding for two additional immunodominant HMW proteins (designated HMW3 and HMW4) from another non-typeable Haemophilus strain.

In accordance with one aspect of the present invention, therefore, there is provided an isolated and purified gene coding for a high molecular weight protein of a non-typeable Haemophilus strain, particularly a gene coding for protein HMW1, HMW2, HMW3 or HMW4, as well as any variant or fragment of such protein which retains the immunological ability to protect against disease caused by a non-typeable Haemophilus strain. In another aspect, the invention provides a high molecular weight protein of non-typeable *Haemophilus influenzae* which is encoded by these genes.

BRIEF DESCRIPTION OF DRAWINGS

FIGS. 1A–1G is a DNA sequence of a gene coding for protein HMW1 (SEQ ID NO: 1);

FIGS. 2A–2B is a derived amino acid sequence of protein HMW1 (SEQ ID NO: 2);

FIGS. 3A–3G is a DNA sequence of a gene coding for protein HMW2 (SEQ ID NO: 3);

FIGS. 4A–4B is a derived amino acid sequence of HMW2 (SEQ ID NO: 4);

FIG. 5B shows the restriction map of the T7 expression vector pT7-7;

FIGS. 6A–6L contains the DNA sequence of a gene cluster for the hmw1 gene (SEQ ID NO: 5), comprising nucleotides 351 to 4958 (ORF a) (as in FIG. 1), as well as two additional downstream genes in the 3' flanking region, comprising ORFs b, nucleotides 5114–6748 and c nucleotides 7062–9011;

FIGS. 7A–7L contains the DNA sequence of a gene cluster for the hmw2 gene (SEQ ID NO: 6), comprising nucleotides 792 to 5222 (ORF a) (as in FIG. 3), as well as two additional downstream genes in the 3' flanking region, comprising ORFs b, nucleotides 5375–7009, and c, nucleotides 7249–9198;

FIGS. 8A–8F is a partial DNA sequence of a gene coding for protein HMW3 (SEQ ID NO: 7);

FIGS. 9A–9F is a partial DNA sequence of a gene coding for protein HMW4 (SEQ ID NO: 8); and FIGS. 10A–10L is a comparison table for the derived amino acid sequence for proteins HMW1, HMW2, HMW3 and HMW4.

GENERAL DESCRIPTION OF INVENTION

Figure 5A:
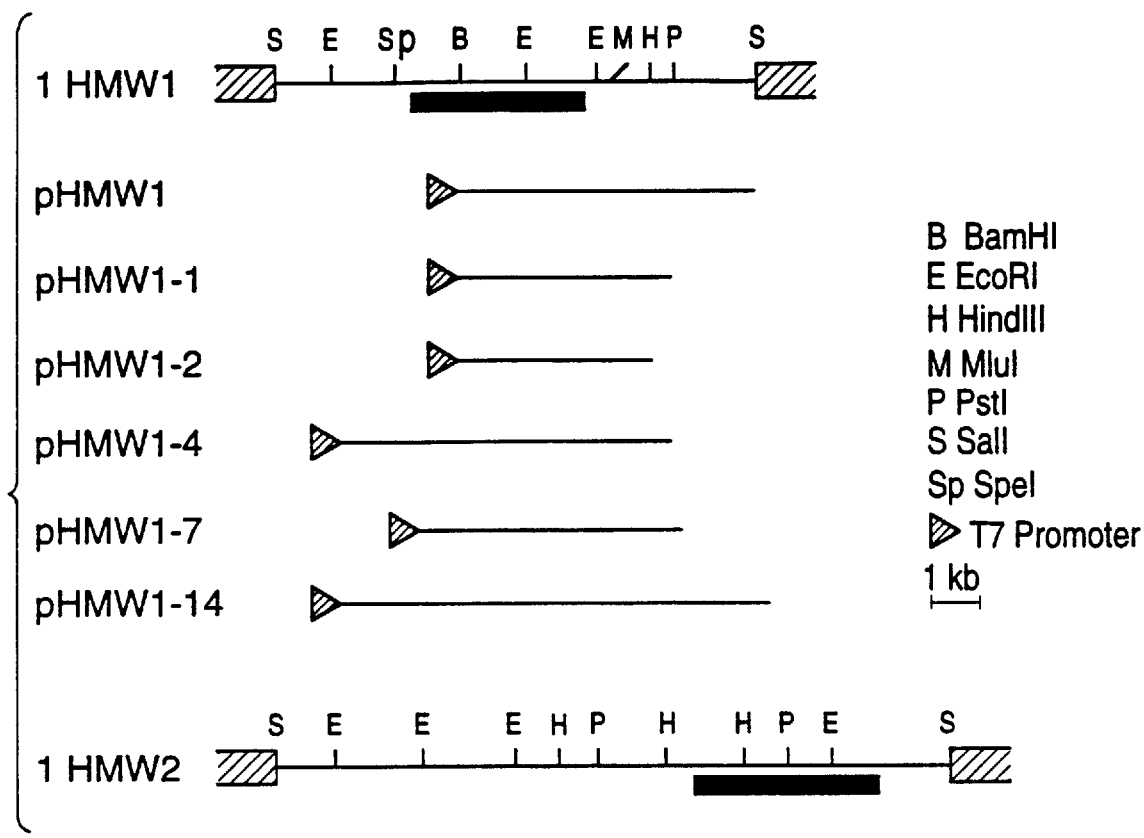
FIG. 5A shows restriction maps of representative recombinant phages which contained the HMW1 or HMW2 structural genes, the locations of the structural genes being indicated by the shaded bars.

The DNA sequences of the genes coding for HMW1 and HMW2, shown in FIGS. 1 and 3 respectively, were shown to be about 80% identical, with the first 1259 base pairs of the genes being identical. The derived amino acid sequences of the two HMW proteins, shown in FIGS. 2 and 4 respectively, are about 70% identical. Furthermore, the encoded proteins are antigenically related to the filamentous hemagglutinin surface protein of *Bordetella pertussis*. A monoclonal antibody prepared against filamentous hemagglutinin (FHA) of *Bordetella pertussis* was found to recognize both of the high molecular weight proteins. This data suggests that the HMW and FHA proteins may serve similar biological functions. The derived amino acid sequences of the HMW1 and HMW2 proteins show sequence similarity to that for the FHA protein. It has further been shown that these antigenically-related proteins are produced by the majority of the non-typeable strains of Haemophilus. Antisera raised against the protein expressed by the HMW1 gene recognizes both the HMW2 protein and the *B. pertussis* FHA. The present invention includes an isolated and purified high molecular weight protein of non-typeable haemophilus which is antigenically related to the *B. pertussis* FHA, which may be obtained from natural sources or produced recombinantly.

A phage genomic library of a known strain of non-typeable Haemophilus was prepared by standard methods and the library was screened for clones expressing high molecular weight proteins, using a high titre antiserum against HMW's. A number of strongly reactive DNA clones were plaque-purified and sub-cloned into a T7 expression plasmid. It was found that they all expressed either one or the other of the two high-molecular-weight proteins designated HMW1 and HMW2, with apparent molecular weights of 125 and 120 kDa, respectively, encoded by open reading frames of 4.6 kb and 4.4 kb, respectively.

Representative clones expressing either HMW1 or HMW2 were further characterized and the genes isolated, purified and sequenced. The DNA sequence of HMW1 is shown in FIG. 1 and the corresponding derived amino acid sequence in FIG. 2. Similarly, the DNA sequence of HMW2 is shown in FIG. 3 and the corresponding derived amino acid sequence in FIG. 4. Partial purification of the isolated proteins and N-terminal sequence analysis indicated that the expressed proteins are truncated since their sequence starts at residue number 442 of both full length HMW1 and HMW2 gene products.

Subcloning studies with respect to the hmw1 and hmw2 genes indicated that correct processing of the HMW proteins required the products of additional downstream genes. It has been found that both the hmw1 and hmw2 genes are flanked by two additional downstream open reading frames (ORFs), designated b and c, respectively, (see FIGS. 6 and 7).

The b ORFs are 1635 bp in length, extending from nucleotides 5114 to 6748 in the case of hmw1 and nucleotides 5375 to 7009 in the case of hmw2, with their derived amino acid sequences 99% identical. The derived amino acid sequences demonstrate similarity with the derived amino acid sequences of two genes which encode proteins required for secretion and activation of hemolysins of *P. mirabilis* and *S. marcescens*.

The c ORFs are 1950 bp in length, extending from nucleotides 7062 to 9011 in the case of hmw1 and nucleotides 7249 to 9198 in the case of hmw2, with their derived amino acid sequences 96% identical. The hmw1 c ORF is preceded by a series of 9 bp direct tandem repeats. In plasmid subclones, interruption of the hmw1 b or c ORF results in defective processing and secretion of the hmw1 structural gene product.

The two high molecular weight proteins have been isolated and purified and shown to be partially protective against otitis media in chinchillas and to function as adhesins. These results indicate the potential for use of such high molecular proteins and structurally-related proteins of other non-typeable strains of *Haemophilus influenzae* as components in non-typeable *Haemophilus influenzae* vaccines.

Since the proteins provided herein are good cross-reactive antigens and are present in the majority of non-typeable Haemophilus strains, it is evident that these HMW proteins may become integral constituents of a universal Haemophilus vaccine. Indeed, these proteins may be used not only as protective antigens against otitis, sinusitis and bronchitis caused by the non-typeable Haemophilus strains, but also may be used as carriers for the protective Hib polysaccharides in a conjugate vaccine against meningitis. The proteins also may be used as carriers for other antigens, haptens and polysaccharides from other organisms, so as to induce immunity to such antigens, haptens and polysaccharides.

The nucleotide sequences encoding two high molecular weight proteins of a different non-typeable Haemophilus strain (designated HMW3 and HMW4) have been largely elucidated, and are presented in FIGS. 8 and 9. HMW3 has an apparent molecular weight of 125 kDa while HMW4 has an apparent molecular weight of 123 kDa. These high molecular weight proteins are antigenically related to the HMW1 and HMW2 proteins and to FHA. Sequence analysis of HMW3 is approximately 85% complete and of HMW4 95% complete, with short stretches at the 5'-ends of each gene remaining to be sequenced.

FIG. 10 contains a multiple sequence comparison of the derived amino acid sequences for the four high molecular weight proteins identified herein. As may be seen from this comparison, stretches of identical peptide sequence may be found throughout the length of the comparison, with HMW3 more closely resembling HMW1 and HMW4 more closely resembling HMW2. This information is highly suggestive of a considerable sequence homology between high molecular weight proteins from various non-typeable Haemophilus strains.

In addition, mutants of non-typeable *H. influenzae* strains that are deficient in expression of HMW1 or HMW2 or both have been constructed and examined for their capacity to adhere to cultured human epithelial cells. The hmw1 and hmw2 gene clusters have been expressed in *E. coli* and have been examined for in vitro adherence. The results of such experimentation demonstrate that both HMW1 and HMW2 mediate attachment and hence are adhesins and that this function is present even in the absence of other *H. influenzae* surface structures.

With the isolation and purification of the high molecular weight proteins, the inventors are able to determine the major protective epitopes by conventional epitope mapping and synthesize peptides corresponding to these determinants to be incorporated in fully synthetic or recombinant vaccines. Accordingly, the invention also comprises a synthetic peptide having an amino acid sequence corresponding to at least one protective epitope of a high molecular weight protein of a non-typeable *Haemophilus influenzae*. Such peptides are of varying length that constitute portions of the high-molecular-weight proteins, that can be used to induce immunity, either directly or as part of a conjugate, against the relative organisms and thus constitute vaccines for protection against the corresponding diseases.

The present invention also provides any variant or fragment of the proteins that retains the potential immunological ability to protect against disease caused by non-typeable Haemophilus strains. The variants may be constructed by partial deletions or mutations of the genes and expression of the resulting modified genes to give the protein variations.

EXAMPLES

Example 1

Non-typeable *H. influenzae* strains 5 and 12 were isolated in pure culture from the middle ear fluid of children with acute otitis media. Chromosomal DNA from strain 12, providing genes encoding proteins HMW1 and HMW2, was prepared by preparing Sau3A partial restriction digests of chromosomal DNA and fractionating on sucrose gradients. Fractions containing DNA fragments in the 9 to 20 kbp range were pooled and a library was prepared by ligation into λEMBL3 arms. Ligation mixtures were packaged in vitro and plate-amplified in a P2 lysogen of *E. coli* LE392.

For plasmid subcloning studies, DNA from a representative recombinant phage was subcloned into the T7 expression plasmid pT7-7, containing the T7 RNA polymerase promoter Φ10, a ribosome-binding site and the translational start site for the T7 gene 10 protein upstream from a multiple cloning site (see FIG. 5B).

DNA sequence analysis was performed by the dideoxy method and both strands of the HMW1 gene and a single strand of the HMW2 gene were sequenced.

Western immunoblot analysis was performed to identify the recombinant proteins being produced by reactive phage clones. Phage lysates grown in LE392 cells or plaques picked directly from a lawn of LE392 cells on YT plates were solubilized in gel electrophoresis sample buffer prior to electrophoresis. Sodium dodecyl sulfate (SDS)-polyacrylamide gel electrophoresis was performed on 7.5% or 11% polyacrylamide modified Laemmli gels. After transfer of the proteins to nitrocellulose sheets, the sheets were probed sequentially with an E. coli-absorbed human serum sample containing high-titer antibody to the high-molecular-weight proteins and then with alkaline phosphatase-conjugated goat anti-human immunoglobulin G (IgG) second antibody. Sera from healthy adults contains high-titer antibody directed against surface-exposed high-molecular-weight proteins of non-typeable H. influenzae. One such serum sample was used as the screening antiserum after having been extensively absorbed with LE392 cells.

To identify recombinant proteins being produced by E. coli transformed with recombinant plasmids, the plasmids of interest were used to transform E. coli BL21 (DE3)/pLysS. The transformed strains were grown to an $A_{600}$ of 0.5 in L broth containing 50 μg of ampicillin per ml. IPTG was then added to 1 mM. One hour later, cells were harvested, and a sonicate of the cells was prepared. The protein concentrations of the samples were determined by the bicinchoninic acid method. Cell sonicates containing 100 μg of total protein were solubilized in electrophoresis sample buffer, subjected to SDS-polyacrylamide gel electrophoresis, and transferred to nitrocellulose. The nitrocellulose was then probed sequentially with the E. coli-absorbed adult serum sample and then with alkaline phosphatase-conjugated goat anti-human IgG second antibody.

Western immunoblot analysis also was performed to determine whether homologous and heterologous non-typeable H. influenzae strains expressed high-molecular-weight proteins antigenically related to the protein encoded by the cloned HMW1 gene (rHMW1). Cell sonicates of bacterial cells were solubilized in electrophoresis sample buffer, subjected to SDS-polyacrylamide gel electrophoresis, and transferred to nitrocellulose. Nitrocellulose was probed sequentially with polyclonal rabbit rHMW1 antiserum and then with alkaline phosphatase-conjugated goat anti-rabbit IgG second antibody.

Finally, Western immunoblot analysis was performed to determine whether non-typeable Haemophilus strains expressed proteins antigenically related to the filamentous hemagglutinin protein of Bordetella pertussis. Monoclonal antibody X3C, a murine immunoglobulin G (IgG) antibody which recognizes filamentous hemagglutinin, was used to probe cell sonicates by Western blot. An alkaline phosphatase-conjugated goat anti-mouse IgG second antibody was used for detection.

To generate recombinant protein antiserum, E. coli BL21 (DE3)/pLysS was transformed with pHMW1-4, and expression of recombinant protein was induced with IPTG, as described above. A cell sonicate of the bacterial cells was prepared and separated into a supernatant and pellet fraction by centrifugation at 10,000×g for 30 min. The recombinant protein fractionated with the pellet fraction. A rabbit was subcutaneously immunized on biweekly schedule with 1 mg of protein from the pellet fraction, the first dose given with Freund's complete adjuvant and subsequent doses with Freund's incomplete adjuvant. Following the fourth injection, the rabbit was bled. Prior to use in the Western blot assay, the antiserum was absorbed extensively with sonicates of the host E. coli strain transformed with cloning vector alone.

To assess the sharing of antigenic determinants between HMW1 and filamentous hemagglutinin, enzyme-linked immunosorbent assay (ELISA) plates (Costar, Cambridge, Mass.) were coated with 60 μl of a 4-ug/ml solution of filamentous hemagglutinin in Dulbecco's phosphate-buffered saline per well for 2 h at room temperature. Wells were blocked for 1 h with 1% bovine serum albumin in Dulbecco's phosphate-buffered saline prior to addition of serum dilutions. rHMW1 antiserum was serially diluted in 0.1% Brij (Sigma, St. Louis, Mo.) in Dulbecco's phosphate-buffered saline and incubated for 3 h at room temperature. After being washed, the plates were incubated with peroxidase-conjugated goat anti-rabbit lgG antibody (Bio-Rad) for 2 h at room temperature and subsequently developed with 2,2'-azino-bis(3-ethylbenzthiazoline-6-sulfonic acid) (Sigma) at a concentration of 0.54 in mg/ml in 0.1M sodium citrate buffer, pH 4.2, containing 0.03% $H_2O_2$. Absorbances were read on an automated ELISA reader.

Recombinant phage expressing HMW1 or HMW 2 were recovered as follows. The non-typeable H. influenzae strain 12 genomic library was screened for clones expressing high-molecular-weight proteins with an E. coli-absorbed human serum sample containing a high titer of antibodies directed against the high-molecular-weight proteins.

Numerous strongly reactive clones were identified along with more weakly reactive ones. Twenty strongly reactive clones were plaque-purified and examined by Western blot for expression of recombinant proteins. Each of the strongly reactive clones expressed one of two types of high-molecular-weight proteins, designated HMW1 and HMW2. The major immunoreactive protein bands in the HMW1 and HMW2 lysates migrated with apparent molecular masses of 125 and 120 kDa, respectively. In addition to the major bands, each lysate contained minor protein bands of higher apparent molecular weight. Protein bands seen in the HMW2 lysates at molecular masses of less than 120 kDa were not regularly observed and presumably represent proteolytic degradation products. Lysates of LE392 infected with the λEMBL3 cloning vector alone were non-reactive when immunologically screened with the same serum sample. Thus, the observed activity was not due to cross-reactive E. coli proteins or λEMBL3-encoded proteins. Furthermore, the recombinant proteins were not simply binding immunoglobulin nonspecifically, since the proteins were not reactive with the goat anti-human IgG conjugate alone, with normal rabbit sera, or with serum from a number of healthy young infants.

Representative clones expressing either the HMW1 or HMW2 recombinant proteins were characterized further. The restriction maps of the two phage types were different from each other, including the regions encoding the HMW1 and HMW2 structural genes. FIG. 5A shows restriction maps of representative recombinant phage which contained the HMW1 or HMW2 structural genes. The locations of the structural genes are indicated by the shaded bars.

HMW1 plasmid subclones were constructed by using the T7 expression plasmid T7-7 (FIGS. 5A and B). HMW2 plasmid subclones also were constructed, and the results with these latter subclones were similar to those observed with the HMW1 constructs.

The approximate location and direction of transcription of the HMW1 structure gene were initially determined by using plasmid pHMW1 (FIG. 5A). This plasmid was constructed by inserting the 8.5-kb BamHI-SalI fragment from λHMW1 into BamHI- and SalI-cut pT7-7. E. coli transformed with pHMW1 expressed an immunoreactive recombinant protein with an apparent molecular mass of 115 kDa, which was strongly inducible with IPTG. This protein was significantly smaller than the 125-kDa major protein expressed by the parent phage, indicating that it either was being expressed as a fusion protein or was truncated at the carboxy terminus.

To more precisely localize the 3' end of the structural gene, additional plasmids were constructed with progressive deletions from the 3' end of the pHMW1 construct. Plasmid pHMW1-1 was constructed by digestion of pHMW1 with PstI, isolation of the resulting 8.8-kb fragment, and religation. Plasmid pHMW1-2 was constructed by digestion of pHMW1 with HindIII, isolation of the resulting 7.5-kb fragment, and religation. E. coli transformed with either plasmid pHMW1-1 or pHMW1-2 also expressed an immunoreactive recombinant protein with an apparent molecular mass of 115 kDa. These results indicated that the 3' end of the structural gene was 5' of the HindIII site.

To more precisely localize the 5' end of the gene, plasmids pHMW1-4 and pHMW1-7 were constructed. Plasmid pHMW1-4 was constructed by cloning the 5.1-kb BamHI-HindIII fragment from λHMW1 into a pT7-7-derived plasmid containing the upstream 3.8-kb EcoRI-BamHi fragment. E. coli transformed with pHMW1-4 expressed an immunoreactive protein with an apparent molecular mass of approximately 160 kDa. Although protein production was inducible with IPTG, the levels of protein production in these transformants were substantially lower than those with the pHMW1-2 transformants described above. Plasmid pHMW1-7 was constructed by digesting pHMW1-4 with NdeI and SpeI. The 9.0-kbp fragment generated by this double digestion was isolated, blunt ended, and religated. E. coli transformed with pHMW1-7 also expressed an immunoreactive protein with an apparent molecular mass of 160 kDa, a protein identical in size to that expressed by the pHMW1-4 transformants. The result indicated that the initiation codon for the HMW1 structural gene was 3' of the SpeI site. DNA sequence analysis confirmed this conclusion.

As noted above, the λHMW1 phage clones expressed a major immunoreactive band of 125 kDa, whereas the HMW1 plasmid clones pHMW1-4 and pHMW1-7, which contained what was believed to be the full-length gene, expressed an immunoreactive protein of approximately 160 kDa. This size discrepancy was disconcerting. One possible explanation was that an additional gene or genes necessary for correct processing of the HMW1 gene product were deleted in the process of subcloning. To address this possibility, plasmid pHMW1-14 was constructed. This construct was generated by digesting pHMW1 with NdeI and MluI and inserting the 7.6-kbp NdeI-MluI fragment isolated from pHMW1-4. Such a construct would contain the full-length HMW1 gene as well as the DNA 3' of the HMW1 gene which was present in the original HMW1 phage. E. coli transformed with this plasmid expressed major immunoreactive proteins with apparent molecular masses of 125 and 160 kDa as well as additional degradation products. The 125- and 160-kDa bands were identical to the major and minor immunoreactive bands detected in the HMW1 phage lysates. Interestingly, the pHMW1-14 construct also expressed significant amounts of protein in the uninduced condition, a situation not observed with the earlier constructs.

The relationship between the 125- and 160-kDa proteins remains somewhat unclear. Sequence analysis, described below, reveals that the HMW1 gene would be predicted to encode a protein of 159 kDa. It is believed that the 160-kDa protein is a precursor form of the mature 125-kDa protein, with the conversion from one protein to the other being dependent on the products of the two downstream genes.

Sequence analysis of the HMW1 gene (FIG. 1) revealed a 4,608-bp open reading frame (ORF), beginning with an ATG codon at nucleotide 351 and ending with a TAG stop codon at nucleotide 4959. A putative ribosome-binding site with the sequence AGGAG begins 10 bp upstream of the putative initiation codon. Five other inframe ATG codons are located within 250 bp of the beginning of the ORF, but none of these is preceded by a typical ribosome-binding site. The 5'-flanking region of the ORF contains a series of direct tandem repeats, with the 7-bp sequence ATCTTTC repeated 16 times. These tandem repeats stop 100 bp 5' of the putative initiation codon. An 8-bp inverted repeat characteristic of a rho-independent transcriptional terminator is present, beginning at nucleotide 4983, 25 bp 3' of the presumed translational stop. Multiple termination codons are present in all three reading frames both upstream and downstream of the ORF. The derived amino acid sequence of the protein encoded by the HMW1 gene (FIG. 2) has a molecular weight of 159,000, in good agreement with the apparent molecular weights of the proteins expressed by the HMW1-4 and HMW1-7 transformants. The derived amino acid sequence of the amino terminus does not demonstrate the characteristics of a typical signal sequence. The BamHI site used in generation of pHMW1 comprises bp 1743 through 1748 of the nucleotide sequence. The ORF downstream of the BamHI site would be predicted to encode a protein of 111 kDa, in good agreement with the 115 kDa estimated for the apparent molecular mass of the pHMW1-encoded fusion protein.

The sequence of the HMW2 gene (FIG. 3) consists of a 4,431-bp ORF, beginning with an ATG codon at nucleotide 352 and ending with a TAG stop codon at nucleotide 4783. The first 1,259 bp of the ORF of the HMW2 gene are identical to those of the HMW1 gene. Thereafter, the sequences begin to diverge but are 80% identical overall. With the exception of a single base addition at nucleotide 93 of the HMW2 sequence, the 5'-flanking regions of the HMW1 and HMW2 genes are identical for 310 bp upstream from the respective initiation codons. Thus, the HMW2 gene is preceded by the same set of tandem repeats and the same putative ribosome-binding site which lies 5' of the HMW1 gene. A putative transcriptional terminator identical to that identified 3' of the HMW1 ORF is noted, beginning at nucleotide 4804. The discrepancy in the lengths of the two genes is principally accounted for by a 186-bp gap in the HMW2 sequence, beginning at nucleotide position 3839. The derived amino acid sequence of the protein encoded by the HMW2 gene (FIG. 4) has a molecular weight of 155,000 and is 71% identical with the derived amino acid sequence of the HMW1 gene.

The derived amino acid sequences of both the HMW1 and HMW2 genes (FIGS. 2 and 4) demonstrated sequence similarity with the derived amino acid sequence of filamentous hemagglutinin of Bordetella pertussis, a surface-associated protein of this organism. The initial and optimized TFASTA scores for the HMW1-filamentous hemagglutinin sequence comparison were 87 and 186, respectively, with a word size of 2. The z score for the comparison was 45.8. The initial and optimized TFASTA scores for the HMW2-filamentous hemagglutinin sequence comparison were 68 and 196, respectively. The z score for the latter comparison was 48.7. The magnitudes of the initial and optimized TFASTA scores and the z scores suggested that a biologically significant relationship existed between the HMW1 and HMW2 gene products and filamentous hemagglutinin. When the derived amino acid sequences of HMW1, HMW2, and filamentous hemagglutinin genes were aligned and compared, the similarities were most notable at the amino-terminal ends of the three sequences. Twelve of the first 22 amino acids in the predicted peptide sequences were identical. In additional, the sequences demonstrated a common five-amino-acid stretch, Asn-Pro-Asn-Gly-Ile, and several shorter stretches of sequence identity within the first 200 amino acids.

Example 2

To further explore the HMW1-filamentous hemagglutinin relationship, the ability of antiserum prepared against the HMW1-4 recombinant protein (rHMW1) to recognize purified filamentous hemagglutinin was assessed. The rHMW1 antiserum demonstrated ELISA reactivity with filamentous hemagglutinin in a dose-dependent manner. Preimmune rabbit serum had minimal reactivity in this assay. The rHMW1 antiserum also was examined in a Western blot assay and demonstrated weak but positive reactivity with purified filamentous hemagglutinin in this system also.

To identify the native Haemophilus protein corresponding to the HMW1 gene product and to determine the extent to which proteins antigenically related to the HMW1 cloned gene product were common among other non-typeable *H. influenzae* strains, a panel of Haemophilus strains was screened by Western blot with the rHMW1 antiserum. The antiserum recognized both a 125- and a 120-kDa protein band in the homologous strain 12, the putative mature protein products of the HMW1 and HMW2 genes, respectively.

When used to screen heterologous non-typeable *H. influenzae* strains, rHMW1 antiserum recognized high-molecular-weight proteins in 75% of 125 epidemiologically unrelated strains. In general, the antiserum reacted with one or two protein bands in the 100- to 150-kDa range in each of the heterologous strains in a pattern similar but not identical to that seen in the homologous strain.

Monoclonal antibody X3C is a murine IgG antibody directed against the filamentous hemagglutinin protein of *B. pertussis*. This antibody can inhibit the binding of *B. pertussis* cells to Chinese hamster ovary cells and HeLa cells in culture and will inhibit hemagglutination of erythrocytes by purified filamentous hemagglutinin. A Western blot assay was performed in which this monoclonal antibody was screened against the same panel of non-typeable *H. influenzae* strains discussed above. Monoclonal antibody X3C recognized both the high-molecular-weight proteins in non-typeable *H. influenzae* strain 12 which were recognized by the recombinant-protein antiserum. In addition, the monoclonal antibody recognized protein bands in a subset of heterologous non-typeable *H. influenzae* strains which were identical to those recognized by the recombinant-protein antiserum. On occasion, the filamentous hemagglutinin monoclonal antibody appeared to recognize only one of the two bands which had been recognized by the recombinant-protein antiserum. Overall, monoclonal antibody X3C recognized high-molecular-weight protein bands identical to those recognized by the rHMW1 antiserum in approximately 35% of our collection of non-typeable *H. influenzae* strains.

Example 3

Mutants deficient in expression of HMW1, MW2 or both proteins were constructed to examine the role of these proteins in bacterial adherence. The following strategy was employed. pHMW1-14 (see Example 1, FIG. 5A) was digested with BamHI and then ligated to a kanamycin cassette isolated on a 1.3-kb BamHI fragment from pUC4K. The resultant plasmid (pHMW1-17) was linearized by digestion with XbaI and transformed into non-typeable *H. influenzae* strain 12, followed by selection for kanamycin resistant colonies. Southern analysis of a series of these colonies demonstrated two populations of transformants, one with an insertion in the HMW1 structural gene and the other with an insertion in the HMW2 structural gene. One mutant from each of these classes was selected for further studies.

Mutants deficient in expression of both proteins were recovered using the following protocol. After deletion of the 2.1-kb fragment of DNA between two EcoRI sites spanning the 3'-portion of the HMW1 structural gene in pHMW-15, the kanamycin cassette from pUC4K was inserted as a 1.3-kb EcoRI fragment. The resulting plasmid (pHMW1-16) was linearized by digestion with XbaI and transformed into strain 12, followed again by selection for kanamycin resistant colonies. Southern analysis of a representative sampling of these colonies demonstrated that in seven of eight cases, insertion into both the HMW1 and HMW2 loci had occurred. One such mutant was selected for further studies.

To confirm the intended phenotypes, the mutant strains were examined by Western blot analysis with a polyclonal antiserum against recombinant HMW1 protein. The parental strain expressed both the 125-kD HMW1 and the 120-kD HMW2 protein. In contrast, the HMW2 mutant failed to express the 120-kD protein, and the HMW1 mutant failed to express the 125-kD protein. The double mutant lacked expression of either protein. On the basis of whole cell lysates, outer membrane profiles, and colony morphology, the wild type strain and the mutants were otherwise identical with one another. Transmission electron microscopy demonstrated that none of the four strains expressed pili.

The capacity of wild type strain 12 to adhere to Chang epithelial cells was examined. In such assays, bacteria were inoculated into broth and allowed to grow to a density of $\sim 2 \times 10^9$ cfu/ml. Approximately $2 \times 10^7$ cfu were inoculated onto epithelial cell monolayers, and plates were gently centrifuged at 165×g for 5 minutes to facilitate contact between bacteria and the epithelial surface. After incubation for 30 minutes at 37° C. in 5% $CO_2$, monolayers were rinsed 5 times with PBS to remove nonadherent organisms and were treated with trypsin-EDTA (0.05% trypsin, 0.5% EDTA) in PBS to release them from the plastic support. Well contents were agitated, and dilutions were plated on solid medium to yield the number of adherent bacteria per monolayer. Percent adherence was calculated by dividing the number of adherent cfu per monolayer by the number of inoculated cfu.

As depicted in Table 1 below (the Tables appear at the end of the descriptive text), this strain adhered quite efficiently, with nearly 90% of the inoculum binding to the monolayer. Adherence by the mutant expressing HMW1 but not HMW2 (HMW2$^-$) was also quite efficient and comparable to that by the wild type strain. In contrast, attachment by the strain expressing HMW2 but deficient in expression of HMW1 (HMW1$^-$) was decreased about 15-fold relative to the wild type. Adherence by the double mutant (HMW1$^-$/HMW2$^-$) was decreased even further, approximately 50-fold compared with the wild type and approximately 3-fold compared with the HMW1 mutant. Considered together, these results suggest that both the HMW1 protein and the, HMW2 protein influence attachment to Chang epithelial cells. Interestingly, optimal adherence to this cell line appears to require HMW1 but not HMW2.

Example 4

Using the plasmids pHMW1-16 and pHMW1-17 (see Example 3) and following a scheme similar to that employed with strain 12 as described in Example 3, three non-typeable Haemophilus strain 5 mutants were isolated, including one with the kanamycin gene inserted into the hmw1-like (designated hmw3) locus, a second with an insertion in the hmw2-like (designated hmw4) locus, and a third with insertions in both loci. As predicted, Western immunoblot analysis demonstrated that the mutant with insertion of the kanamycin cassette into the hmw1-like locus had lost expression of the HMW3 125-kD protein, while the mutant with insertion into the hmw2-like locus failed to express the HMW4 123-kD protein. The mutant with a double insertion was unable to express either of the high molecular weight proteins.

As shown in Table 1 below, wild type strain 5 demonstrated high level adherence, with almost 80% of the inoculum adhering per monolayer. Adherence by the mutant deficient in expression of the HMW2-like protein was also quite high. In contrast, adherence by the mutant unable to express the HMW1-like protein was reduced about 5-fold relative to the wild type, and attachment by the double mutant was diminished even further (approximately 25-fold). Examination of Giemsa-stained samples confirmed these observations (not shown). Thus, the results with strain 5 corroborate the findings with strain 12 and the HMW1 and HMW2 proteins.

Example 5

To confirm an adherence function for the HMW1 and HMW2 proteins and to examine the effect of HMW1 and HMW2 independently of other *H. influenzae* surface structures, the hmw1 and the hmw2 gene clusters were introduced into *E. coli* DH5α, using plasmids pHMW1-14 and pHMW2-21, respectively. As a control, the cloning vector, pT7-7, was also transformed into *E. coli* DH5α. Western blot analysis demonstrated that *E. coli* DH5α containing the hmw1 genes expressed a 125 kDa protein, while the same strain harboring the hmw2 genes expressed a 120-kDa protein. *E. coli* DH5α containing pT7-7 failed to react with antiserum against recombinant HMW1. Transmission electron microscopy revealed no pili or other surface appendages on any of the *E. coli* strains.

Adherence by the *E. coli* strains was quantitated and compared with adherence by wild type non-typeable *H. influenzae* strain 12. As shown in Table 2 below, adherence by *E. coli* DH5α containing vector alone was less than 1% of that for strain 12. In contrast, *E. coli* DH5α harboring the hmw1 gene cluster demonstrated adherence levels comparable to those for strain 12. Adherence by *E. coli* DH5α containing the hmw2 genes was approximately 6-fold lower than attachment by strain 12 but was increased 20-fold over adherence by *E. coli* DH5α with pT7-7 alone. These results indicate that the HMW1 and HMW2 proteins are capable of independently mediating attachment to Chang conjunctival cells. These results are consistent with the results with the *H. influenzae* mutants reported in Examples 3 and 4, providing further evidence that, with Chang epithelial cells, HMW1 is a more efficient adhesin than is HMW2.

Experiments with *E. coli* HB101 harboring pT7-7, pHMW1-14, or pHMW2-21 confirmed the results obtained with the DH5α derivatives (see Table 2).

Example 6

HMW1 and HMW2 were isolated and purified from non-typeable *H. influenzae* (NTHI) strain 12 in the following manner. Non-typeable Haemophilus bacteria from frozen stock culture were streaked onto a chocolate plate and grown overnight at 37° C. in an incubator with 5% $CO_2$. 50 ml starter culture of brain heart infusion (BHI) broth, supplemented with 10 µg/ml each of hemin and NAD was inoculated with growth on chocolate plate. The starter culture was grown until the optical density (O.D.-600 nm) reached 0.6 to 0.8 and then the bacteria in the starter culture was used to inoculate six 500 ml flasks of supplemented BHI using 8 to 10 ml per flask. The bacteria were grown in 500 ml flasks for an additional 5 to 6 hours at which time the O.D. was 1.5 or greater. Cultures were centrifuged at 10,000 rpm for 10 minutes.

Bacterial pellets were resuspended in a total volume of 250 ml of an extraction solution comprising 0.5M NaCl, 0.01M $Na_2EDTA$, 0.01M Tris 50 µM 1,10-phenanthroline, pH 7.5. The cells were not sonicated or otherwise disrupted. The resuspended cells were allowed to sit on ice at 0° C. for 60 minutes. The resuspended cells were centrifuged at 10,000 rpm for 10 minutes at 4° C. to remove the majority of intact cells and cellular debris. The supernatant was collected and centrifuged at 100,000×g for 60 minutes at 4° C. The supernatant again was collected and dialyzed overnight at 4° C. against 0.01M sodium phosphate, pH 6.0.

The sample was centrifuged at 10,000 rpm for 10 minutes at 4° C. to remove insoluble debris precipitated from solution during dialysis. The supernatant was applied to a 10 ml CM Sepharose column which has been pre-equilibrated with 0.01M sodium phosphate, pH 6. Following application to this column, the column was washed with 0.01M sodium phosphate. Proteins were elevated from the column with a 0–0.5M KCl gradient in 0.01M Na phosphate, pH 6 and fractions were collected for gel examination. Coomassie gels of column fractions were carried out to identify those fractions containing high molecular weight proteins. The fractions containing high molecular weight proteins were pooled and concentrated to a 1 to 3 ml volume in preparation for application of sample to gel filtration column.

A Sepharose CL-4B gel filtration column was equilibrated with phosphate-buffered saline, pH 7.5. The concentrated high molecular weight protein sample was applied to the gel filtration column and column fractions were collected. Coomassie gels were performed an the column fractions to identify those containing high molecular weight proteins. The column fractions containing high molecular weight proteins were pooled.

The proteins were tested to determine whether they would protect against experimental otitis media caused by the homologous strain.

Chinchillas received three monthly subcutaneous injections with 40 µg of an HMW1-HMW2 protein mixture in Freund's adjuvant. One month after the last injection, the animals were challenged by intrabullar inoculation with 300 cfu of NTHI strain 12.

Infection developed in 5 of 5 control animals versus 5 of 10 immunized animals. Among infected animals, geometric mean bacterial counts in middle ear fluid 7 days post-challenge were $7.4 \times 10^6$ in control animals verus $1.3 \times 10^5$ in immunized animals.

Serum antibody titres following immunization were comparable in uninfected and infected animals. However, infection in immunized animals was uniformly associated with the appearance of bacteria down-regulated in expression of the HMW proteins, suggesting bacterial selection in response to immunologic pressure.

Although this data shows that protection following immunization was not complete, this data suggests the HMW adhesin proteins are potentially important protective antigens which may comprise one component of a multi-component NTHI vaccine.

These animal challenge tests were repeated in Chinchillas at a lower dose challenge than the 300 cfu employed above. In this instance, complete protection was achieved. In these experiments, groups of five animals were immunized with 20 μg of the HMW1-HMW2 mixture on days 1, 28, and 42 in the presence of AlPO$_4$. Blood samples were collected on day 53 to monitor the antibody response. On day 56, the left ear of animals was challenged with about 10 cfu of *H. influenzae* strain 12. Ear infection was monitored on day 4. Four animals in Group 3 were infected previously by *H. influenzae* strain 12 and were recovered completely for at least one month before the second challenge. The results are outlined in the following Table A:

TABLE A

Protective ability of HMW protein against non-typeable *H. influenzae* challenge in chinchilla model

| Group (#) | Antigens | Total Animals | Tympano-gram | Otoscopic Examination | cfu of Bacteria/ 10 μL |
|---|---|---|---|---|---|
| | | | Number of Animals Showed Positive Ear Infection | | |
| 1 | HMW | 5 | 0 | 0 | 0 |
| 2 | None | 5 | 5 | 5 | 850–3200 (4/5) |
| 3 | Convalescent | 4 | 0 | 0 | 0 |

Example 7

A number of synthetic peptides were derived from HMW1. Antisera then was raised to these peptides. The anti-peptide antisera to peptide HMW1-P5 was shown to recognize HMW1. Peptide HMW1-P5 covers amino acids 1453 to 1481 of HMW1, has the sequence VDEVIEAKRILEKVKDLSDEEREALAKLG (SEQ ID NO:9), and represents bases 1498 to 1576 in FIG. 10.

This finding demonstrates that the DNA sequence and the derived protein is being interpreted in the correct reading frame and that peptides derived from the sequence can be produced which will be immunogenic.

SUMMARY OF DISCLOSURE

In summary of this disclosure, the present invention provides high molecular weight proteins of non-typeable Haemophilus, genes coding for the same and vaccines incorporating such proteins. Modifications are possible within the scope of this invention.

TABLE 1

Effect of mutation of high molecular weight proteins on adherence to Chang epithelial cells by nontypable *H. influenzae*.

| Strain | ADHERENCE* | |
|---|---|---|
| | % inoculum | relative to wild type† |
| Strain 12 derivatives | | |
| wild type | 87.7 ± 5.9 | 100.0 ± 6.7 |
| HMW1-mutant | 6.0 ± 0.9 | 6.8 ± 1.0 |
| HMW2-mutant | 89.9 ± 10.8 | 102.5 ± 12.3 |
| HMW1-/HMW2-mutant | 2.0 ± 0.3 | 2.3 ± 0.3 |
| Strain 5 derivatives | | |
| wild type | 78.7 ± 3.2 | 100.0 ± 4.1 |
| HMW1-like mutant | 15.7 ± 2.6 | 19.9 ± 3.3 |
| HMW2-like mutant | 103.7 ± 14.0 | 131.7 ± 17.8 |
| double mutant | 3.5 ± 0.6 | 4.4 ± 0.8 |

*Numbers represent mean (± standard error of the mean) of measurements in triplicate or quadruplicate from representative experiments.
†Adherence values for strain 12 derivatives are relative to strain 12 wild type; values for strain 5 derivatives are relative to strain 5 wild type.

TABLE 2

Adherence by *E. coli* DH5α and HB101 harboring hmw1 or hmw2 gene clusters.

| Strain* | Adherence relative to *H. influenzae* strain 12† |
|---|---|
| DH5α (pT7-7) | 0.7 ± 0.02 |
| DH5α (pHMW1-14) | 114.2 ± 15.9 |
| DH5α (pHMW2-21) | 14.0 ± 3.7 |
| HB101 (pT7-7) | 1.2 ± 0.5 |
| HB101 (pHMW1-14) | 93.6 ± 15.8 |
| HB101 (pHMW2-21) | 3.6 ± 0.9 |

*The plasmid pHMW1-14 contains the hmw1 gene cluster, while pHMW2-21 contains the hmw2 gene cluster; pT7-7 is the cloning vector used in these constructs.
†Numbers represent the mean (± standard error of the mean) of measurements made in triplicate from representative experiments.

What we claim is:

1. A vaccine against diseased caused by non-typeable *Haemophilus influenza*, including otitis media, sinusitis and bronchitis, which comprises a mixture of (1) HMW1 encoded by the DNA sequence shown in FIG. 1 (SEQ ID No:1), having the derived amino acid sequence of FIG. 2 (SEQ ID No:2) and having an apparent molecular weight of 125 kDa and (2) HMW2 encoded by the DNA sequence shown in FIG. 3 (SEQ ID No:3), having the derived amino acid sequence of FIG. 4 (SEQ ID No:4) and having an apparent molecular weight of 120 kDa, and a physiological carrier for said mixture.

* * * * *

UNITED STATES PATENT AND TRADEMARK OFFICE
CERTIFICATE OF CORRECTION

PATENT NO. : 5,869,065
DATED : February 9, 1999
INVENTOR(S) : Stephen J. Barenkamp and Joseph William St. Geme III It is certified that error appears in the above-identified patent and that said Letters Patent is hereby corrected as shown below:

Title page, item [73],
Please change Name of Assignee from "Board of Trustees of the
                                   Leland Stanford Junior University
                                      Stanford, California" to --St. Louis University
St. Louis, Missouri
and
Washington University
St. Louis, Missouri--.

Signed and Sealed this

Seventh Day of March, 2000

Attest:

Q. TODD DICKINSON

Attesting Officer     Commissioner of Patents and Trademarks